United States Patent [19]

Manns et al.

[11] Patent Number: 5,018,212

[45] Date of Patent: May 21, 1991

[54] DEFECT AREA CONSOLIDATION FOR PATTERN INSPECTOR

[75] Inventors: William G. Manns; Anthony B. Wood, both of Dallas; David A. Norwood, Richardson; Don J. Weeks, Southlake; Michael Gordon, Dallas, all of Tex.

[73] Assignee: Texas Instruments Incorporated, Dallas, Tex.

[21] Appl. No.: 173,395

[22] Filed: Mar. 25, 1988

[51] Int. Cl.⁵ .................. G06K 9/00; H04N 7/18; G01N 21/00
[52] U.S. Cl. .................................... 382/8; 358/106; 356/237
[58] Field of Search .............. 358/106; 382/8, 28; 356/237

[56] References Cited

U.S. PATENT DOCUMENTS

| | | | |
|---|---|---|---|
| 3,851,951 | 12/1974 | Eveleth | 350/161 |
| 4,403,294 | 9/1983 | Hamada et al. | 358/106 |
| 4,541,712 | 9/1985 | Whitney | 355/53 |
| 4,587,617 | 5/1986 | Barker et al. | 358/106 |
| 4,620,288 | 10/1986 | Welmers | 364/518 |
| 4,692,943 | 9/1987 | Pietzsch et al. | 382/8 |
| 4,707,734 | 11/1987 | Labinger et al. | 358/106 |
| 4,783,826 | 11/1988 | Koso | 358/106 |
| 4,794,647 | 12/1988 | Forgues | 358/106 |

OTHER PUBLICATIONS

Bademian, "Acousto-Optic Laser Recording", Optical Engineering, Jan./Feb. 1981, vol. 20, No. 1, pp. 143-149 (p147).
Hammer, "In-Line Anamorphic Beam Expanders", 8/82, vol. 21, No. 115, Applied Optics, p. 2861.
Bademian, "Acousto Optic Laser Recording", SPIE, vol. 175, Airborne Recon. IV (1979), pp. 111-123 (117).
Merry, "Acousto-Optic Laser Scanning", SPIE vol. 169, Laser Printing (1979), pp. 56-59.

*Primary Examiner*—Leo H. Boudreau
*Assistant Examiner*—Michael R. Cammarata
*Attorney, Agent, or Firm*—James T. Comfort; Melvin Sharp; B. Peter Barndt

[57] ABSTRACT

A laser pattern inspection and/or writing system which writes or inspects a pattern on a target on a stage, by raster scanning the target pixels. Inspection can also be done by substage illumination with non-laser light. A database, organized into frames and strips, represents an ideal pattern as one or more polygons. Each polygon's data description is contained within a single data frame. The database is transformed into a turnpoint polygon representation, then a left and right vector representation, then an addressed pixel representation, then a bit-mapped representation of the entire target. Most of the transformations are carried out in parallel pipelines. Guardbands around polygon sides are used for error filtering during inspection. Guardbands are polygons, and frames containing only guardband information are sent down dedicated pipelines. Error filtering also is done at the time of pixel comparisons of ideal with real patterns, and subsequently during defect area consolidation. Defect areas are viewed as color overlays of ideal and actual target areas, from data generated during real time. Defect areas can be de-zoomed to allow larger target areas to be viewed. An autofocus keeps the scanning laser beam in focus on the target. The inspection system is used to find fiducial marks to orient the target prior to raster scanning. IC bars are provided with alignment marks for locating each IC bar. Interferometers or glass scale encoders allow the stage position to be known.

5 Claims, 56 Drawing Sheets

MAIN DIRECTORY RECORD 1

| | |
|---|---|
| WORD 1: | 8000 HEX. |
| WORD 2: | NUMBER OF TARGETS ON THIS TAPE. |
| WORD 3: | YEAR THIS TAPE WAS GENERATED (IN BINARY). |
| WORD 4: | DAY THIS TAPE WAS GENERATED (JULIAN-BINARY). |
| WORD 5: | UNITS THAT DATA IS IN. |
| WORD 6: | UNUSED. |
| WORD 7: | STRIP WIDTH IN ADDRESS UNITS (PIXELS). |
| WORD 8: | FRAME HEIGHT IN ADDRESS UNITS (PIXELS). |
| WORD 9: | 1 FOR RETICLE INSPECT, 3 FOR WRITE, 2 FOR MASK INSP. |
| WORDS 10-12: | NOT USED. |
| WORDS 13-39: | TEXAS INSTRUMENTS OWNERSHIP INFORMATION. |
| WORDS 40-50: | NOT USED. |
| WORDS 51, 52: | TOTAL NO. OF RECORD ON THIS TAPE. |
| WORD 53: | IF NOT ZERO THEN FRAMES ARE SERPENTINE. |
| WORDS 54-1997: | NOT USED. |
| WORDS 1998, 1999: | CURRENT RECORD NUMBER. |
| WORD 2000: | CHECKSUM. |

Fig. 10

MAIN DIRECTORY RECORD 2

| | |
|---|---|
| WORDS 1, 2: | FIRST HEADER RECORD NO. FOR FIRST TARGET. |
| WORDS 3-10: | 16 CHARACTER PART NUMBER FOR FIRST TARGET. |
| WORDS 11-12: | FIRST HEADER RECORD NO. FOR SECOND TARGET. |
| . | |
| . | |
| . | |
| WORDS 1998, 1999: | CURRENT RECORD NUMBER. |
| WORD 2000: | CHECKSUM. |

*Fig. 11*

TARGET HEADER RECORD 1

| | |
|---|---|
| WORDS 1, 2: | NOT USED. |
| WORDS 3, 4: | NO. OF POLYGONS FOR THIS TARGET. |
| WORD 5: | FIRST STRIP NO. THAT CONTAINS DATA. |
| WORD 6: | LAST STRIP NO. THAT CONTAINS DATA. |
| WORD 7: | FIRST FRAME THAT CONTAINS DATA. |
| WORD 8: | LAST FRAME THAT CONTAINS DATA. |
| WORDS 9, 10: | NOT USED. |
| WORDS 11-18: | 16 CHARACTER PART NUMBER |
| WORDS 19-1997: | NOT USED. |
| WORDS 1998, 1999: | CURRENT RECORD NUMBER. |
| WORD 2000: | CHECKSUM. |

*Fig. 12*

CONTROL WORD

BIT #

| Bit | Description |
|---|---|
| 15 | 1 FOR CONTROL WORD. 0 FOR DATA WORD. |
| 14 | 1 FOR REFERENCE. 0 FOR GUARD BAND. |
| 13 | SLOPE INFORMATION. |
| 12 | SLOPE INFORMATION. |
| 11, 10, 9, 8 | INFORMATION USED BY DPC2 IN CONSTRUCTING GUARD BANDS. NOT USED BY PATTERN WRITER. USED BY INSPECTOR. |
| 7, 6 | NOT USED. SET = 00. |
| 5, 4, 3, 2, 1, 0 | CONTROL BITS. |

Fig. 23

CONTROL BITS

| 00 | FIRST WORD ON TAPE. |
| 01 | BEGINNING OF STRIP. |
| 02 | BEGINNING OF FRAME. |
| 03 | END OF CURRENT BUFFER. |
| 04 | END OF TARGET. |
| 05 | END OF STRIP. |
| 06 | END OF FRAME. |

Fig. 24

BEGINNING OF STRIP

STRIP ID

BEGINNING OF FRAME

FRAME ID

BEGINNING OF POLYGON

X COORDINATE

Y COORDINATE

HEIGHT OR WIDTH

WIDTH OR HEIGHT

ETC.

BEGINNING OF POLYGON

X COORDINATE

Y COORDINATE

ETC.

END OF FRAME

FRAME ID

END OF STRIP

END OF TARGET

*Fig. 25*

ARGIS TAPE

313
{
8001   BEGINNING OF STRIP

0000   STRIP ID

314
{
- 8002   BEGINNING OF FRAME
- 0000   FRAME ID
- 8107   BEGINNING OF RECTANGLE
- 0100   X-COORDINATE ⎱ LOWER LEFT CORNER OF
- 01FF   Y-COORDINATE ⎰ RECTANGLE IN FRAME 0
- 0100   WIDTH (ACTUAL WIDTH - 1 PIXEL)
- 00FF   HEIGHT (ACTUAL HEIGHT - 1 PIXEL)
- 8006   END OF FRAME
- 0000   FRAME ID

315
{
- 8002   BEGINNING OF FRAME
- 0001   FRAME ID
- 8407   BEGINNING OF RECTANGLE
- 0100   X-COORDINATE ⎱ LOWER LEFT CORNER OF
- 00FF   Y-COORDINATE ⎰ RECTANGLE IN FRAME 1
- 0100   WIDTH (ACTUAL WIDTH - 1 PIXEL)
- 00FF   HEIGHT (ACTUAL HEIGHT - 1 PIXEL)
- 8006   END OF FRAME
- 0001   FRAME ID

8005   END OF STRIP

8004   END OF TARGET

Fig. 27

CONTROL WORD

8000   BEGINNING OF TARGET

8001   BEGINNING OF STRIP

8002   BEGINNING OF FRAME

8003   POLYGON START INDICATOR - GUARD BAND

8004   END OF TARGET

8005   END OF STRIP

8006   END OF FRAME

8007   END OF POLYGON

C003   POLYGON START INDICATOR - REFERENCE

*Fig. 28*

ARGIS DATA DISC (DPC2 OUTPUT)

319

| 8000 | BEGINNING OF TARGET |
| --- | --- |
| 1234 | TARGET ID |
| 8001 | BEGINNING OF STRIP |
| 0000 | STRIP ID |

320
| 8002 | | BEGINNING OF FRAME |
| --- | --- | --- |
| 0000 | | FRAME ID |
| C003 | | POLYGON START INDICATOR |
| 0100 | $X_0$ | LOWER LEFT CORNER |
| 01FF | $Y_0$ | |
| 0200 | $X_1$ | LOWER RIGHT CORNER |
| 01FF | $Y_1$ | |
| 0200 | $X_2$ | UPPER RIGHT CORNER |
| 0100 | $Y_2$ | |
| 0100 | $X_3$ | UPPER LEFT CORNER |
| 0100 | $Y_3$ | |
| 8007 | | END OF POLYGON |
| 8006 | | END OF FRAME |

CCW

Fig. 29

ARGIS DATA DISC
(DPC2 OUTPUT)

319

321 {
- 8002    BEGINNING OF FRAME
- 0001    FRAME ID
- C003    POLYGON START INDICATOR
- 0100    $X_0$ ⎫ LOWER LEFT CORNER
- 00FF    $Y_0$ ⎭
- 0200    $X_1$ ⎫ LOWER RIGHT CORNER
- 00FF    $Y_1$ ⎭
- 0200    $X_2$ ⎫ UPPER RIGHT CORNER
- 0000    $Y_2$ ⎭
- 0100    $X_3$ ⎫ UPPER LEFT CORNER
- 0000    $Y_3$ ⎭
- 8007    END OF POLYGON
- 8006    END OF FRAME

CCW

8005    END OF STRIP

8004    END OF TARGET

Fig. 30

|  | DPC3 | PREPROCESSOR |
|---|---|---|
| 25 BITS | | |
| 1036006 | | MOVE AT START OF EACH POLYGON TO: |
| 0000100 | $X_0$ | LOWER LEFT CORNER |
| 00001FF | $Y_0$ | |
| 1036007 | | DRAW: |
| 0000200 | $X_1$ | LOWER RIGHT CORNER |
| 00001FF | $Y_1$ | |
| 1036007 | | DRAW: |
| 0000200 | $X_2$ | UPPER RIGHT CORNER |
| 0000100 | $Y_2$ | |
| 1036007 | | DRAW: |
| 0000100 | $X_3$ | UPPER LEFT CORNER |
| 0000100 | $Y_3$ | |
| 1016008 | | END OF POLYGON |
| 101600A | | END OF FRAME |

ALTERNATE PIPELINE

25 BITS

326 {
| | | |
|---|---|---|
| 1036006 | MOVE TO: | |
| 0000100 | $X_0$ | } LOWER LEFT CORNER |
| 00000FF | $Y_0$ | |
| 1036007 | DRAW: | |
| 0000200 | $X_1$ | } LOWER RIGHT CORNER |
| 00000FF | $Y_1$ | |
| 1036007 | DRAW: | |
| 0000200 | $X_2$ | } UPPER RIGHT CORNER |
| 0000000 | $Y_2$ | |
| 1036007 | DRAW: | |
| 0000100 | $X_3$ | } UPPER LEFT CORNER |
| 0000000 | $Y_3$ | |
| 1016008 | END OF POLYGON | |
| 101600A | END OF FRAME | |
| 101600C | END OF STRIP | |

Fig. 31b

VECTOR REPRESENTATION
OF A POLYGON 335  334

350~ NN  ZZZZ        NN IS SLOPE CODE.  ZZZZ IS VECTOR LENGTH.

351~ 00  RRRR        NO COMMAND.  RRRR IS △X OR △Y.

352~ 00  SSSS        NO COMMAND.  SSSS IS ORIGIN X ADDR.

353~ 00  TTTT        NO COMMAND.  TTTT IS ORIGIN Y ADDR.

354~ 00  UUUU        NO COMMAND.  UUUU IS LEFT/RIGHT DIRECTION
                    INDICATOR.

355~ 00  KKKK        NO COMMAND.  KKKK IS UP/DOWN DIRECTION
                    INDICATOR.

.                   .

.                   .

.                   .

356~ 00  MMMM        02 IS END OF POLYGON COMMAND.  MMMM IS MIN Y.

357~ 00  PPPP        NO COMMAND.  PPPP IS MAX Y.

| MEMORY ADDR. (HEX) | 64 BIT WORD | |
|---|---|---|
| 0000 | 0 · · · 0 | |
| . | . | |
| . | . | |
| . | . | |
| . | . | |
| 0FFF | 0 · · · 0 | |
| 1000 | 0 · · · 0 | (START OF LINE Y = 100H) |
| 1001 | 0 · · · 0 | |
| 1002 | 0 · · · 0 | |
| 1003 | 0 · · · 0 | |
| 1004 | 1 · · · 1 | (LEFT EDGE OF 1ST LINE OF POLY.) |
| 1005 | 1 · · · 1 | |
| 1006 | 1 · · · 1 | |
| 1007 | 1 · · · 1 | |
| 1008 | 1 · · · 0 | (RIGHT EDGE OF 1ST LINE OF POLY.) |
| 1009 | 0 · · · 0 | |
| 100A | 0 · · · 0 | |
| 100B | 0 · · · 0 | |
| 100C | 0 · · · 0 | |
| 100D | 0 · · · 0 | |
| 100E | 0 · · · 0 | |
| 100F | 0 · · · 0 | (END OF LINE Y = 100H) |
| 1010 | 0 · · · 0 | |
| 1011 | 0 · · · 0 | |
| 1012 | 0 · · · 0 | |
| 1013 | 0 · · · 0 | |
| 1014 | 1 · · · 1 | (LEFT EDGE OF POLYGON) |

ARGIS DATA DISC (DPC2 OUTPUT)

FRAME 0

319

| | |
|---|---|
| 8000 | BEGINNING OF TARGET |
| 1234 | TARGET ID |
| 8001 | BEGINNING OF STRIP |
| 0000 | STRIP ID |
| 8002 | BEGINNING OF FRAME |
| 0000 | FRAME ID |
| C003 | POLYGON START INDICATOR |
| 0100 | $X_0$ } LOWER LEFT CORNER |
| 01FF | $Y_0$ |
| 0200 | $X_1$ } LOWER RIGHT CORNER |
| 01FF | $Y_1$ |
| 0200 | $X_2$ } UPPER RIGHT CORNER |
| 0100 | $Y_2$ |
| 0100 | $X_3$ } UPPER LEFT CORNER |
| 0100 | $Y_3$ |
| 8007 | END OF POLYGON |

COUNTER CLOCKWISE

Fig. 48a

ARGIS DATA DISC (DPC2 OUTPUT)   (CONTINUED)

FRAME 0

$254\begin{cases}\text{8003} & \text{GUARD BAND POLYGON START INDICATOR} \\ \text{01FD} & \left.X_0\right\} \text{ UPPER LEFT CORNER. RIGHT VERTICAL} \\ \text{00FD} & \left.Y_0\right\} \text{ GUARD BAND.} \\ \text{01FD} & \left.X_1\right\} \text{ LOWER LEFT CORNER.} \\ \text{01FF} & \left.Y_1\right\} \\ \text{0203} & \left.X_2\right\} \text{ LOWER RIGHT CORNER.} \\ \text{01FF} & \left.Y_2\right\} \\ \text{0203} & \left.X_3\right\} \text{ UPPER RIGHT CORNER.} \\ \text{00FD} & \left.Y_3\right\} \\ \text{8007} & \text{GUARD BAND POLYGON END INDICATOR} \end{cases}$

ARGIS DATA DISC (DPC2 OUTPUT)

| | | | |
|---|---|---|---|
| 8003 | | GUARD BAND POLYGON START INDICATOR | FRAME 0 |
| 00FD | $X_0$ | LOWER LEFT CORNER. UPPER HORIZONTAL GUARD BAND. | |
| 0103 | $Y_0$ | | |
| 0203 | $X_1$ | LOWER RIGHT CORNER | COUNTER CLOCKWISE |
| 0103 | $Y_1$ | | |
| 0203 | $X_2$ | UPPER RIGHT CORNER. | |
| 00FD | $Y_2$ | | |
| 00FD | $X_3$ | UPPER LEFT CORNER. | |
| 00FD | $Y_3$ | | |
| 8007 | | GUARD BAND POLYGON END INDICATOR | |

255 brackets the above block.

| | | | |
|---|---|---|---|
| 8003 | | GUARD BAND POLYGON START INDICATOR | |
| 00FD | $X_0$ | UPPER LEFT CORNER. LEFT VERTICAL GUARD BAND. | |
| 00FD | $Y_0$ | | |
| 00FD | $X_1$ | LOWER LEFT CORNER. | COUNTER CLOCKWISE |
| 01FF | $Y_1$ | | |
| 0103 | $X_2$ | LOWER RIGHT CORNER. | |
| 01FF | $Y_2$ | | |
| 0103 | $X_3$ | LOWER RIGHT CORNER. | |
| 00FD | $Y_3$ | | |
| 8007 | | GUARD BAND POLYGON END INDICATOR | |
| 8006 | | END OF FRAME | |

256 brackets the second block.

Fig. 48b

DPC3 → PIPELINES

REFERENCE DATA IS JUST LIKE THE WRITER, BUT ALL FRAMES OF REFERENCE DATA GO TO THE REFERENCE DATA PIPELINE.

GUARD BAND DATA GOES TO GUARD BAND DATA PIPELINE.

GUARD BAND DATA

25 BITS

| | | |
|---|---|---|
| 1036006 | | MOVE TO: (USED @ START OF POLYGON) |
| 00001FD | $X_0$ | UPPER LEFT CORNER. RIGHT |
| 00000FD | $Y_0$ | VERTICAL GUARD BAND. |
| 1036007 | | DRAW: |
| 00001FD | $X_1$ | |
| 00001FF | $Y_1$ | LOWER LEFT CORNER |
| 1036007 | | DRAW: |
| 0000203 | $X_2$ | |
| 00001FF | $Y_2$ | LOWER RIGHT CORNER |
| 1036007 | | DRAW: |
| 0000203 | $X_3$ | |
| 00000FD | $Y_3$ | UPPER RIGHT CORNER |
| 1016008 | | END OF POLYGON |

*Fig. 49a*

```
                        DPC3 ──▶ PIPELINE
  25 BITS
 ┌───┴───┐
 1036006      (START OF G.B. POLYGON) MOVE TO:

00000FD    X₀ ⎤  LOWER LEFT CORNER. UPPER
               ⎬  HORIZONTAL GUARD BAND
 0000103    Y₀ ⎦

1036007         DRAW:

0000203    X₁ ⎤
               ⎬ LOWER RIGHT CORNER
 0000103    Y₁ ⎦

1036007         DRAW:

0000203    X₂ ⎤
               ⎬ UPPER RIGHT CORNER
 00000FD    Y₂ ⎦

1036007         DRAW:

00000FD    X₃ ⎤
               ⎬ UPPER LEFT CORNER
 00000FD    Y₃ ⎦

1016008         END OF POLYGON 1036006      (START OF G.B. POLYGON) MOVE TO:

00000FD    X₀ ⎤  UPPER LEFT CORNER. LEFT
               ⎬  VERTICAL GUARD BAND.
 00000FD    Y₀ ⎦

1036007         DRAW:

00000FD    X₁ ⎤
               ⎬ LOWER LEFT CORNER
 00001FF    Y₁ ⎦

1036007         DRAW:

0000103    X₂ ⎤
               ⎬ LOWER RIGHT CORNER
 00001FF    Y₂ ⎦

1036007         DRAW:

0000103    X₃ ⎤
               ⎬ UPPER RIGHT CORNER
 00000FD    Y₃ ⎦

1016008         END OF POLYGON

101600A         END OF FRAME
```

*Fig. 49b*

PRE-PROCESSOR → FIGURE FILLER (GUARD BAND PIPELINE)   FRAME 0

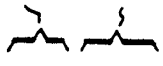

6 BITS COMMAND / 16 BITS DATA

| Command | Data | | Description |
|---|---|---|---|
| 07 | 0102 | | 102H = VECTOR LENGTH (A.L. - 1). |
| 00 | 01FD | $X_0$ | UPPER LEFT CORNER. (RIGHT VERT. G.B.) VECTOR ORIGIN. |
| 00 | 00FD | $Y_0$ | |
| 00 | 0001 | | VECTOR DIRECTION (↓, + 1 IN 2'S C). |
| 07 | 0102 | | 102H = VECTOR LENGTH (A.L. - 1). |
| 00 | 0203 | $X_2$ | LOWER RIGHT CORNER. VECTOR ORIGIN. |
| 00 | 01FF | $Y_2$ | |
| 00 | FFFF | | VECTOR DIRECTION (↑, - 1 IN 2'S C). |
| 02 | 00FD | | 02 = END OF POLYGON. FD = MIN Y. |
| 00 | 01FF | | 1FF = MAX Y. Y BOUNDARY. |
| 07 | 0006 | | 6 = VECTOR LENGTH (A.L. - 1). |
| 00 | 00FD | $X_3$ | UPPER LEFT CORNER. UPPER HORIZ. G.B. VECTOR ORIGIN. |
| 00 | 00FD | $Y_3$ | |
| 00 | 0001 | | VECTOR DIRECTION (↓, + 1 IN 2'S C). |
| 07 | 0006 | | 6 = VECTOR LENGTH (A.L. - 1). |
| 00 | 0203 | $X_1$ | LOWER RIGHT CORNER VECTOR ORIGIN. |
| 00 | 0103 | $Y_1$ | |
| 00 | FFFF | | VECTOR DIRECTION (↑, - 1 IN 2'S C). |
| 02 | 00FD | | 02 = END OF POLYGON. FD = MIN Y. |
| 00 | 0103 | | 103H = MAX Y. Y BOUNDARY. |

*Fig. 50a*

PRE-PROCESSOR → FIGURE FILLER (GUARD BAND PIPELINE)  FRAME 0

| 6 BITS COMMAND | COMMAND 16 BITS DATA | | |
|---|---|---|---|
| 07 | 0102 | | 102H = VECTOR LENGTH (A.L. - 1). |
| 00 | 00FD | $X_0$ | UPPER LEFT CORNER (LEFT. |
| 00 | 00FD | $Y_0$ | VERT. G.B.). VECTOR ORIGIN. |
| 00 | 0001 | | VECTOR DIRECTION (↓, + 1 IN 2'S C). |
| 07 | 0102 | | 102H = VECTOR LENGTH (A.L. - 1). |
| 00 | 0103 | $X_2$ | LOWER RIGHT CORNER. |
| 00 | 01FF | $Y_2$ | VECTOR ORIGIN. |
| 00 | FFFF | | VECTOR DIRECTION (↑, - 1 IN 2'S C). |
| 02 | 00FD | | 02 = END OF POLYGON. FD = MIN Y. |
| 00 | 01FF | | 1FF = MAX Y.  Y BOUNDARY. |
| 04 | 0000 | | END OF FRAME. |

Fig. 50b

FIGURE FILLER → PIXEL MEMORY

FRAME 0

```
  342      341      340
COMMAND  Y-ADDR.  X-ADDR.
 5 BITS  10 BITS  10 BITS
```

| | | | |
|---|---|---|---|
| 1C | 0FD | 1FD | ⎫ OR DATA IN P.M. X-Y WITH |
| 07 | 000 | 007 | ⎬ FOLLOWING DATA: 000007.07 = LOAD DATA |
| 1C | 0FD | 200 | ⎫ OR DATA IN P.M. @ X-Y WITH |
| 07 | 03C | 000 | ⎭ 03C000. Y=FD, RIGHT VERT. G.B. |

| | | | |
|---|---|---|---|
| 1C | 0FE | 1FD | ⎫ |
| 07 | 000 | 007 | ⎬ OR (X-Y) WITH 000007 |
| 1C | 0FE | 200 | ⎬ Y = FE. |
| 07 | 03C | 000 | ⎭ |

. 
. 
.

| | | | |
|---|---|---|---|
| 1C | 1FF | 1FD | ⎫ |
| 07 | 000 | 007 | ⎬ Y = 1FF. |
| 1C | 1FF | 200 | ⎬ |
| 07 | 03C | 000 | ⎭ |

Fig. 51a

FIGURE FILLER     PIXEL MEMORY

FRAME 0

|  Y  |  X  |
|---|---|
| 5 BITS | 10 BITS | 10 BITS |

| | | |
|---|---|---|
| 1C | 0FD | 0FD |
| 07 | 000 | 007 |
| 03 | 0FD | 100 |
| 03 | 0FD | 140 |
| 03 | 0FD | 180 |
| 03 | 0FD | 1C0 |
| 1C | 0FD | 200 |
| 07 | 03C | 000 |

UPPER HORIZONTAL GUARD BAND
Y=FD.

. . .

| | | |
|---|---|---|
| 1C | 103 | 0FD |
| 07 | 000 | 007 |
| 03 | 103 | 100 |
| 03 | 103 | 140 |
| 03 | 103 | 180 |
| 03 | 103 | 1C0 |
| 1C | 103 | 200 |
| 07 | 03C | 000 |

OUTPUT FROM PIXEL MEMORY

FRAME 0

| MEMORY ADDR. (HEX) | 64 BIT WORD | |
|---|---|---|
| 0000 | 0 · · · 0 | |
| . | 0 · · · 0 | |
| . | 0 · · · 0 | |
| . | 0 · · · 0 | |
| . | 0 · · · 0 | |
| 0FCF | 0 · · · 0 | |
| 0FD0 | 0 · · · 0 | START OF LINE Y=FD |
| 0FD1 | 0 · · · 0 | |
| 0FD2 | 0 · · · 0 | |
| 0FD3 | 0 · 1 1 1 | 1'S START LEFT OF GUARD BANDS. |
| 0FD4 | 1 · · · 1 | |
| 0FD5 | 1 · · · 1 | |
| 0FD6 | 1 · · · 1 | |
| 0FD7 | 1 · · · 1 | |
| 0FD8 | 1 1 1 1 0 · · · 0 | RIGHT EDGE OF LIST LINE OF G.B. |

DEFECT AREA CONSOLIDATION FOR PATTERN INSPECTOR

This application is related to the following applications assigned to Texas Instruments Incorporated: LASER PATTERN WRITER/INSPECTOR, Ser. No. 173,774, filed Mar. 25, 1988, LASER PATTERN INSPECTOR, Ser. No. 173,494, filed Mar. 25, 1988, LASER PATTERN WRITER, Ser. No. 173,775, filed Mar. 25, 1988, GUARDBANDS FOR PATTERN INSPECTOR, Ser. No. 173,776, filed Mar. 25, 1988, TARGET AUTOALIGNMENT FOR PATTERN INSPECTOR OR WRITER, Ser. No. 173,504, filed Mar. 25, 1988, GENERATION ON THE FLY OF REFERENCE DISPLAY DATA, Ser. No. 173,706, filed Mar. 25, 1988, IMAGE FILLING FOR PATTERN WRITER OR INSPECTOR, Ser. No. 173,495, filed Mar. 25, 1988, GENERATION ON THE FLY OF TARGET PATTERN DATA, Ser. No. 173,773, filed Mar. 25, 1988, EXPANSION OF COMPACT DATABASE FOR PATTERN INSPECTOR OR WRITER, Ser. No. 173,710, filed Mar. 25, 1988, DEFECT AREA CONSOLIDATION FOR PATTERN INSPECTOR, Ser. No. 173,395, filed Mar. 25, 1988, ILLUMINANT AND DETECTION OF TARGET PIXELS FOR INSPECTION, Ser. No. 173,780, filed Mar. 25, 1988, DATA HANDLING SYSTEM FOR PATTERN INSPECTOR OR WRITER, Ser. No. 173,523, filed Mar. 25, 1988, SMOOTHING FILTER FOR STAGE POSITION PULSES, Ser. No. 173,777, filed Mar. 25, 1988, PARALLEL PIPELINES FOR PARALLEL DATA EXPANSION; Ser. No. 173,781, filed Mar. 25, 1988, COLOR OVERLAY OF SCANNED AND REFERENCE IMAGES FOR DISPLAY; Ser. No. 173,472, filed Mar. 25, 1988, AUTOFOCUS FOR SCANNING LASER INSPECTOR OR WRITER; Ser. No. 173,707, filed Mar. 25, 1988, BAR-BY-BAR DATA ALIGNMENT FOR MULTIPLE IC BARS, Ser. No. 173,772, filed Mar. 25, 1988, POSITION COMPENSATION OF LASER SCAN FOR STAGE MOVEMENT, Ser. No. 173,492, filed Mar. 25, 1988, PARALLEL PROCESSING OF REFERENCE AND GUARDBAND DATA, Ser. No. 173,708, filed Mar. 25, 1988, STAGE ILLUMINATION FOR PATTERN INSPECTOR, Ser. No. 173,778, filed Mar. 25, 1988, DEZOOM OF DEFECT AREAS FOR DISPLAY, Ser. No. 173,208, filed Mar. 25, 1988, COMPARATOR ERROR FILTERING FOR PATTERN INSPECTOR, Ser. No. 173,322, filed Mar. 25, 1988.

BACKGROUND OF THE INVENTION

1. Field of the Invention

This invention pertains to laser writers for exposing patterns on light-sensitive photoresist on semiconductor wafers, printed circuit boards, photomasks, hybrid circuit boards, ceramic boards and the like, and for exposing patterns on light-sensitive film or glass and the like.

2. Description of the Related Art

Many areas of technology are today heavily dependent on the availability of semicustom and custom integrated circuits, such as gate arrays and ASICs (Application Specific Integrated Circuits). Long cycle time in the development of these key components frequently results in components that have not been optimized adequately and that have been very expensive to develop. Extensive computer simulation is required to reduce the number of redesigns. Even with this simulation, system validation requires actual devices for in-circuit testing. Better system performance often can be obtained with less simulation by the early availability of low cost prototype integrated circuit devices.

Effective prototyping of integrated circuit devices requires several key features. Initially, effective design capture is required. This capability has been broadly implemented in the industry with tools such as CAD/CAM. The initial data checking and validation tools are in place and broadly used. Standard design flows have been established from this design capture area to the patterning data bases. These flows can usually be executed quickly, often resulting in overnight delivery of the plot data base.

Frequently, long delays occur at this point. The conventional approach is to fabricate and qualify a standard set of production, high volume photomasks at a high cost, and days to weeks of processing, queing, and qualification time. When the actual semiconductor wafers are to have their photoresist exposed, processing capacity is significantly reduced by the downtime required for loading, aligning, and calibrating each new reticle, for example. This can be as quick as one minute or, more commonly, as long as 15 minutes. Thus, the capacity of a critical piece of equipment such as a wafer stepper can drop below four wafers per hour. From the standpoint of assured integrated circuit device completion, it is desirable to write more than one wafer. If only one integrated circuit device design is used per wafer, the result can be building more than 1200 devices for a prototype test run of three wafers. If more than one integrated circuit design is used per wafer, then the reticle loading problems become even more severe. The end result is very expensive, long turnaround prototype integrated circuit device fabrication. The severity of the problem increases as the number of custom features in an integrated circuit device increases. Thus, semi-custom devices such as gate arrays commonly are fabricated notwithstanding these difficulties, but prototyping of fully custom devices is usually restricted to long production runs or to very high value products.

An alternative to photolithographic steppers is direct e-beam patterning, which has been applied in a limited number of cases. E-beam patterning has proven effective where small quantities of very high value devices are being built. An advantage to e-beam machines is that it can be practical to fabricate multiple integrated circuit designs on a single wafer since no physical mask or reticle is required. E-beam machines are, however, very costly and slow, resulting in patterning costs that are not acceptable for production runs, once the prototype devices have been produced. Furthermore, e-beam machines have a poor record of uptime, which further restricts their use for photolithographic writing on wafers. Another disadvantage to e-beam wafer writers is that they require the use of special electron beam sensitive resists. These resists have not shown the chemical durability or freedom from defects known as pinhole defects, obtainable with modern optically sensitive photoresists. Thus, e-beam masks require inspection and frequently require repair to achieve acceptable defect levels. With resist coated wafers, however, this type of repair is not physically practical.

Printed wiring board fabrication has the same types of patterning problems as those of integrated circuit patterns on wafers, but on a different scale. Printed wiring boards may be exposed by writing directly on photoresist covering the surface of a board, using a beam of light or electrons. Alternatively, exposure can take place by projecting patterns of light and dark on the surface of a board using a glass plate or film artwork.

In addition to the same problems already mentioned above concerning e-beam use for direct patterning on wafers, e-beams could not be used to produce patterns on printed wiring boards much above six inches by six inches. For printed wiring boards greater than this size, glass plate or film artwork or masks would have to be used. It should be noted, however, that e-beam machines normally are not used to produce printed wiring boards and such use is only hypothetical. The standard printed wiring board mask manufacturing machine has been Gerber, which uses photographic exposure through various apertures to describe the geometries.

Current systems for creating printed wiring board masks suffer from problems of poor fabrication cycle time, storage and maintenance of master artwork over a period of years. Additionally, the artwork must be carefully inspected for errors, adding to the cycle time.

Attempts have been made to produce a laser writer capable of writing directly on photoresist or creating printed wiring board artwork, using rotating mirror technology. Rotating mirror technology has been used to produce laser character printers, however, in the field of artwork generation and direct writing on printed wiring boards, the technology has some serious drawbacks.

Prior art rotating mirror scanner laser writers for printed wiring board applications produce what is basically a circular scan. For these systems to write at uniform velocity, an F-theta lens is required. The field correction provided by this lens is incomplete. If reasonably accurate laser beam positioning on a target is to be achieved, additional levels of position correction are required. Some of these correction techniques include the use of a separate pilot laser position sensing beam monitored by a CCD line scanner, or the equivalent. Other correction methods include the use of galvanometer mirror systems to apply corrections. All of these methods of correction result in incomplete correction that limits the accuracy and resolution of these systems.

Another source of errors inherent in the use of rotating mirror systems is the multifaceted mirror assembly itself. Small mirror assemblies are limited in the number of reflecting sides that can be ground on the assembly, and still maintain the necessary accuracy.

Larger mirror assemblies may be used to correct the problems inherent in small mirror assemblies, however, larger rotating mirror assemblies suffer from distortion caused by forces generated by the necessary large rotational velocities.

Mirror assemblies also suffer from problems of balance and the support bearing performance.

As a consequence of the problems inherent in rotating mirror writer systems, the systems are limited in writing speed, accuracy and stability by the mirror assembly problems mentioned above.

Another attempt to produce a laser writing system uses an acousto-optical Bragg cell as a laser beam deflector. This system is disclosed in U.S. Pat. Nos. 4,541,712 and 4,620,288. What is disclosed is a laser-based pattern generating system for writing patterns on light-sensitive material to produce reticles and for direct on-wafer pattern generation. This system uses a beam splitter to split a laser beam into an array of sixteen parallel beams, which is swept by the Bragg cell from side-to-side in raster-scan fashion to form swaths of sixteen parallel rows of modulated-light-exposed strips on the surface of a target such as a reticle or wafer. The swaths are laid down in parallel rows contiguous to one another to build up, swath-at-a-time, a desired image on the target surface.

After the 16 laser beams pass through the beam splitter they are individually modulated using acousto-optical modulators. The beams are then recombined in an attempt to form an array of precisely spaced, parallel beams which must strike the surface of the target in a precisely spaced pattern. This is required to achieve accurately parallel lines and to prevent wave interference effects between the beams.

After the 16 beams are recombined they are deflected by the Bragg cell deflector in raster scan fashion to sweep across the surface of the target. The acousto-optical bragg cell for deflecting the 16 recombined beams has a sweep rate dependent upon the frequency slew rate of the oscillator producing acoustic waves travelling transversely to the optical axis in the deflector. Linearity of slew rate is very difficult to achieve, which means that linearity in the sweep of the laser array is impossible to achieve for all practical purposes.

SUMMARY OF THE INVENTION

A computerized method of eliminating false defect areas and consolidating defect areas in a pattern inspection system, comprising the steps of: comparing, one-by-one, the pixels of an ideal pattern with the corresponding pixels of a pattern on a target; counting the numbers of adjacent overlapping rows of miscompared pixels; comparing the number of rows of miscompared pixels with a first error criterion allowance; designating the miscompared pixels as a defect area if the first error criterion allowance comparisons produce a miscompare; designating first and second designated defect areas as a single consolidated defect area if the first and second designated defect areas are separated by a number of pixels less than or equal to a second error criterion allowance.

The computerized method, wherein the separation in number of pixels compared with the second error criterion allowance, is measured in the X or Y direction.

The computerized method, further comprising the steps of: storing the minimum and maximum X coordinates of the consolidated defect area; and storing the minimum and maximum Y coordinates of the consolidated defect area.

The computerized method, further comprising the step of: storing the area in number of pixels, of the consolidated defect area.

The computerized method, wherein the step of comparing the pixels of the ideal pattern with the pixels of the pattern on the target, includes the step of: comparing, one-by-one, the bits of a bit-map of an ideal target, including the ideal pattern, with the corresponding pixels of the inspected target, including the pattern on the inspected target, wherein the pixels of the ideal pattern are the bits of the portion of the bit-map representing the ideal pattern.

BRIEF DESCRIPTION OF THE DRAWINGS

FIG. 10 is a table illustrating the contents of Main Directory Record 1 of the tape resident database.

FIG. 11 is a table illustrating the contents of Main Directory Record 2 of the tape resident database.

FIG. 12 is a table illustrating the content of Target Header Record 1 of the tape resident database.

FIG. 23 is a table showing the bit positions for the control words used in the tape resident database.

FIG. 24 is a table defining the meaning of the control bits of the control word.

FIG. 25 is a table indicating the structure of the Data Records of the tape resident database.

FIG. 27 is a listing showing the tape resident database Data Records for the example pattern of FIG. 26.

FIG. 28 is a table of the meanings of the various control words used in the disk resident database.

FIGS. 29 and 30 are listing of the data output by DPC2 for the example pattern of FIG. 26.

FIG. 31 is a listing of the data output by DPC3 for the example pattern of FIG. 26.

FIG. 34 is a table indicating the meaning of the command and data words for the vector representation of a pattern.

FIG. 37 is a listing of the bit-mapped data output by the pixel memory modules for the example pattern of FIG. 26.

FIGS. 48A and 48B are listing of the output of DPC2 for the first frame of data for the example pattern of FIG. 47.

FIGS. 49A and 49B are listings of the output of DPC3 for the guardband data only, for the example pattern of FIG. 47.

FIGS. 50A and 50B are listings of the output of the preprocessor(s) for the guardband data only, for the example pattern of FIG. 47.

FIGS. 51A through 51C are listings of the output of the filler module(s) for the guardband data only, for the example pattern of FIG. 47.

FIG. 52 is a listing of the bit-mapped output of the pixel memory(s) for the guardband data, for the example pattern of FIG. 47.

DESCRIPTION OF THE PREFERRED EMBODIMENTS

Pattern Writing

Figure 1:
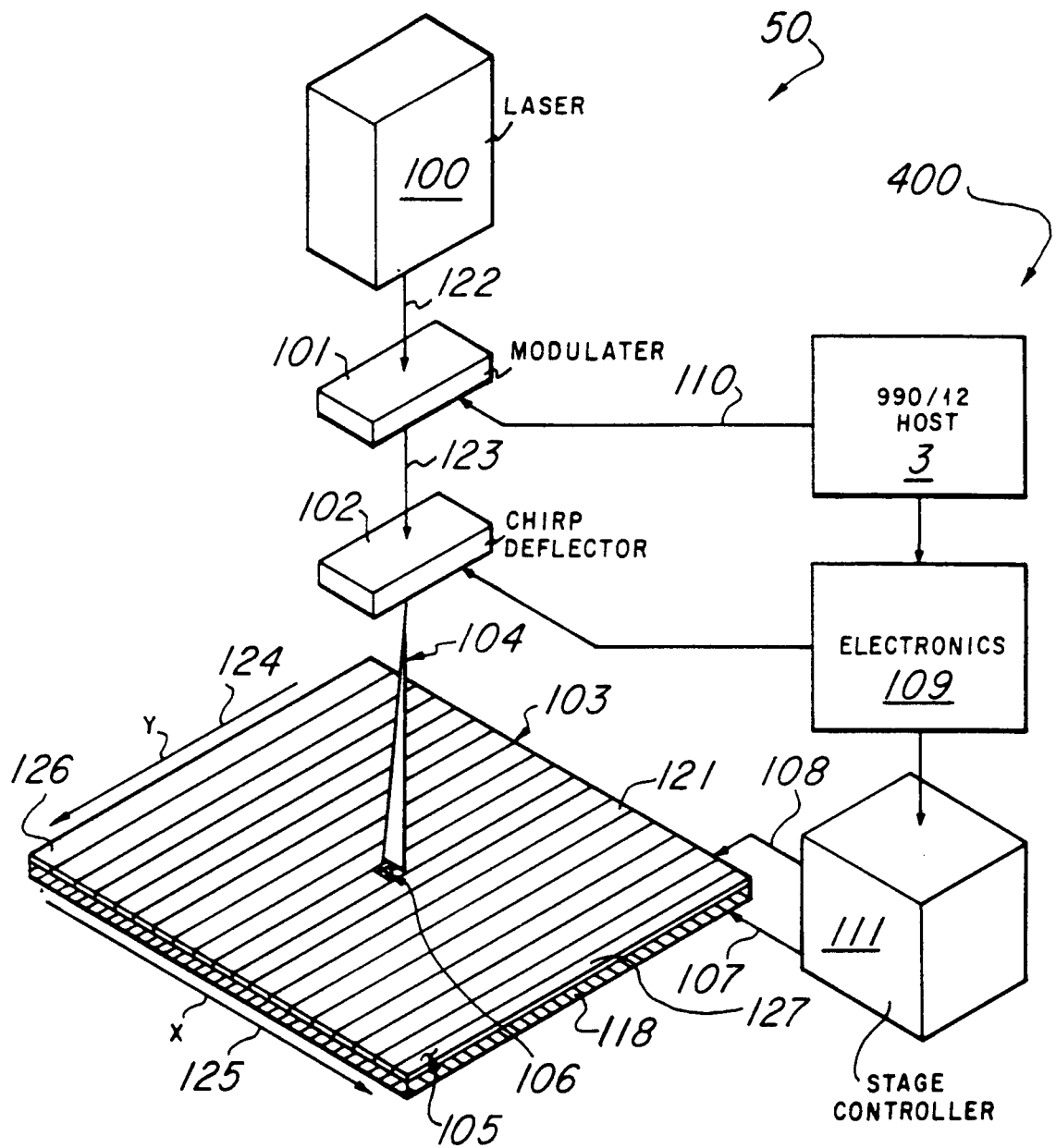
FIG. 1 is a block diagram, isometric view of an embodiment of the laser pattern writer or inspector writing or inspecting a pattern on a target.

FIG. 1 shows the pattern writer system 50 with a target 103 having a photosensitive surface 121, mounted on granite stage 118. The target may be a reticle, a semiconductor wafer with photoresist on its face, a glass plate with a photosensitive surface layer, a photographic film or a printed wiring board with photoresist on its face. In addition, the invention comprehends use with photosensitive surfaces in general.

An argon ion laser 100 emits laser beam 122 which enters electro-optical modulator 101 which modulates laser beam 122 by letting the beam pass through or blocking it in correspondence to the serial bit pattern received in serial pixel bit stream 110. Electro-optical modulator 101 is purchased from Conoptics Incorporated from Danbury, Conn. A Conoptics Model 100 is used when a modulation rate between 50 MHZ and 100 MHZ is desired, and a Model 50 is used when 50 Mhz or less is satisfactory. The modulator 101 is used in the binary output mode of either letting 011 incident light pass through or else blocking the light entirely.

Figure 5:
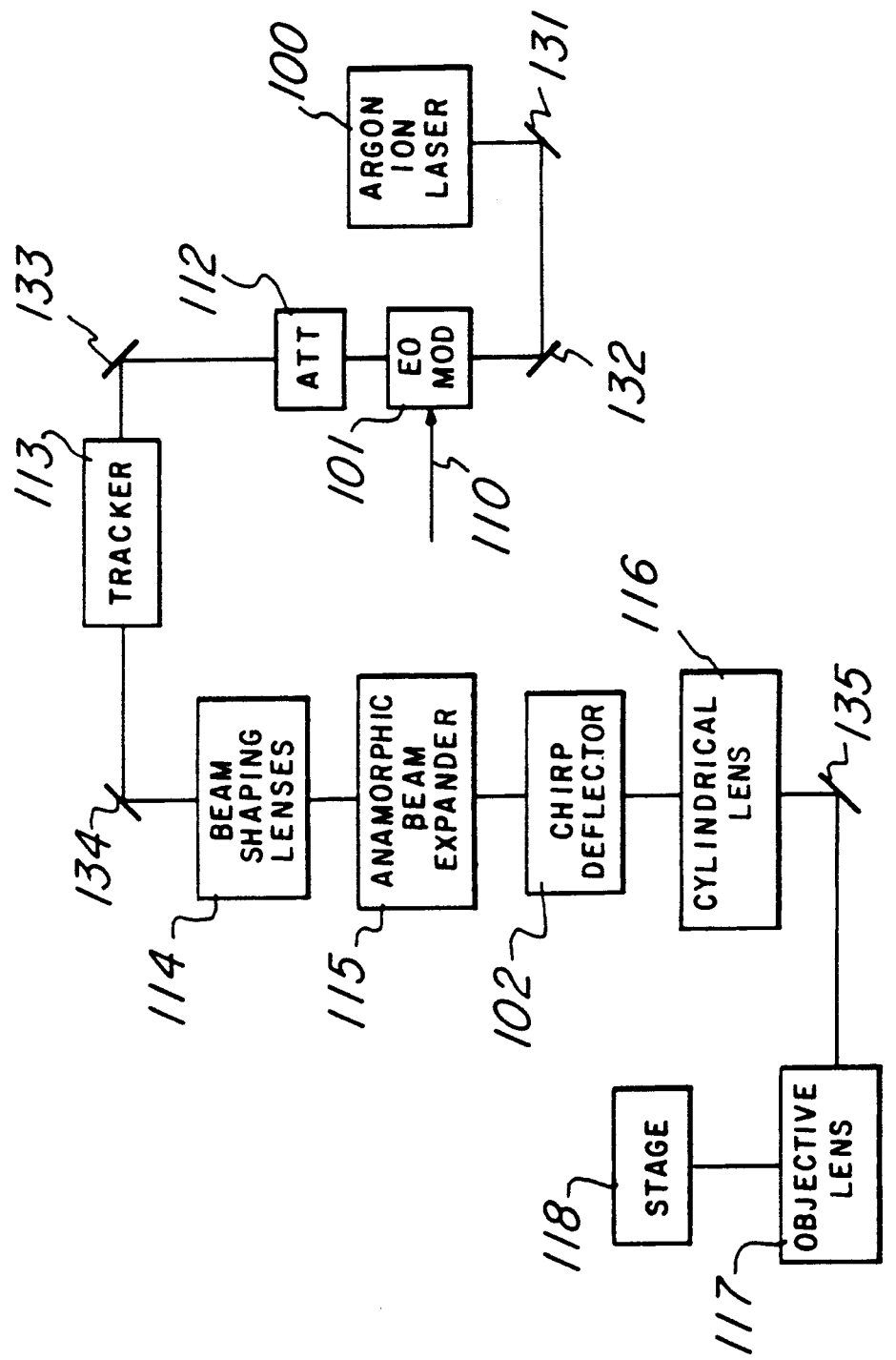
FIG. 5 is a block diagram showing the laser and optical system of the laser pattern writer or inspector.

After passing through a Bragg cell tracker 113 and beam shaping optics 114, 115, shown in FIG. 5, modulated laser beam 123 enters chirp deflector 102. Chirp deflector 102 is an acousto-optical deflector which causes the laser beam 104 to sweep out raster scan lines on the photosensitive surface 121 of target 103. The surface 103 will have that portion of its surface raster scanned as requires exposure to light in the desired geometrical patterns. The surface 121 will be developed after the desired geometries have been written by the raster scanned laser beam 104, and the photoresist which was not exposed to the laser beam will thus be removed to expose the surface beneath the photoresist. Typically, in integrated circuit manufacture, this exposed surface will be a layer of metal which will be etched away, leaving a metallic circuit pattern under and defined by the exposed photoresist.

The stage 118 is capable of bi-directional movement along both the X axis 125 and the Y axis 124. The stage also is capable of rotational movement in the X-Y plane, about an axis perpendicular to the X axis 125 and the Y axis 124, to align the target 103 with respect to the X and Y axes. The chirp deflector 102 produces scanning or deflection in the X direction only. Relative Y direction motion between the target 103 and the scanning laser beam 104 is produced by moving the stage 118 in the plus or minus Y direction. The coordinate system for the target 103 is chosen so that the positive Y direction is indicated by the direction of Y axis arrow 124. This is opposite the conventional way of assigning a sign to a Y coordinate. The positive X direction is conventional and is in the direction of X axis arrow 125.

Figure 2:
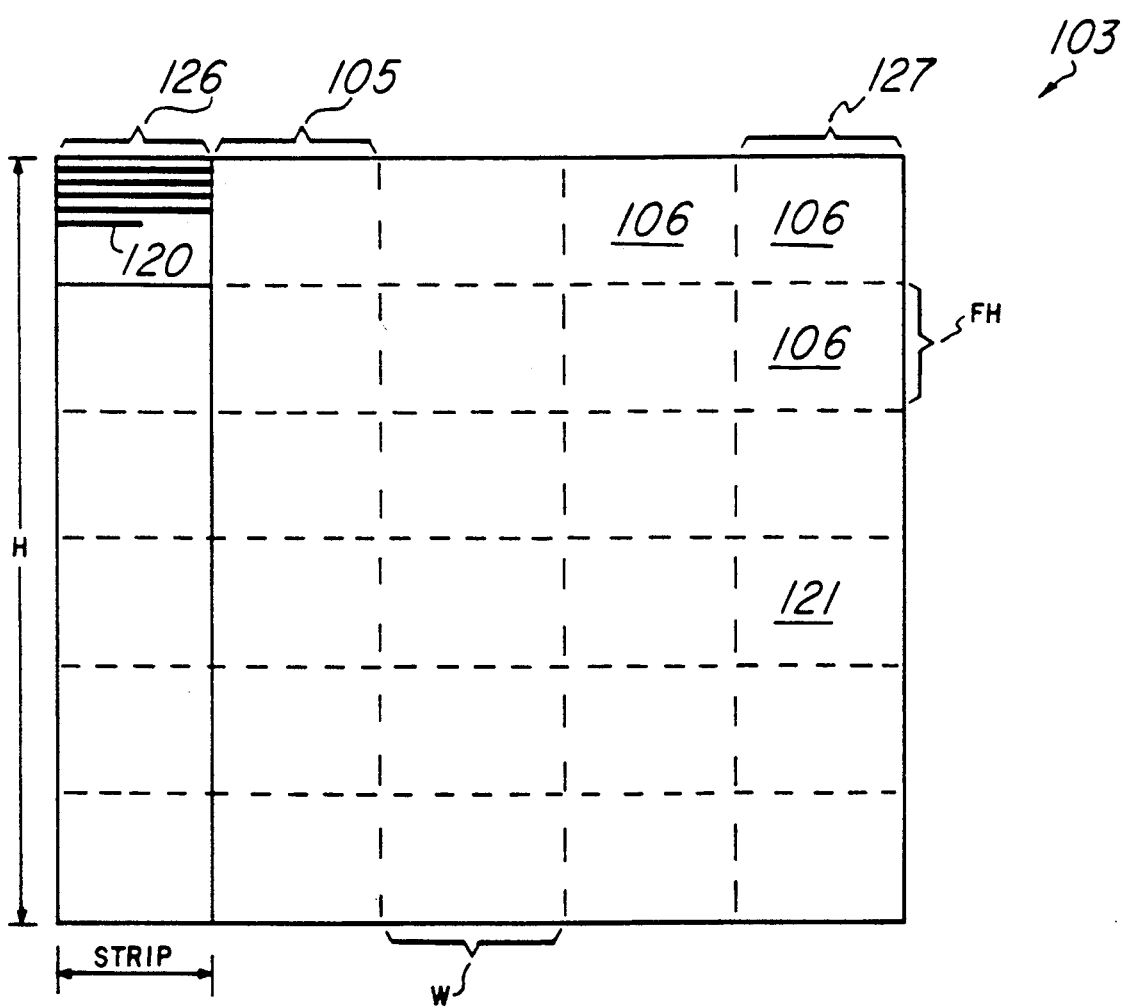
FIG. 2 is a plan view of a target.
Figure 3:
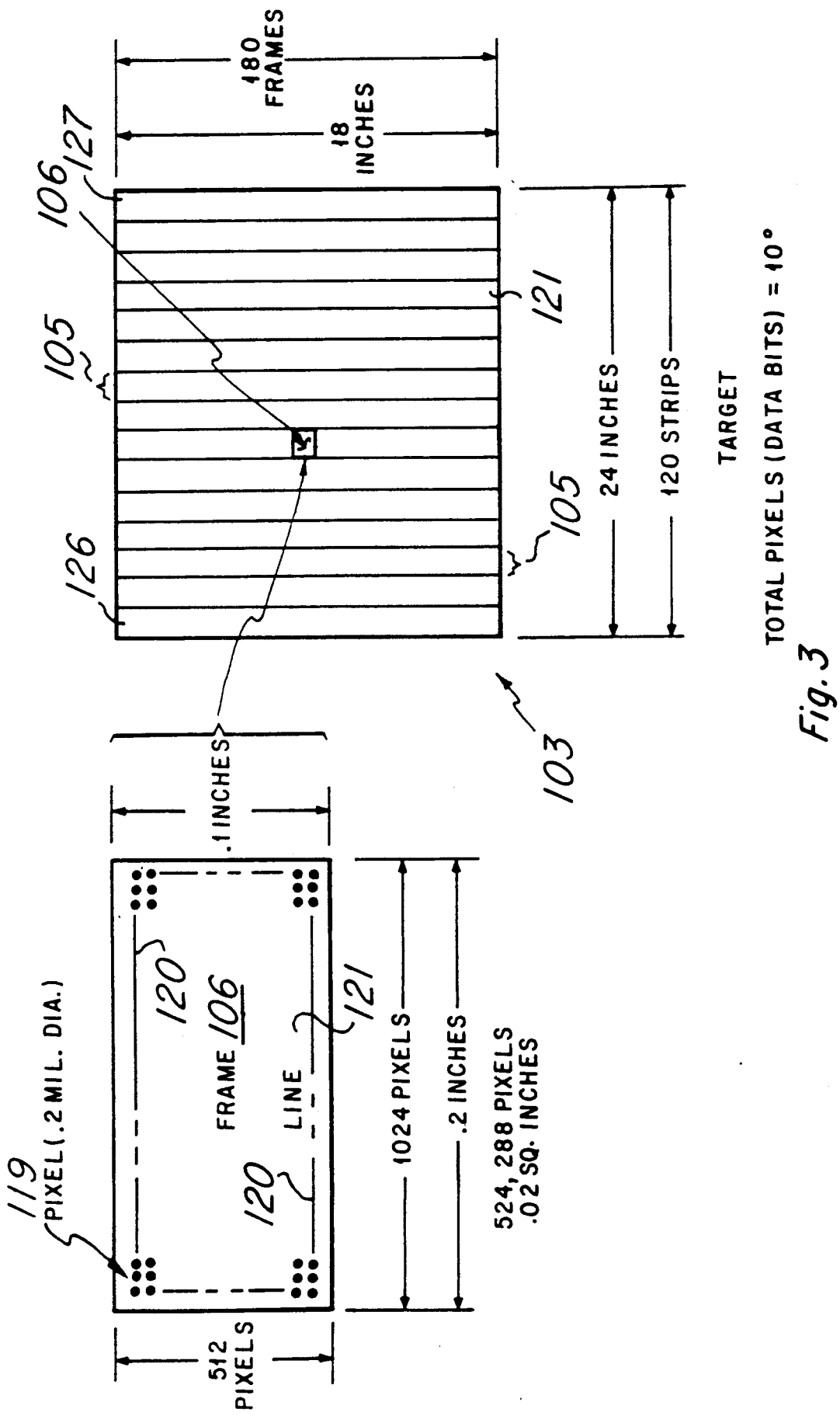
FIG. 3 is a plan view of an 18×24 inch printed wiring board target having photoresist on its upper face, with an expanded view of a frame.

As seen in FIGS. 1, 2 and 3, the target surface 121 is treated by pattern writer system 50 as being partitioned into a plurality of contiguous strips 105 of equal width W in the X direction. The sum of the individual widths W equals the width of the target 103 in the X direction. The height H of each strip 105 is the height of the target 103 in the Y direction. Each strip 105 is treated by pattern writer system 50 as being partitioned vertically into a plurality of contiguous frames 106. Each frame is of height FH in the Y direction, and the sum of the individual frame heights in a strip equals the height H of the target 103.

Each frame 106 is treated by pattern writer system 50 as having its area partitioned into a matrix of contiguous, equal diameter, circular pixels 119, as shown in FIG. 3. Preferably, the pixels 119 intersect with adjacent pixels at at least one point. The pixels 119 illustrated in FIG. 3 are not shown as touching one another for clarity of illustration, although, preferably adjacent pixels would touch each other. A geometrical shape which is to be written in a frame 106 on surface 121 will be written by exposing with laser beam 104 each pixel enclosed within the boundary of the geometrical shape. Pixels not contained within the boundaries of the geometrical shape will not be exposed to the laser beam 104. That is, laser beam 104 will be turned on by electro-optical modulator 101 only at those pixels contained within the boundary of the geometrical shape.

The power distribution of a laser beam striking surface 121 is approximately Gaussian, with the peak at the center of the area on 121 illuminated by the laser beam 104. The diameter of a pixel is approximately the diameter of the half power circle centered on the power peak. That is, approximately one half the power delivered by the laser beam to the surface 121, falls within the pixel. The photoresists used with this invention become exposed by those portions of the incident laser beam 104 which have sufficient energy to fall within the half power circle. It is evident that where adjacent pixels touch only at one or a few points, there will be portions of the surface 121 which do not lie within any pixels. However, these areas can still be made to have sufficient laser energy fall upon them to expose the photoresist there.

This can be understood by considering two adjacent pixels which touch only at one point. If each pixel is in turn illuminated by laser beam 104 by turning on the beam only when it will strike one of the pixels, it is evident that half the power being delivered to a pixel will fall outside the borders of the illuminated pixel. The areas between the two pixels but within neither pixel will receive some laser light when the first pixel is illuminated and then again when the second pixel is illuminated. Thus, the energy delivered from the sum of the two exposures will be sufficient to expose most of the areas lying between but not in adjacent pixels. This feature means that geometrical shapes on surface 121 can be made to contain negligibly few or no granularities. That is, given a geometrical shape within whose boundaries all pixels have been illuminated, all of the areas lying within the boundaries will receive enough incident laser light to expose substantially all of the photoresist within those boundaries. This is true even for geometrical shapes which lie in more than one adjacent frame and/or in more than one adjacent strip. There is no more distance between adjacent pixels when those pixels lie in different frames or strips than is the case with adjacent pixels lying in the same frame.

Figure 4:
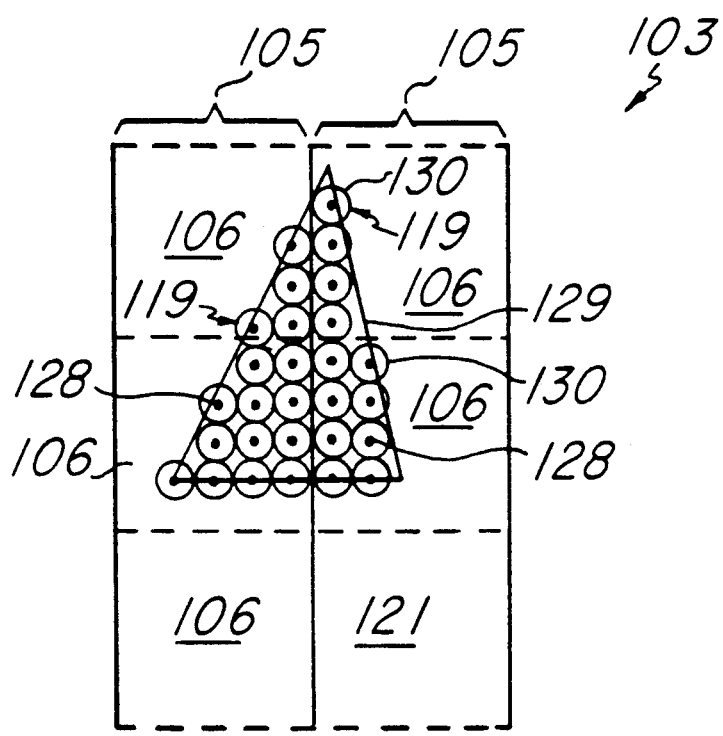
FIG. 4 is a plan view of a target with illuminated pixels shown for producing a triangle, also shown.

FIG. 4 shows which pixels 119 are illuminated in order to write a triangular shape 129 on photosensitive surface 121. The illuminated pixels are shown as half-power circles 130 which touch adjacent pixels at a single point on their half-power circles 130. Adjacent pixels are defined as being pixels which are next to each other either in the same row or same column of the matrix of pixels. A pixel is illuminated by laser beam 104 if the pixel center 128 falls within the boundary of the desired geometrical shape, in this case, triangle 129. It can be seen that the aggregate of the illuminated pixels does not form a perfectly shaped triangle when viewed from a perspective which is magnified to the extent of FIG. 4. However, geometries are rarely as small with respect to the size of an individual pixel as is shown in FIG. 4, thus, the irregularities inherent in forming a shape from constituent pixels are very small in size with respect to the size of the desired geometrical shape. In the example of FIG. 4, the pixel diameters could be reduced in size and the pixel density thereby increased so that the pattern of illuminated pixels more closely matches the desired triangle shape 129. In fact, for writing integrated circuit patterns directly on semiconductor wafers, the diameter of the half-power circle is reduced in size to become 0.5 micron. This is an order of magnitude smaller than the half-power circle size of 0.2 Mil (0.2 Mil=5.08 micron).

The target illustrated in FIG. 3 is a printed wiring board target 103 with a photoresist surface 121. The board has a height of eighteen inches and a width of 24 inches, thereby illustrating the large size printed wiring board on whose surface 121 the invention is capable of writing circuit geometries. In this example, the pixel 119 size is 0.2 Mil in diameter (0.0002 inches). Each strip 105 is 1024 pixels wide, which is also the width of each frame 106, and each frame is 512 pixels high. The pixels 119 are arranged in rows and columns. Preferably, adjacent rows and adjacent columns have a single common spacing distance so that the distance between two adjacent pixels 119 in a row is the same as the distance between two adjacent pixels 119 in a column. The illustrated frame has a height of approximately 0.1 inches and a width of approximately 0.2 inches. There are 120 strips (not all shown) across the width of the target and 180 frames (not all shown) along the height of the target 103. Each frame has 524,288 pixels, and there are on the order of ten to the ninth pixels for the entire target 103.

As illustrated in FIG. 1 and FIG. 2, laser beam 104 sweeps out lines 120 or rows of pixels from left to right across the width of a strip 105. The chirp deflector 102 deflects the laser beam 123 incident upon it and causes the emerging laser beam 104 to sweep through an angle subtended by the width W of the strip being written to. As discussed more fully in conjunction with FIG. 5, the angular sweep speed is a function of the velocity of a series of acoustic waves propagating transversely through the chirp deflector 102. The sweep speed is highly linear due to the relative constancy of the velocity of the acoustic waves as they travel the length of the chirp deflector 102. As the acoustic waves travel through the chirp deflector 102, the electro-optical modulator 101 allows the laser beam 123 to emerge and enter the chirp deflector when the angular deflection produced by the chirp deflector is such that the deflected laser beam 104 will strike a pixel whose center lies within the boundaries of the desired geometrical figure. The electro-optical modulator blocks laser beam 123 so that no laser beam 104 is emitted when the angle of deflection would otherwise cause laser beam 104 to strike a pixel which should not be illuminated. A pixel will not be illuminated when its pixel center 128 lies outside of the boundaries of the desired geometrical shape, such as the triangle 129 of FIG. 4.

The geometrical patterns which are to be produced on the photosensitive surface 121 of target 103 are produced by illuminating each pixel contained within the boundaries of the desired geometrical patterns. Such structures as circuit connections on the face of a printed wiring board can be constructed geometrically by partitioning the overall geometrical shape of the circuit structures into a plurality of constituent, contiguous polygons. Each such constituent polygon is contained within a single frame 106. Thus, a geometrical feature which is large enough, as most practical features will be, to extend over a plurality of frames, will consist of polygons from all the frames 106 into which the feature extends.

Each constituent polygon in a frame 106 will have the pixels contained within the boundary of that polygon, illuminated by the laser beam 104 by raster scanning the area in the frame with modulated laser beam 104. In the embodiments of the invention shown, the pixels in a frame are arranged into 512 rows of 1024 pixels in each row. A frame is raster scanned by beginning at the left end of the uppermost row in the frame and sweeping modulated laser beam 104 across the full width of the frame 106. Thus, each of the 1024 pixels in the top row will be passed over by the modulated laser beam. The modulated laser beam 104 is turned on when the beam is over a pixel to be illuminated, is turned off between pixels, and is off when over pixels which are to receive no illumination because their centers 128 lie outside the polygon(s) in the frame. That is to say, the modulated laser beam 104 is turned on only when the raster scan position is such that the laser beam will strike a pixel that lies within one of the polygon(s) within the frame. While the top row is being scanned, the stage 118 is continuously moving in the negative Y direction, carrying target 103 with it. After the top row has been scanned, the stage 118 is allowed to move in the negative Y direction the distance of one pixel position, and the second row of 1024 pixels is scanned by modulated laser beam 104. Again, the stage continues to move in the negative Y direction while the second row is being scanned. This process continues until all 512 rows of pixels have been scanned by the modulated laser beam 104. The stage 118 continuously moves during the entire 512 raster scans of the frame, so that there is a slight tilt downward to the right of each of the 512 rows. The pixel scan rate is sufficiently fast (up to 100 MHZ) that for all practical purposes a scan of a line happens instantaneously. The speed of the stage in the negative Y direction is slow relative to the scan speed, thus, the slope of the rows is almost imperceptible and causes no significant distortion of the patterns produced on surface 121.

A target 103 is scanned, strip 105 at a time, from left to right. A strip is scanned frame 106 at a time from top to bottom, although, strips can be scanned in serpentine fashion. That is, after a strip 105 has been scanned from top to bottom, the next strip 105 to the right can be scanned from bottom to top. This saves some run time since the stage 118 does not have to move in the positive Y direction back to the topmost frame 106 in the next strip to the right before beginning to scan that strip. As discussed above, frames 106 are scanned row at a time from top to bottom, except when operating in the serpentine mode, in which case frames are scanned row at a time from bottom to top. Rows are scanned one pixel at a time from left to right. As seen in FIG. 2, raster scanning of target 103 begins in the leftmost strip 126 in the uppermost or top frame. The uppermost frame is scanned one row at at time beginning with the topmost row. The illustrated topmost frame has fad four rows raster scanned and the fifth row is partially completed.

Raster scanning of a row 120 is accomplished by transmitting acoustic pulses into chirp deflector 102 which causes laser beam 104 to scan the row from left to right for the with of the frame 106. The chirp deflector 102 produces no deflection of the laser beam 104 in the Y direction. This is produced by the motion of the stage 118 in the negative Y direction, which shifts the target 103 to the Y position of the next row 120. After a strip 105 has been raster scanned, the next strip to the right is raster scanned after first moving the stage 118 in the negative X direction for a distance equal to the width of strip 105. The target 103 will have been completely raster scanned after strip 127 has been raster scanned.

X and Y Scan Compensation

The stage 118 and stage controller 111, shown in FIG. 1, are available from the Anorad Corporation of Hauppauge, N.Y. The stage 118 preferably is solid granite four inches thick and more than eighteen inches high and twenty-four inches wide. For writing patterns on semiconductor wafers or smaller printed wiring boards, the surface dimensions of the stage 118 can be less than eighteen inches by twenty-four inches. The stage moves on air bearings on a granite base of large dimensions. Granite is used for the stage and base because it can be machined to have very precise flat surfaces and it is a very stable material with respect to its thermal expansion characteristics. In addition, the large mass of the granite base dampens vibrations transmitted from the surrounding environment. The Stage controller includes X stage drive 107 and Y stage drive 108. Not indicated in FIG. 1 are the drives for theta and Z axis movement of the stage. X, Y and Z axis glass scale encoders are included for providing stage position information having a resolution of less than one micron. For more accuracy, plane mirror laser interferometers can be used rather than glass scale encoders to provide stage position information. In situations where extreme accuracy is unnecessary, such as creating artwork or exposing photoresist directly on large size printed wiring boards, glass scale encoders are preferable due to faster speed of operation and lower cost. Depending on the speed, cost and accuracy requirements, other ways of obtaining instantaneous stage 118 position information can be used as well. For example, resolvers, magnetosyns, rotary encoders or grating projection techniques are possibilities.

Interferometer position information can be dynamically corrected for temperature, humidity and barometric pressure. Corrected interferometer or glass scale encoder Y position data may be used to trigger each row 120 scan, thus reducing dependency on constant velocity servo performance. This ensures correct and equal spacing between rows 120 on the surface 121 of target 103. The X axis interferometer or glass scale encoder position information may be used to correct the individual row scan start time delay. This corrects for X direction positioning error, and ensures that the pixels which should have the same X address, form straight columns. Since the row 120 laser scan is very fast with respect to the stage 118 motion in the Y direction, the X direction positioning correction has no significant effect on the Y direction positioning of the row. This can be understood by considering that for a 1024 written pixel per row scan system the row scan in the X direction is more than one thousand times faster than the Y direction mechanical stage speed. Stage controller 111 receives stage movement commands from bit-slice electronics 109.

FIG. 5 is an expanded block diagram of the laser raster scan optical system, showing more detail than is shown in FIG. 1. Argon ion laser 100 emits an unmodulated output beam which is directed into electro-optical modulator 101 by mirrors 131 and 132. Laser 100 may be a krypton ion gas laser. Selection is based on the required writing wavelength. For most liquid integrated circuit photoresists, an argon ion laser 100 operated at 457.9 nanometers wavelength is the preferred choice. Because of its operation at lower plasma current than a krypton ion laser at 413.1 nanometers, less ultraviolet is generated within the laser plasma tube. Since high intensity ultraviolet output within the plasma tube degrades the tube windows, longer operating life is expected at the argon 457.9 nanometer wavelength of operation. For those applications using photoresists that require the shorter wavelength light for proper exposure, a krypton laser may be used.

Electro-optical modulator 101 receives a serial pixel bit stream 110 from bit-slice electronics 109 and modulates the laser beam, as discussed above.

The modulated laser beam is reduced in power by attenuator 112. Attenuator 112 can be a half-silvered mirror which reflects a portion of the laser beam, while allowing the remainder of the beam to pass through. Preferably, however, attenuator 112 is an electrically controlled variable attenuator. The attenautor 112 is used to select the power level required for writing photographic emulsion or different photoresists. The power level is usually selected so that photographic exposure of the emulsion or photoresist takes place within the half-power circle 130 of the incident laser beam 104, but does not take place outside the half-power circle.

The laser beam which emerges from the attenuator is directed to tracker 113 by mirror or prism 133. Tracker 113 is used to provide coarse aiming of the laser beam to improve the optical efficiency of the chirp deflector 102. The laser beam which is input to the tracker 113 emerges from the tracker as a beam which sweeps in time through an angle on the order of the angle subtended by the aperture of chirp deflector 102. Tracker 113 is an acousto-optical Bragg cell which operates in the flooded aperture mode. An RF signal is input to one end of the Bragg cell and it travels transversely to the optical axis. The input RF is ramped up in frequency so that the angle of deflection of the laser beam emerging from the tracker is dependent upon the frequency of the RF. The tracking speed of the emergent laser beam is as linear as is the input RF ramp. On the order of 5% linearity has been found to be sufficient to function as a tracker. The input RF is ramped up between two fixed frequencies. When the high end of the ramp is reached, the input RF is again lowered to the lower of the two fixed frequencies and again ramped up. The RF input is in fact a saw-tooth wave of a wavelength on the order of the size of the optical aperture of the Bragg cell. The sweep frequency of the laser beam output from the tracker is, in fact, the frequency of the saw-tooth wave. The purpose of the tracker will be discussed below in conjunction with the chirp deflector 102.

The swept laser beam from the tracker 113 is directed by prism or mirror 134 into beam shaping lenses 114 and anamorphic beam expander 115. The beam forming lenses and anamorphic beam expander convert the narrow angle scan from the tracker into the wider scan angle required by chirp deflector 102. Also, the cross-sectional shape of the tracking laser beam is changed to the elliptical shape which is required for best chirp deflector 102 efficiency with minimum edge effects. Anamorphic beam expanders such as the one used in the invention are discussed in the article: In-line Anamorphic Beam Expanders, Applied Optics, Vol. 21, No. 15, Page 2861, which is hereby incorporated by reference.

The chirp deflector 102 provides the high resolution stable linear laser scan required. The scan is inherently linear depending upon the uniformity of the acoustic pulse in the solid crystal block of high purity optical material in the deflector. Thus, no scan linearity corrections are required, resulting in very stable precision geometry positioning on the surface 121 of target 103. The chirp deflector 102 focuses the output scanning laser beam in the X direction, i.e., the direction of scan. The chirp deflector differs from a Bragg cell in that the linearity of the output scan depends only on the constancy of the speed of acoustical energy in the optical medium of the deflector, while linearity of the Bragg cell depends upon the linearity of the ramp of the input RF acoustic wave.

Chirp deflector 102 deflects the input laser beam by diffraction. A train of acoustic pulses of RF is input to the optical medium of the deflector and travel transversely to the optical axis. Each acoustic pulse or chirp is a short section of an acoustic compression wave of RF and is linearly ramped from a fixed lower frequency to a fixed higher frequency. The more nearly linear the ramp is, the more nearly focused the scanning output laser beam will be. As one acoustic pulse leaves the optical medium of the chirp deflector, another enters it. Between adjacent pulses the amplitude of acoustical energy is zero. The tracking laser beam which is input to the chirp deflector scans the aperture of the deflector at a scan rate matched to the acoustic pulses in the chirp deflector 102. That is, the tracking laser beam will strike that portion on the optical medium where the acoustic pulse is at the time, and will track the pulse across the aperture of the deflector. When a new pulse enters the deflector, the tracking laser beam begins a new sweep or scan and tracks the new pulse. This mode of operating a chirp deflector commonly is called the scanning mode, in contradistinction to the flooded mode.

Chirp deflectors and tracking acousto-optical deflectors are discussed in the following articles and one U.S. Patent and are hereby incorporated by reference:

1. U.S. Pat. No. 3,851,951;
2. Acousto-optic Laser Recording, Optical Engineering, January/February 1981, Vol. 20, No. 1, Pages 143–149;
3. Acousto-optic Laser Scanning, SPIE, Vol. 169, Laser Printing (1979), Pages 56–59; and
4. Acousto-optic Laser Recording, SPIE, Vol. 175, Airborne Reconnaissance IV (1979), Pages 111–123.

The scanning laser beam output from the chirp deflector has been focused in the X direction by chirp deflector 102, and is then focused in the orthogonal, i.e., Y, direction by cylindrical lens 116.

Mirror 135 directs the focused, scanning laser beam through objective lens assembly 117 where final focus is achieved prior to striking the photosensitive surface 121 of target 103.

Bit-slice electronics 109, shown in FIG. 1, includes a plurality of bit-slice processors for real-time database expansion row 120 by row 120 into a bit-map of the geometrical patterns to be written onto photosensitive surface 121 of target 103. The bit-map is output row by row 120 as serial pixel bit stream 110 to the electro-optical modulator 101. Each bit which is output corresponds to a predetermined pixel position on surface 121.

The host computer 3 is a Texas Instruments 990/12 system, and is used as an interface between a human operator and the rest of the pattern writer system 50.

THE ELECTRONICS

Figure 6A:
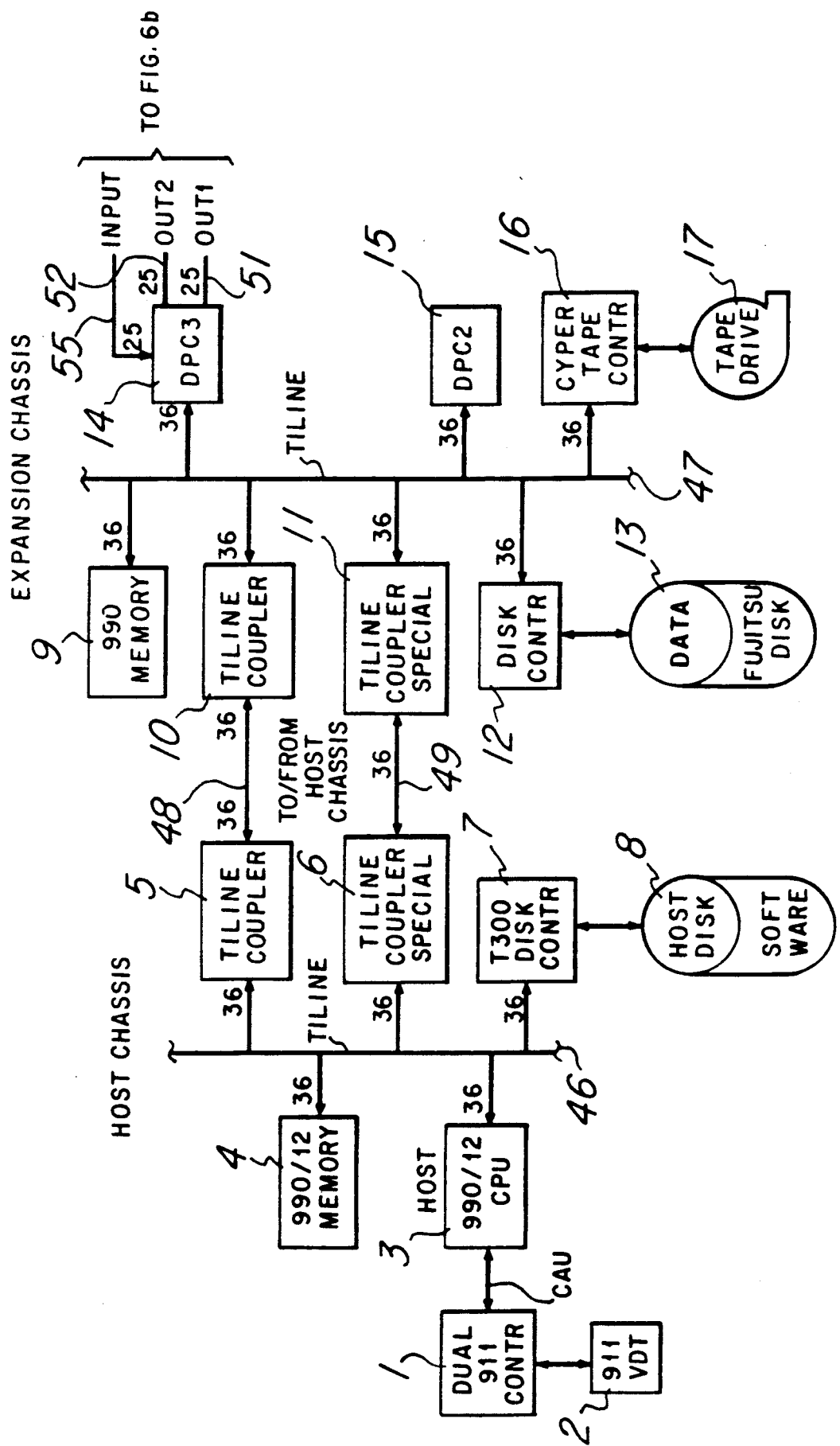
FIG. 6 is a block diagram of a laser pattern writer.
Figure 6B:
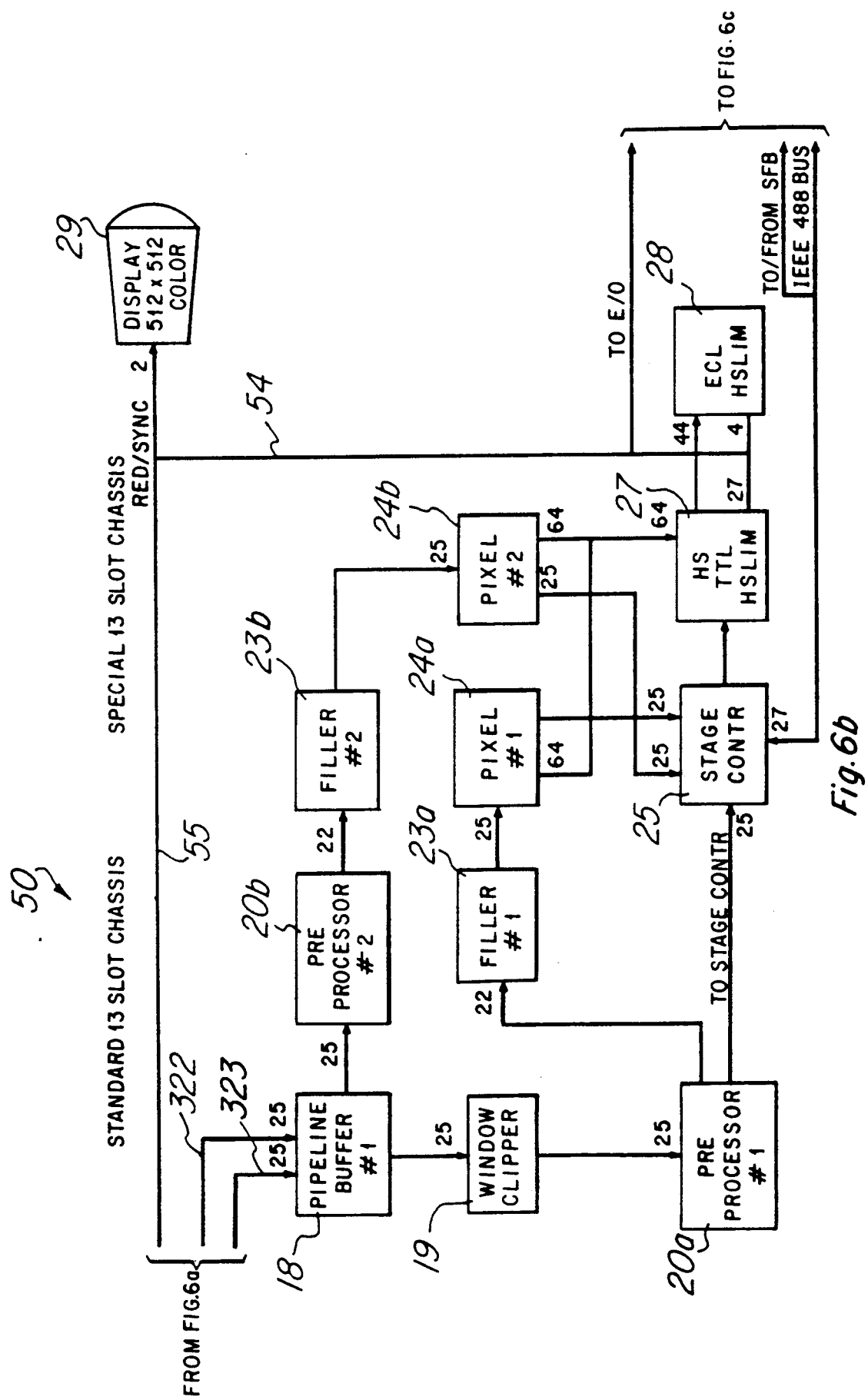
Figure 6C:
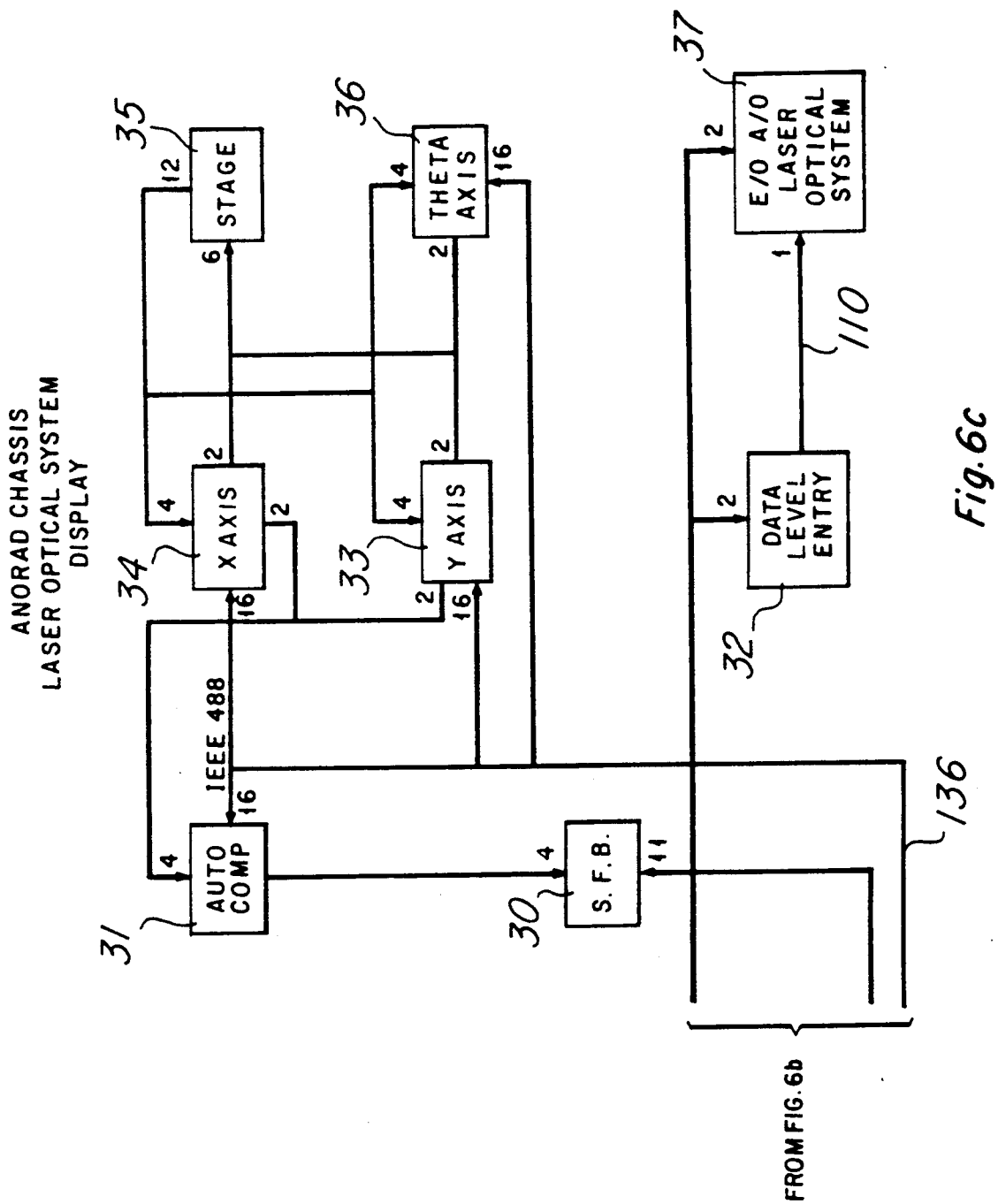

FIG. 6 is a block diagram of one of the embodiments of the photolithographic laser writer. To begin writing on light sensitive material, a human operator communicates to the system via a keyboard 1 and video display terminal 2, which are connected to the host computer 3. The host computer can be selected from many possible computers, but preferably is a Texas Instruments 990/12 CPU. which executes the operating system for interfacing the writer to the human operator. The host 3 interrogates operator inputs from keyboard 1 and passes control information to the bit-slice processors DPC2 15 and DPC3 14. The host 3 also locates the beginning of the database.

The host 3 communicates to the host disk controller 7 and host magnetic storage disk 8 via TILINE 36 bit wide chassis bus 46. The disk 8 is where the host operating system is stored and offloaded in order for the operating system to boot up on the host computer 3. Dynamic random access memory is provided for the host 3 to use at host memory 4. The host also communicates with host memory 4 over the chassis bus 46. Preferably the host 3, memory 4, host disk controller 7 and chassis bus 46 are contained within a single chassis, although this is not necessary for the proper functioning of the invention.

The host 3 is in communication with TILINE 36 bit wide bus 47 by way of bus buffers 5 and 6, 36 bit buses 48 and 49, and bus buffers 10 and 11. Bus buffer 5 is connected to bus buffer 10 through bus 48, and bus buffer 6 is connected to bus buffer 11 through bus 49. Commands and data are passed between the host 3 and the bit slice processors DPC2 and DPC3 through host memory 4. The host 3 writes commands either to DPC2 15 or DPC3 14 by first writing the command to host memory at a determined address. The host then addresses DPC2 or DPC3 directly to pass the command's address in host memory 4 and the length of the command address to the addressed bit-slice processor. The command itself, residing in host memory 4, is then read by the addressed bit-slice processor over bus 48. Subsequently, the command is acted upon by the addressed bit-slice processor, and any data resulting from the execution of the command is then written over bus 48 and stored at a predetermined memory location in host memory 4. An interrupt is then generated by the addressed bit-slice processor, and is written to the host 3 over bus 48 or bus 49. Bus 49 is used solely for passing interrupts from the bit slice processors to the host, and from the data disk controller 12 and the tape controller 16 to the host 3.

The writer system 50 database is stored on tape at tape drive 17. The database comprises sixteen bit word, coded descriptions of the polygons necessary to describe the geometries which are to be written on a photosensitive surface. The database is organized into a number of non-overlapping contiguous strips and each strip is grouped into a number of non-overlapping contiguous frames. The strips and frames of the database correspond to the physical strips and frames, shown in FIGS. 1–4, ultimately written on a photosensitive surface. Preparatory to writing on the photosensitive surface, bit slice processor DPC2 15 reads the coded descriptions of the polygons from tape drive 17, recodes the descriptions into a turnpoint polygon representation, and stores the recoded descriptions of the geometries onto data disk 13, as sixteen bit words, DPC2 writes control commands over bus 47 to tape drive controller 16 to effect the reading of the tape 17, and writes control commands over bus 47 to data disk controller 12 to effect the storage on the data disk 13 of the recoded polygon descriptions. During recoding, the polygon description data is transferred via bus 47 from the tape 17 to DPC2 15, where the recoding process takes place. The recoded descriptions are then transferred over bus 47 to data disk 13. The entire database on tape 17 is recoded and transferred to data disk 13 before any further processing is done on the data now residing on data disk 13, and may be done at any time prior to beginning the process of pattern writing. This allows databases for a number of different circuits to be recoded and stored on data disk 13. Thus, the runtime of the writing process can be shortened and multiple copies of the same circuit can be written on printed wiring boards, reticles or photomasks, without having to re-do the process of recoding and transferring the database from tape 17 to data disk 13. In the case of integrated circuit patterns on multiple dies of a single wafer, the database describes the geometry of the entire wafer, and thus the process of recoding and transfer of data from tape 17 to data disk 13 need only be done once for a wafer, even where more than one kind of circuit is to be written on the same wafer.

Preferably, however, a strip buffer may be used which would, on a real-time basis, store the bit-map for an entire strip which has a height approximately equal to the wafer height. With this embodiment, separate databases would be maintained only for each unique integrated circuit pattern. Thus, for a wafer in which all the IC bars, i.e., IC chips, are to have the same integrated circuit pattern applied to each, only one integrated circuit pattern database need be stored on tape or disk, and subsequently be expanded in the pipelines. The bit map for one IC bar simply is replicated in the strip buffer for as many IC bars as the wafer is high.

Further processing of the data now residing on the data disk 13 takes place in realtime during the process of writing patterns on a photosensitive surface. DPC2 and DPC3 are each implemented with a 16 bit, Texas Instruments SN74S481 bit-slice processor for maximum speed, however, a commercially available microprocessor such as a Motorola 68000, a Motorola 68020 or an Intel 80286 could be used instead.

DPC memory 9 is dynamic random access memory for use by DPC2 15 and DPC3 14, and is accessed by DPC2 and DPC3 over bus 47.

Figure 38A:
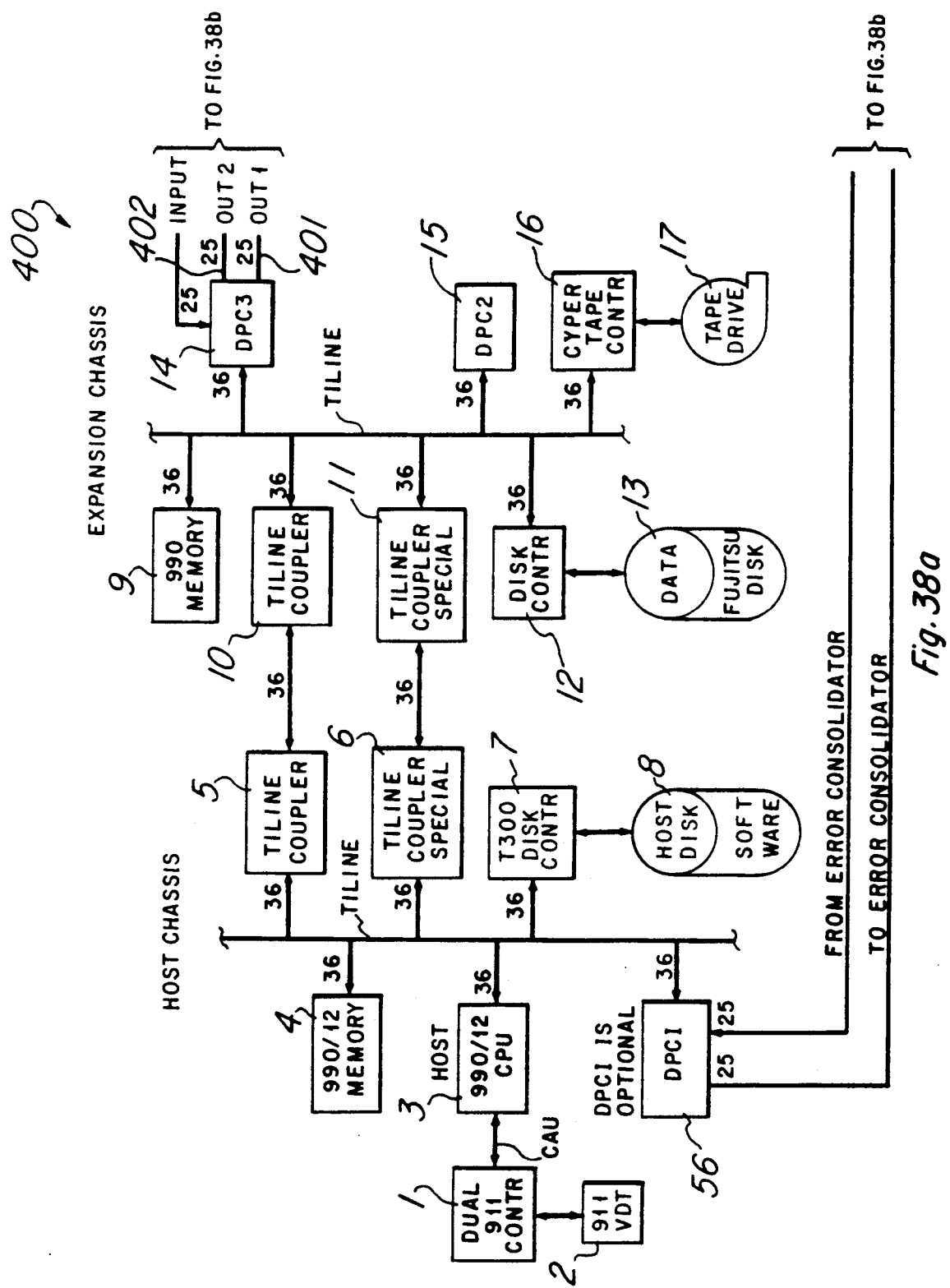
FIG. 38 is a block diagram of a pattern inspector system which also has the capability of operating in a writer mode.
Figure 38B:
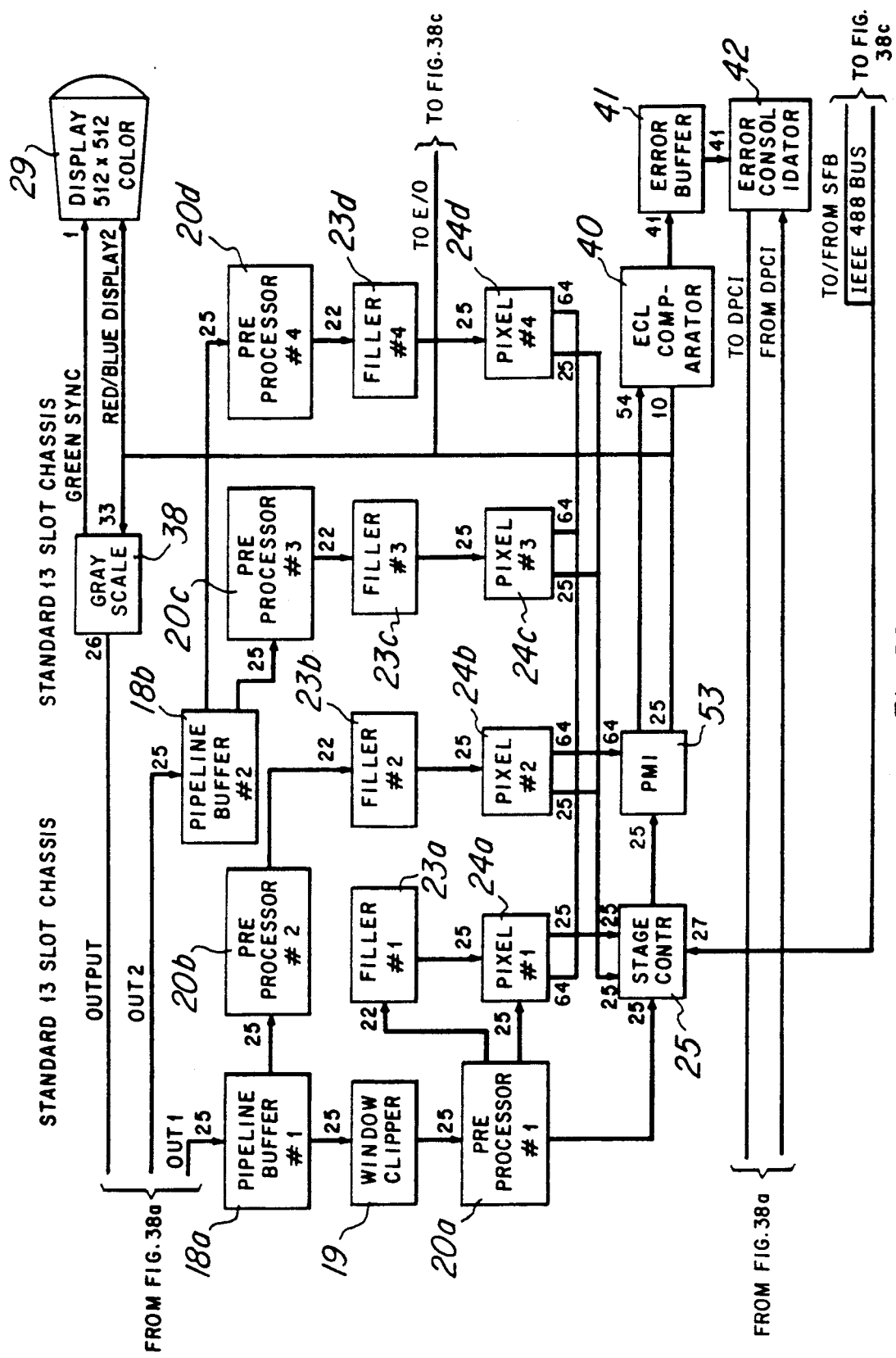
Figure 38C:
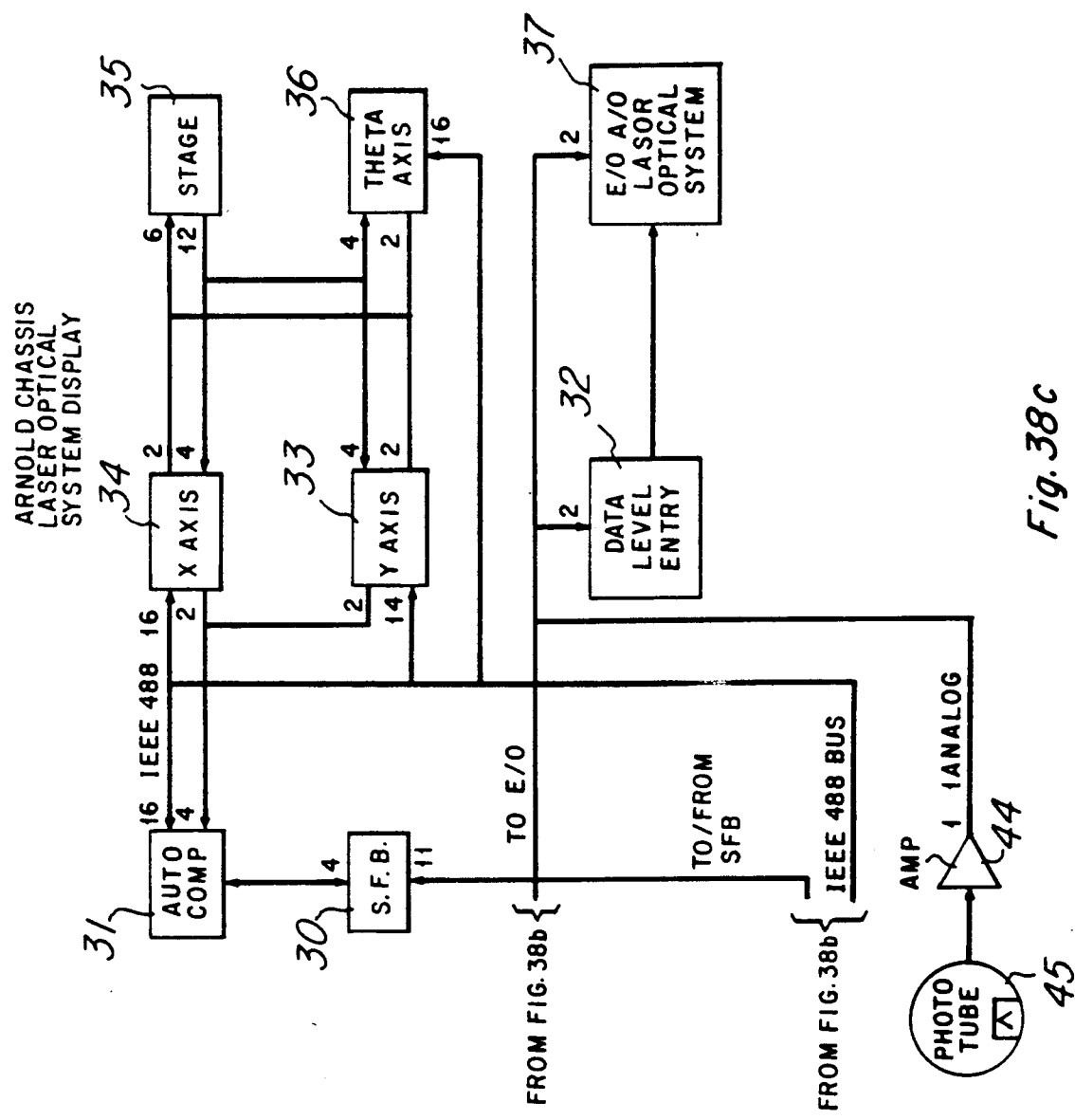

The sixteen bit word, turnpoint polygon data stored on data disk 13 is read by DPC3 14 over bus 47, and is recoded into 25 bit word turnpoint polygon data, with the addition of 25 bit command words interspersed throughout the data. DPC3 has an output out1 at 51 to a first pipeline, and a second output out2 at 52 to a second pipeline. The two pipelines operate in parallel downstream from DPC3 14. DPC3 sends the first frame of recoded, 25 bit data down the first pipeline via out1 51, and sends the second frame of recoded, 25 bit data down the second pipeline via out2 52. Subsequent frames continue to be sent down alternate pipelines, so that contiguous frames of data are never sent down the same pipeline. This increases the speed of processing the data downstream of DPC3 since contiguous frames of data are processed in parallel downstream, in different pipelines. The processing of any single frame of data that takes place at DPC3 is much faster than the processing of that frame taking place downstream of DPC3, thus, by multiple pipelines, the effective speed of downstream data processing is increased. FIG. 6 illustrates an embodiment of the invention with two pipelines, while FIG. 38 illustrates an embodiment of the invention having four pipelines. The invention also comprehends having other numbers of pipelines not illustrated. The number of pipelines desired is determined by the speed of operation desired, and by the relative speeds of the processing taking place at DPC3 and downstream from DPC3. The relative speeds are influenced by the speed of the circuit components used to construct the writer system 50, and by the algorithms being executed by the various processors in the system 50.

Pipeline buffer 18 includes two 4K×25 bit FIFOs, i.e., first-in-first-out memory, which provides memory buffering for interfacing the faster DPC3 with the slower downstream processing.

Window clipper 19 can be used to view a pictorial representation of segments of the database on color display 29. Since the display 29 can show only half a physical frame 106, the window clipper must transform multiple frames of data into a single frame of data. This must be done where the area which a human operator wishes to view straddles parts of more than one frame of data. The window clipper 19 includes a 24 bit bit-slice processor which executes a window clipping algorithm. Normally, however, the display is not used during pattern writing on photosensitive material and the 25 bit wide data is simply passed through the window clipper without alteration.

Preprocessor1 20A and preprocessor2 20B each include a 16 bit bit-slice micro-coded processor which recodes the 25 bit word, turnpoint polygon data into 22 bit words in which the upper 6 bits is command information and the lower 16 bits is data. The turnpoint polygons are recoded into left and right vectors. The 16 bit data includes the origin of each vector, the vector length and the direction of the vector. The two preprocessors are each a part of a different one of the two pipelines.

The 22-bit-word-data output from preprocessor1 20A is written to filler module1 23A, and the 22-bit-word-data output from preprocessor20B is written to filler module2 23B. Filler module1 and filler module2 each recode the 22-bit-word-data from preprocessor1 and preprocessor2, respectively, into 25-bit-word-data and output it to pixel memory module1 24A and pixel memory module2 24B, respectively. Each 25 bit word uses the upper 5 bits as a command, the next 10 bits refers to the Y-address of a line of data, and the least significant 10 bits refers to the starting X-address of a group of pixels to be turned on. The size of the group of pixels to be turned on is specified in the upper 5 bit command word. Each pixel which is turned on corresponds to an X-Y location on the photosensitive material which is to be exposed to laser light. A pixel is the smallest unit of area on the photosensitive surface which can be illuminated by the laser beam. Its diameter is the diameter of the laser beam at the photosensitive surface. The meaning of the X and Y addresses and of the pixels is more fully discussed in conjunction with FIGS. 3 & 4. A Texas Instruments SN74S481 bit-slice processor is included as part of each filler and is microcoded to do the recoding.

The 25-bit-word-data output to pixel memory module1 24A and pixel memory module2 24B by filler module1 23A and filler module2 23B. respectively, is recoded by each pixel memory module into 64 bit words. Each bit position of a 64 bit word corresponds to a pixel and to an X-Y position on a photosensitive surface. If a bit position is a one, the pixel is to be turned on. That is, the X-Y position corresponding to that bit position is to have the laser beam shined on it. If the bit position is a zero, the pixel is to be turned off, and no light will be shined on the corresponding X-Y position. Each pixel memory module includes a SN74LS25117 arithmetic logic unit microcoded to do the recoding of the incoming data into the 64-bit-word data, which then is sent to the high-speed laser interface module 27.

High-speed laser interface module 27 selects the output from pixel memory module1 24A for the first frame's worth of 64-bit-word data, and then selects the output from pixel memory module2 24B for the second frame's worth of 64-bit-word data. For subsequent frames of data, the outputs of pixel memory module1 24A and pixel memory module2 24B continue to be alternately selected, frame-at-a-time, for input to high-speed laser interface module 27. Thus, the data generated from the database leaves the two separate pipelines and is recombined in the high-speed laser interface module 27.

The high-speed laser interface module 27 includes a counter which counts a frame's worth of bits in order to determine when an entire frame of data has been read in. This is possible since each bit which is output from the pixel memory modules represents one pixel, and the total number of pixels in a frame is fixed at 1024 * 512 = 524,288 for this embodiment of the invention. Therefore, the high-speed laser interface module 27 reads the first 524,288 bits of data from pixel memory module1 24A, reads the next 524,288 bits from pixel memory module2 24B, reads the third 524,288 bits from pixel memory module1 24A, and so on, continuing to alternate between pixel memory modules for each subsequent frame of data. It is understood that other frame sizes could be used without departing from the invention.

The high-speed laser interface module 27 also includes a memory for receiving the 64-bit-word data input to the module. Each 64 bit word is divided into four contiguous groups of 16 bits. The four groups are output one group at-a-time to ECL high-speed laser interface module 28. The four groups are output in descending order from most significant to least significant.

Each group of 16 bits input by the ECL high-speed laser interface module 28 is sent to a 16 bit shift register. There, the bits are shifted out one-at-a-time to form a serial stream of bits, output in descending order from most significant to least significant. Each bit position in the serial stream corresponds to the X-Y position of a pixel on the photosensitive surface upon which geometrical patterns are being written. The serial stream of bits is output to data level shifter 32, where the logic levels are shifted from ECL levels −1.6 volts and −0.8 volts, to +0.5 volts and −0.5 volts dc, respectively. From data level shifter 32, the serial pixel bit stream 110 is output to the laser electronic and optical system 37. The laser electronic and optical system includes electro-optical modulator 101 which inputs serial pixel bit stream 110 and modulates the laser beam 122 for writing geometrical patterns on the photosensitive surface 121.

High speed laser interface module 27 sends expanded database part data on data monitor path 54 to be displayed on color display 29 for review by the human operator. The operator can view what the ideal part on the database should look like at specific locations on an ideal target. As discussed previously, window clipper 19 combines data from multiple frames 106 when the area of the part to be viewed straddles more than one frame 106, and allows the data to be handled as if it came from a single frame. The data outside the viewing area of the display is clipped off.

High speed laser interface module 27 sends error code information back along data monitor path 54 and data return path 55 to DPC3 14. The error code information is generated by various modules in the pipelines and is used to ensure that the modules are functioning correctly. DPC3 relays the error information to the host CPU 3 which can take corrective actions, such as aborting the pattern writing process.

The X and Y axis blocks indicated at 34 and 33, respectively, include processor or microprocessor controls for the X and Y glass scale encoders (or laser interferometers), respectively. Also, X and Y direction stage 118 move commands are received at blocks 34 and 33, respectively, from stage controller 25. At block 36 theta axis table rotation commands are received from stage controller 25. The move commands are translated into control signals which are sent from blocks 33, 34 and 36 to stage block 35, where the motors responsible for moving the stage 118 are actuated by the signals.

Stage block 35 also includes the X and Y glass scale encoders or, alternatively, the X and Y laser interferometers. Stage 118 position data is sent from the glass scale encoders to the X and Y axis blocks where it is sent to autocompensator 31. The autocompensator performs scaling operations on X and Y position pulses received from the glass scale encoders or laser interferometers, as the case may be, to compensate for temperature and pressure environmental variations. Compensated pulses are transmitted to the smoothing filter 30 and the stage controller 25. Compensation is based upon values received from the 990/12 host computer 3 via IEEE-488 bus 136. The compensation values are supplied in an order specified by the autocompensator firmware. The X and Y position pulses do not give absolute position information but must be counted by stage controller 25 to determine the absolute position of the stage 118. Pulse separation corresponds to a predetermined physical travel distance for the stage 118, so the sum of all the pulses received since the stage was at rest, is the total distance travelled by the stage. The autocompensator includes 4 bit-slice arithmetic logic units, but could be implemented with a microprocessor instead.

The autocompensator 31 converts the uncorrected position pulse input from either a glass scale stage 35 position encoder or a fast pulse encoder in a laser interferometer system into pulses whose space corresponds to the motion of the stage 35 in the mechanical units of choice. Specifically, laser interferometers are used to measure stage travel in units of wavelength of the measuring laser light.

When the measuring path is not in a vacuum, the wavelength of the measuring light is dependent upon the refractive index of the medium, which in turn is dependent upon the temperature, humidity and barometric pressure of the medium. Since each row 120 of laser writing is triggered when the target 103 has moved one pixel or grid unit, a realtime stream of position pulses is required having a periodicity equal to the pixel or grid unit spacing. The conversion from wavelength units to pixel units or grid units is done by the autocompensator 31. This same form of compensation is applied when patterns are written that have a slightly different size than the reference database. This is important for writing sequentially built printed wiring boards, or any aligned multi-layer structure. This same dimensional compensation also is required for pattern inspection to achieve registration between the reference database and the target pattern being inspected. In such a case, the correction is based upon alignment marks included on the target 103. The autocompensator 31 scale factor is calculated to adjust the row scan units to coincide exactly with the alignment marks spacing.

The compensation is achieved by programmed pulse rate scaling. One implementation of programmed pulse rate scaling is by repeated addition or subtraction. In one form, this is done using an arithmetic accumulator having as many bits as the finest increment desired in the correction, i.e., if correction resolution of one part in 1024 is desired, then a ten bit adder is required. For each incoming position pulse, a constant is added to the accumulator for each positive direction pulse and the complement of the constant is added for each pulse in the negative direction. Overflow (carry out of the accumulator) is a positive direction output pulse and underflow is a negative direction output pulse. The constant to be added is calculated by dividing the number of output pulses by the number of input pulses, and multiplying the result by the maximum value that can be stored in the accumulator. The number of output pulses per input pulse cannot exceed one. This method produces smoother output if the units are scaled so that there are several input pulses for each output pulse.

The autocompensator 31 also performs fixed scale division on stage 118 position and direction of travel pulses from both the X and Y directions and performs a programmable pulse output rate scaling operation to compensate for environmental variations.

The autocompensator 31 receives X and Y position pulses corresponding to a one micron distance of stage 118 travel per pulse. The autocompensator transmits compensated 5 or 10 micron X and Y position pulses to the stage controller 25. That is, the autocompensator transmits one pulse for every 5 or 10 pulses received from the X and Y axis blocks 34 and 33. Whether 5 or 10 pulse resolution is used depends upon whether 5 micron or 10 micron spacing between pixel centers 128 is desired. Thus, the autocompensator scales the finer resolution X and Y position pulses originating with the glass scale encoders or the laser interferometers, to a resolution which is not so fine but is resolved in units of pixels.

Smoothing Filter

Accurate laser writing of individual pixels depends on accurately spacing rows 120 of pixels 119 in the Y direction, and accurately beginning the writing of each row 120 of pixels. This requires accurate information as to the X and Y position of the stage 118. Although glass scale encoders may be desirable for a particular application due to their speed, they can suffer from local inaccuracies in the sine wave that they output to the pulse generating electronics in blocks 34 and 33. These inaccuracies result in inaccurate time spacing between some of the pulses. Some of these inaccuracies result from artifacts in the grating uniformity on the glass scales of the glass scale encoders. These inaccuracies can result in unstable phase relationships between the quadrature outputs of the grating sensors. This can result in short range shifts in the indicated pulse position, which causes a short range shift in the X or Y position calculated by the stage controller 25. With a well made grating, cumulative or long term errors are very small or nonexistent. The short range error is reduced in severity by the smoothing filter 30.

Figure 7:
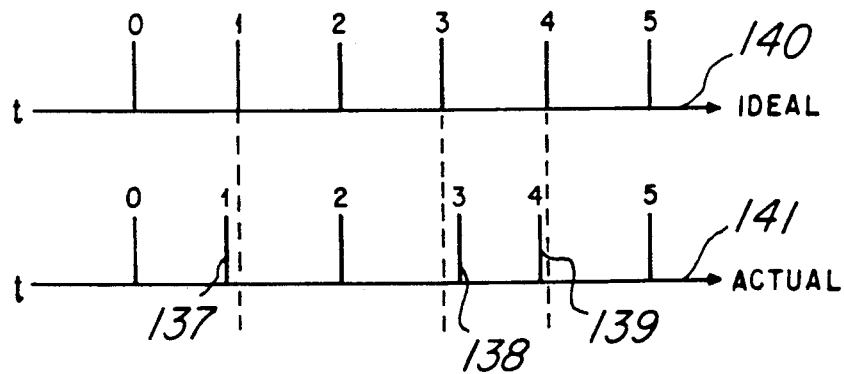
FIG. 7 is a diagram showing ideal and actual pulse trains from the autocompensator.

The smoothing filter 30 receives glass scale encoder generated X and Y position pulses and stage 118 travel direction information from the autocompensator 31. The position pulses received from the autocompensator are sporadic and not evenly spaced apart. This can be seen by referring to FIG. 7, which shows the actual pulse train 141 for either X or Y input by the smoothing filter 30 from the autocompensator 31. The actual pulse train 141 is shown for purposes of illustration and can represent either the X or Y position information. For purposes of this illustration, the stage 118 is assumed to be moving at constant speed, which it does most of the time with a high degree on consistency due to the inertia from the large granite mass of the stage. The ideal pulse train 140 represents what the pulse train from the autocompensator should look like when the stage is travelling at a constant speed. Pulses 137, 138 and 139 of the actual pulse train are shifted in time from where they should be if they are to represent accurately the true position of the stage 118. The smoothing filter 30 transforms the pulse train 140 representing the movement of a non-accelerating or non-decelerating stage into an output pulse train having constant spacing between pulses. The pulse train output from the smoothing filter 30 will have a constant pulse separation which is nearly the same as the separation of the ideal pulses.

The smoothing filter 30 averages the time lapsed between the output pulses of the autocompensator over a 16 pulse window and then outputs a train of pulses having a constant separation equal to the average separation of the pulses from the autocompensator 31. The smoothing filter 30 outputs this pulse train to the stage controller 25. The 16 pulse window is simply the last 16 pulses input by the smoothing filter 30 from the autocompensator 31. The window is active when the last 16 pulses are being averaged and output to the stage controller. The window is inactive while the stage is accelerating or decelerating and the pulse train output from the autocompensator simply is passed through to the stage controller 25 by the smoothing filter 30 without modification. The window is inactive during acceleration or deceleration since the separation between pulses is undergoing rapid changes and an average would give an untrue picture of the stage 118 position. That is, the pulse separation is not expected to remain constant for the last 16 pulses. All input pulse separation averaging logic will be reset if the stage changes its direction of travel.

Figure 8:
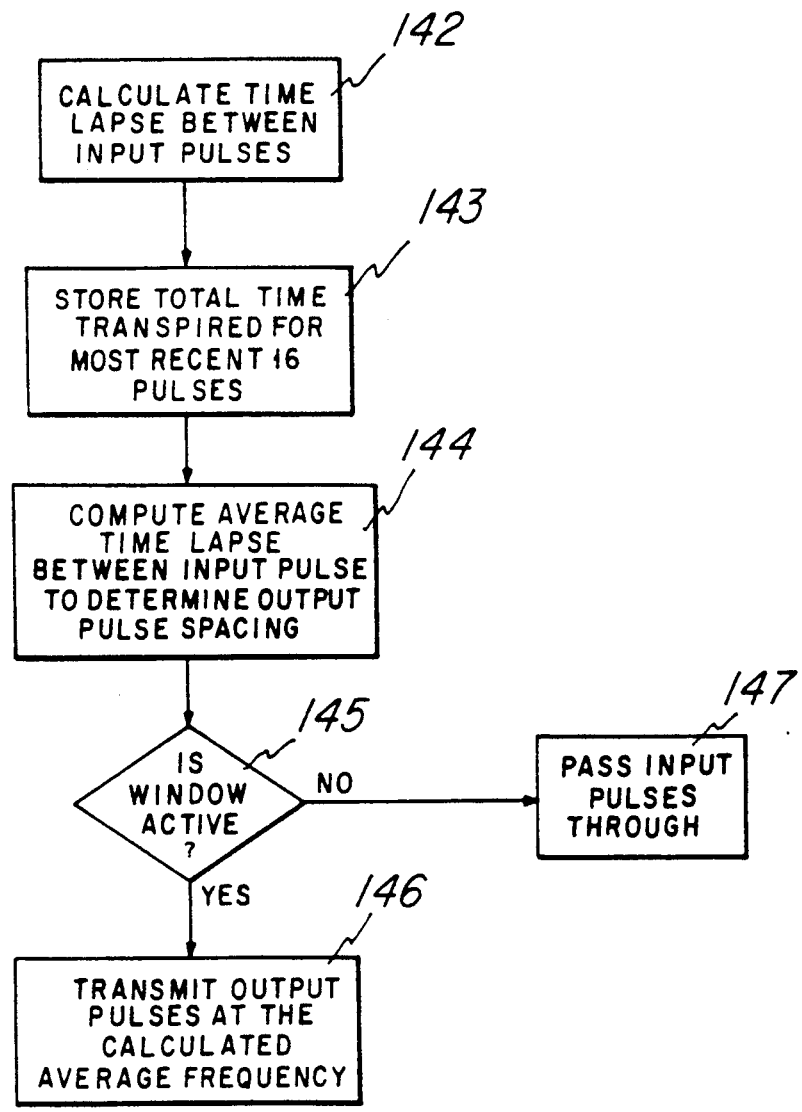
FIG. 8 is a flow chart illustrating a smoothing filter algorithm.

The smoothing filter 30 includes a bit-slice arithmetic logic unit and a pulse interval counter. FIG. 8 illustrates the flow of functions of the smoothing filter. As indicated at block 142, the pulse interval counter operates in a free-running mode to calculate the time lapse between input pulses. The smoothing filter 30 includes a pulse interval accumulator (memory) which stores the total amount of time transpired over the most recent 16 input pulses, as indicated at block 143. As indicated at block 144, the smoothing filter uses the total time saved in the accumulator to compute the average time lapse between the input pulses received from the autocompensator 31. The average time lapse is used as the spacing for the pulses output to the stage controller 25. The decision is then made at block 145 as to whether the window is active. If the window is active, then the pulses output from the smoothing filter will have a frequency determined by the average pulse spacing, as indicated at block 146. If the window is inactive, then the smoothing filter passes the input pulses through to the stage controller without change, as seen at block 147.

The pulse interval counter is a free running counter that counts the number of clock cycles occurring between pulses.

The pulse interval accumulator holds the total amount of time transpired over the most recent 16 input pulses. As each new pulse arrives, the value found in the pulse interval counter is added to the accumulator and stored. This continues over the first 16 pulses. Beyond the first 16 pulses, the oldest value is subtracted from the accumulator before the new value is added.

The pulse interval averager computes the average time lapse between input pulses to determine the output pulse spacing. Prior to reception of the first 16 input pulses, when the window is closed, the pulse interval averager values are not used, and input pulses are passed directly to the stage controller 25. Upon reception of the sixteenth input pulse and all pulses thereafter, the accumulator is divided by 16. This value is continually updated upon each pulse received for the remainder of the window opening or until errors occur.

Pattern Writer Data Flow

Figure 9:
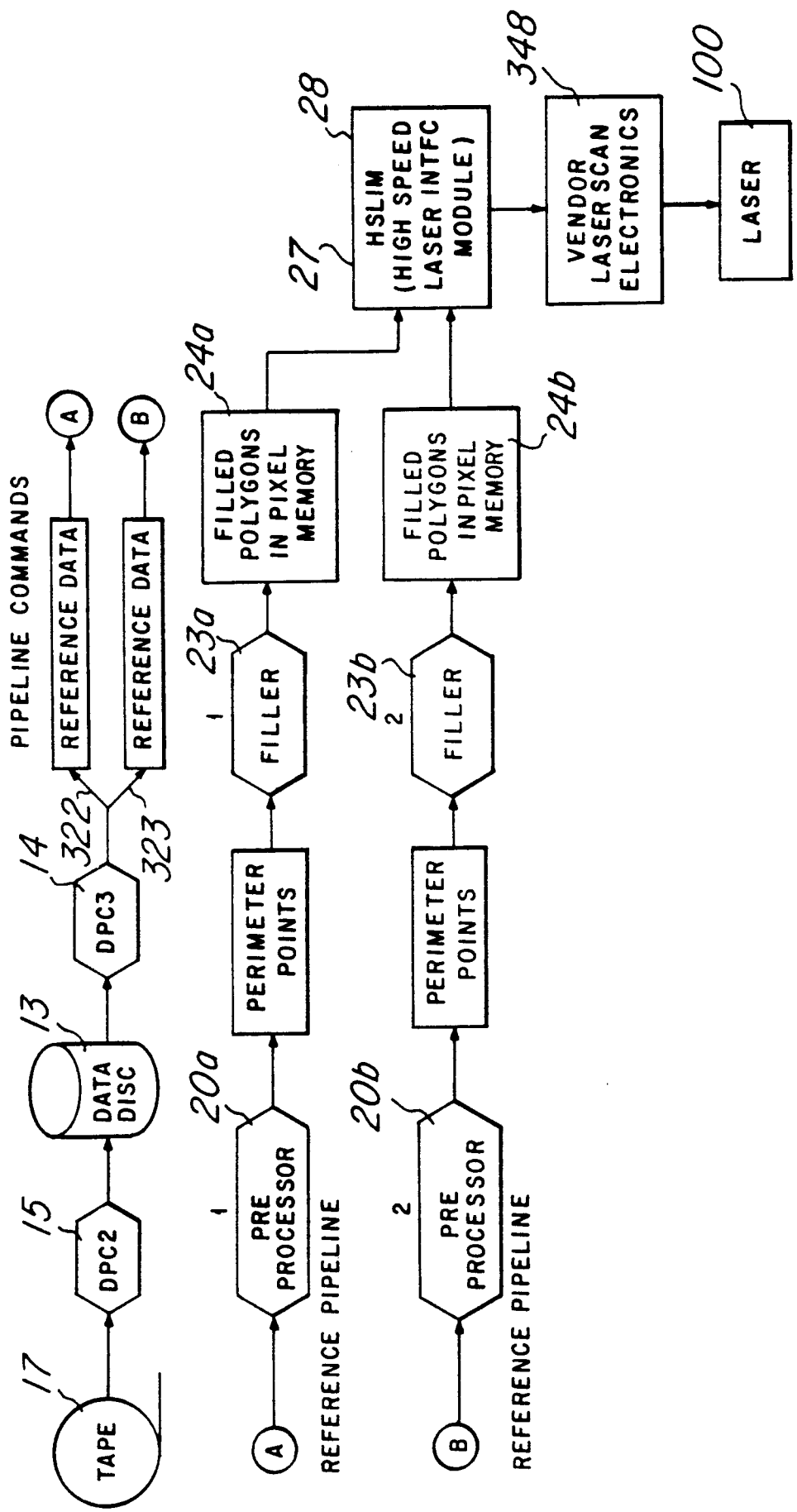
FIG. 9 is a data flow diagram for the pattern writer system.

The database on tape 17, shown in FIGS. 6 and 9, for a part which is to be written on photosensitive surface 121, is identical to the database on tape 17 for a part which is to be inspected. Therefore, the following description of the organization of the database as it exists on tape 17 is applicable equally to a pattern writer system 50 or a pattern inspection system 400.

Tape 17 is organized into a series of records, each 4000 bytes long. All information stored on the tape is stored in 16 bit words, and all numeric values will be limited to 32767.

The database stored on tape 17 is comprised of two Main Directory Records, followed by two Target 103 Header Records, which in turn are followed by however many Data Records as are required to describe the geometrical patterns to be written on photosensitive surface 121.

FIG. 10 is a table indicating the contents of Main Directory Record 1. As is evident from the table, this record contains information useful for documentation purposes, such as the date the tape was generated. Record 1 also contains information necessary for the correct scaling of the database to real-world dimensions. For example, Word 5 is a number in binary which is in 0.01 micron units. Typically, for printed wiring board writing, this number will be 100 decimal, that is, the unit size is one micron. This one micron value is the size of one address unit. One address unit is also the size of one pixel.

Data records stored on tape 17 are organized so that a target 103 surface 121, as shown in FIGS. 1-4, is treated as though it is subdivided into strips 105 parallel to the Y axis, each of which is 1024 pixels 119 in width. Each strip 105 is subdivided into frames 106 each of which is 512 pixels high. Thus, the entire target surface 121 will consist of rectangles 1024 by 512 pixels in size. The strips 105 start at the left side of the target 103 and in the data records are numbered from zero to N, where (N+1) * 1024 is greater than or equal to the target surface 121 width. The frames 106 for each strip start at the top of that strip and in the data records are numbered from zero to K, where (K+1) * 512 is greater than or equal to the target surface 121 height.

Returning to FIG. 10, Word 7 indicates the strip 105 (frame 106) width in address units (pixels). Typically this value will be 1024. Word 8 is the frame 106 height in address units. Typically this value will be 512.

Word 9 indicates whether writing or inspection will take place. The type of target is also indicated, e.g., a reticle or mask. Reticles and masks have been mentioned by way of example only, and it is understood that printed wiring boards, semiconductor wafers and other targets can also be written on or inspected.

Word 53 indicates whether a target 103 is to be written on or inspected in serpentine fashion or from the top to the bottom of every strip 105.

FIG. 11 is a table indicating the contents of Main Directory Record 2. This record mainly keeps track of the Header Record number for each set of target data records stored on the tape 17. It is apparent that a tape may contain data records for writing or inspecting more than one target pattern. By first target, second target and so on, sets of target data records are being indicated. Each set of target data records defines a geometrical pattern which is to be written on a target 103 or it defines an ideal pattern against which an actual physical pattern on a target 103 can be compared.

For each set of target data records there are two Target Header Records, although Target Header Record 2 is not presently used. FIG. 12 is a table indicating the contents of Target Header Record 1. Any pattern which is to be written on a target or serve as a standard for inspection, is constructed of polygons which do not cross frame 106 boundaries. Even patterns with curved lines can accurately be represented by polygons with straight sides if the polygons are sufficiently small. Words 3 and 4 indicate the number of these polygons for that set of target records.

Word 5 indicates the number of the first strip that contains non-zero data. That is, the first strip containing any polygons. Likewise, Word 6 indicates the number of the last strip 105 that contains non-zero data. Word 7 indicates the number of the first frame 106 that contains non-zero data, and Word 8 indicates the number of the last frame that contains non-zero data. Thus, the stage 118 can be immediately advanced to the first strip 105 and frame 106 that contain non-zero data to begin raster scanning the target 103 surface 121 at that frame. Similarly, raster scanning can be made to cease as soon as the last strip and frame containing non-zero data have been raster scanned. This can result in quicker run-time of the writing or inspection processes.

The geometric data on the tape is contained in the Data Records following the Target Header Records. This data describes one or more polygons which, when taken together, forms an approximation of the geometrical pattern which is to be written on target surface 121, or which is on target surface 121 and will be inspected and compared against the ideal pattern defined by the data records. Each polygon is completely contained within a frame 106. Furthermore, each polygon must be a convex polygon in the X direction. That is, for a polygon to be convex in the X direction, any line drawn parallel to the X axis must intersect the boundary of the polygon twice at most. This is required because polygons are written or inspected by raster scanning rows parallel to the X axis. Each polygon is written by turning the laser beam on when the left edge of the polygon is encountered and turning the laser beam off when the right edge of the polygon is reached. That is, all the pixels 119 within the polygon must be written to or inspected. If polygons were not convex in the X direction, the laser beam would need to be turned on more than once and off more than once for the same polygon.

Figure 13:
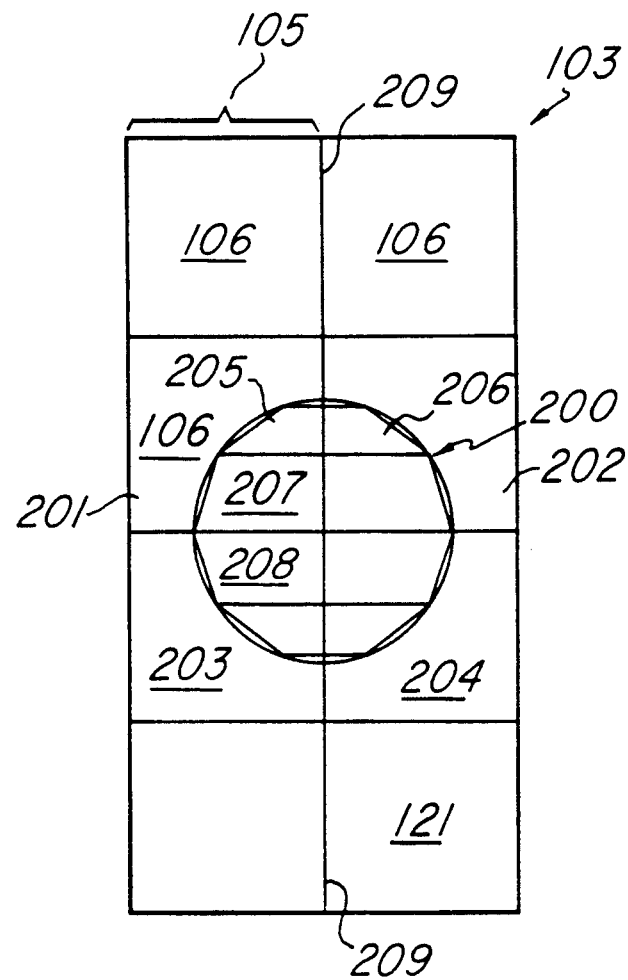
FIG. 13 is a plan view of a target showing a pattern and its constituent polygons.

For example, FIG. 13 shows a target 103 consisting of two strips 105 and eight frames 106. It is desired to write, or inspect, a filled circle 200 (a disk) on surface 121 so that the filled circle overlaps frames 201, 202, 203 and 204. The filled circle 200 is represented in the data records as being made up of eight polygons. During a writing process, the laser writer system 50 will write on surface 121 the geometrical shape defined by the eight contiguous polygons. During a process of inspecting a pre-existing pattern on surface 121, such as a developed pattern on a photoresist covered board, the pre-existing pattern is compared against the ideal pattern defined by the eight polygons.

Each polygon lies completely within a single frame. For example, polygons 205 and 207 both lie completely in frame 201; polygon 208 lies completely in frame 203; and polygon 206 lies completely in frame 202. Polygons 205 and 206 are contiguous with a common border along strip boundary 209. Polygons 207 and 208 are contiguous with a common border along frame boundary 210. The geometrical pattern defined by the polygons will more closely approximate the filled circle 200 if more than eight polygons are used to describe the filled circle. This is a limit process and is similar to some numerical methods of integration, or approximations of the value of an integral. As many polygons are used to describe a geometrical pattern as are necessary for predetermined tolerances. For example, the tolerances allowed on a printed wiring board will become tighter as the circuit density of the board increases. Likewise, more accuracy is required for multi-layer artwork than typically would be necessary for single layer artwork.

The geometric data in the Data Records is subdivided into contiguous frames of data which correspond to the frames 106 shown superimposed on the target surface 121. All frames are indicated or represented in the Data Records even if there is no polygon data in the frame. Corresponding to each superimposed frame 106 containing one or more polygons, is a frame of data containing data descriptive of those polygons. Each such polygon is described by the X-Y coordinate of one of the vertices of the polygon and various X and Y displacements. All X-Y coordinates are positive displacements from the upper left corner of the frame, which is considered to be the origin for that frame. The exact form of the description depends upon the geometrical properties of the polygon. There are nine categories of polygons which can be used in the Data Records. Some of these categories are further subdivided into two or four subcategories.

Each polygon's descriptive data is immediately preceded by an identifying 16 bit control word, illustrated in the table in FIG. 23. Bits zero through five of this control word are used to designate the category and subcategory (if applicable) of polygon whose data immediately follows this control word.

Bits 8 through 11 of the identifying control word of FIG. 23, contain information, concerning the polygon in the description following the identifying control word, which is useful in generating guardbands (don't-care zones) around the polygon during the inspection process. Specifically, bits 8 through 11 indicate whether the polygon being described has a side(s) on the left, right, top or bottom frame boundary and is in common with another polygon in the next frame to the left, right, top or bottom, respectively. If two polygons have a frame boundary, or portion thereof, in common, then, those two polygons together describe a larger, inclusive polygon on whose sides and interior all pixels are part of the pattern to be written during writing or compared with during inspection. Guardbands are generated by DPC2 15 shown in FIGS. 6 and 9.

The database as it exists on tape 17 is the same for a writer and an inspector. During the writing process, no guardbands are generated and the information in bits eight through eleven is ignored by the writer system 50.

Figure 14:
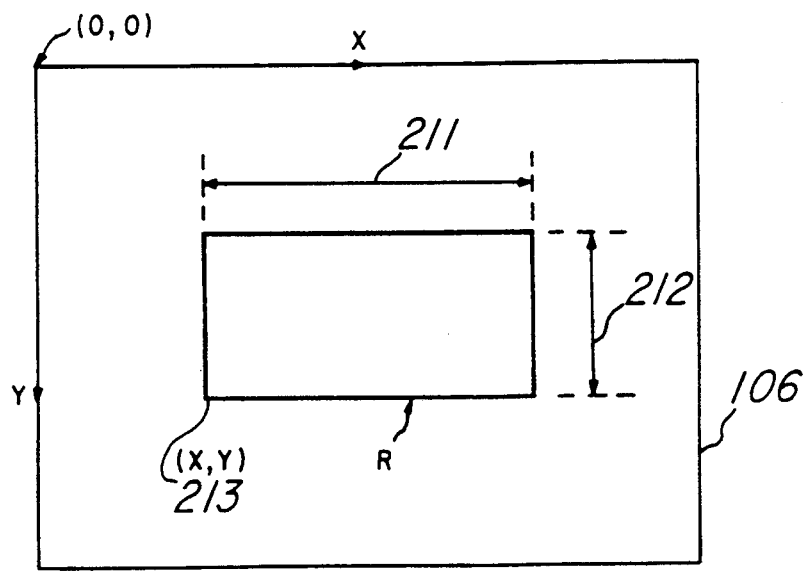
FIG. 14 is a plan view of an allowed rectangular polygon.

FIG. 14 illustrates the category of polygons which is comprised of rectangles. Rectangle R is shown contained within frame 106, and is described in the Data Records by four 16 bit words following the identifying control word. The first word is the X coordinate and the second word the Y coordinate of lower left corner 213. The third word is the width 211 in pixels 119, and the fourth word is the height 212 in pixels.

Bits 0 through 5 of the identifying control word equals 07 in hexadecimal which indicates that the data words following the control word describe a rectangle. Bits 8 through 11 of the indentifying control word have the following meanings: If bit 8 is a 1, then the bottom edge of the rectangle R is on the frame 106 boundary and is in common with another polygon in the next frame below. If bit 9 is 1 the right edge of the rectangle R is on the frame boundary and is in common with another polygon in the next frame to the right. If bit 10 is 1 the top edge of the rectangle R is on the frame 106 boundary and is in common with another polygon in the next frame above. If bit 11 is equal to 1 then the left edge of the rectangle R is on the frame boundary and is in common with another polygon in the next frame to the left.

Figure 15:
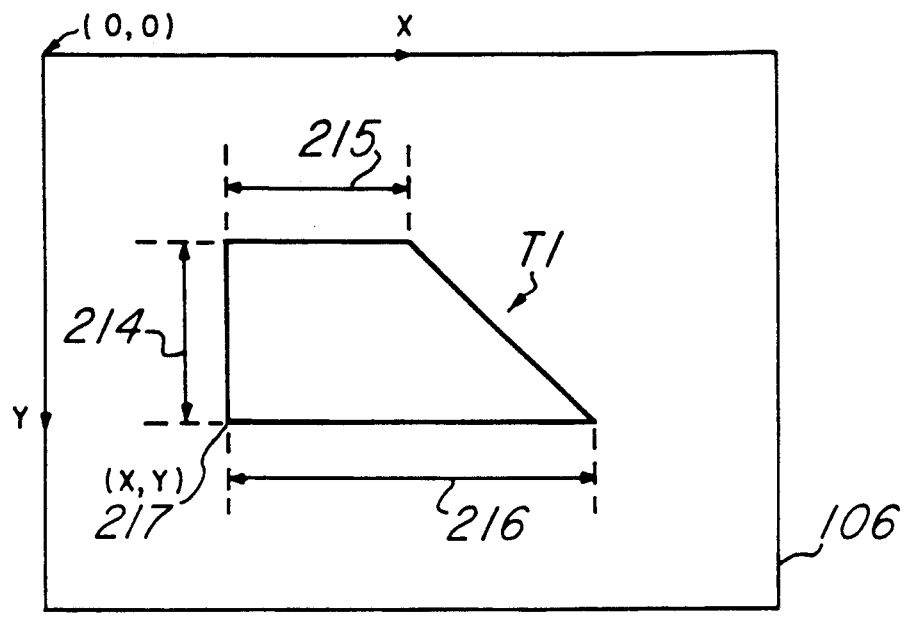
FIG. 15 is a plan view of an allowed trapezoidal polygon with parallel upper and lower sides and a vertical left side.

FIG. 15 illustrates the category of polygons which is comprised of trapezoids T1 having horizontal top and bottom sides and a vertical left side. Although the trapezoid T1 which is illustrated is shown with a right side having a positive slope (Y has opposite sign relative to conventional cartesian coordinate system), this category of polygons includes negative slopes as well. Following the identifying control word will be either 4 or 5 words depending upon whether or not the slope of the right side is + or −1. The right side has slope equal to 1 if bits 0 through 5 equal 08 hex, or slope −1 if bits 0 through 5 equal 09 hex, provided bit 12 is 1. If the slope is + or −1 then only four data words are required to describe the polygon.

This trapezoid T1 of FIG. 15 is described by the following five words: Word 1 is the X coordinate and word 2 is the Y coordinate of the lower left corner 217. Word 3 is height 214 and word 4 is width 216. Word 5 is the width 215. If only four words are required to describe the trapezoid T1, then word 5 which is the width 215 is not used.

Bits 0 through 5 of the identifying control word equal 08 hex if the right side has a positive slope, and equal 09 hex if the right side has a negative slope. If bit 8 is 1 the bottom edge of the trapezoid T1 is on the frame boundary and is in common with another polygon in the next frame 106 below. Bit 9 is 0. If Bit 10 is 1 then the top edge of the trapezoid T1 is on the frame boundary and is in common with another polygon in the previous frame above. If bit 11 is 1 then the left edge of the trapezoid T1 is on the frame boundary and is in common with another polygon in the next frame to the left. If bit 12 is 1 then the right side of the trapezoid T1 is at 45 degrees and hence width 215 is not used. Bit 13 will be 0.

Figure 16:
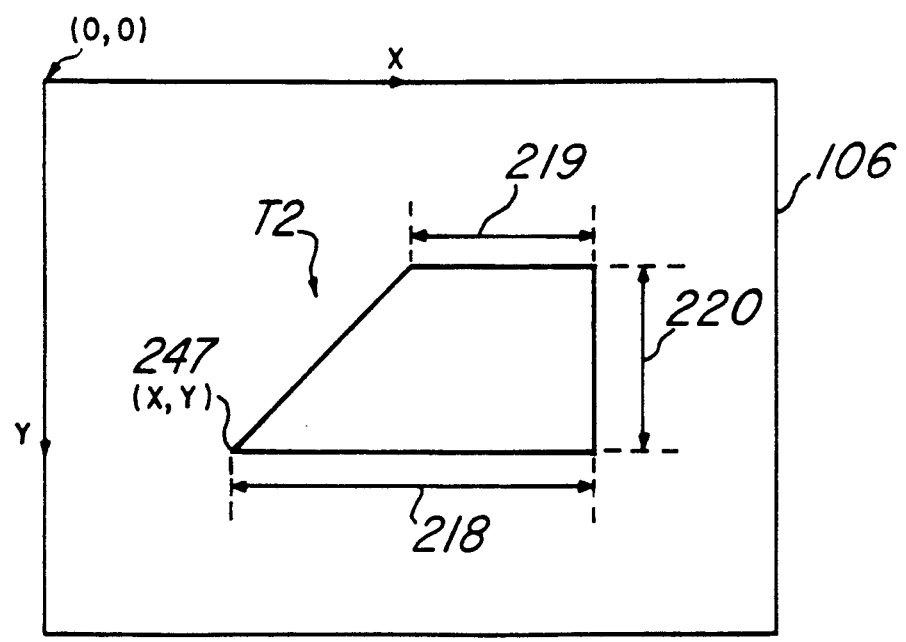
FIG. 16 is a plan view of an allowed trapezoidal polygon with parallel upper and lower sides and a vertical right side.

FIG. 16 illustrates the category of polygons which is comprised of trapezoids T2 having horizontal top and bottom sides, a vertical right side and a sloping left side. Although the trapezoid T2 is shown with a left side having a negative slope, this category of polygons includes polygons with positive slopes as well. Following the identifying control word will be either 4 or 5 words describing the trapezoid, depending upon whether or not the slope of the left side is + or −1. The left side has slope equal to 1 if bits 0 through 5 equal 0A hex, or slope −1 if bits 0 through 5 equal 0B hex, provided bit 13 is 1. If the slope is + or −1 then only four data words are required to describe the polygon.

If the slope of the left side of trapezoid T2 is not + or −1, then the following five words are required to describe the polygon: Word 1 is the X coordinate and word 2 is the Y coordinate of the lower left corner 247. Word 3 is height 220 and word 4 is width 218. Word 5 is the width 219. If only four words are required to describe the trapezoid T2, then word 5, which is width 219, is not used.

Bits 0 through 5 of the identifying control word equal 0A hex if the left side has a positive slope, and equal 0B hex if the left side has a negative slope. If bit 8 is a 1 then the bottom edge is on the frame 106 boundary and is in common with another polygon in the next frame below. If bit 9 is a 1, then the right edge is on the frame boundary and is in common with another polygon in the next frame to the right. If bit 10 is a 1, then the top edge if the polygon is on the frame boundary and is in common with another polygon in the previous frame above. Bits 11 and 12 are 0. If bit 13 is 1 then the left side has a 45 degree slope and width 219 is not used to describe the polygon T2.

Figure 17:
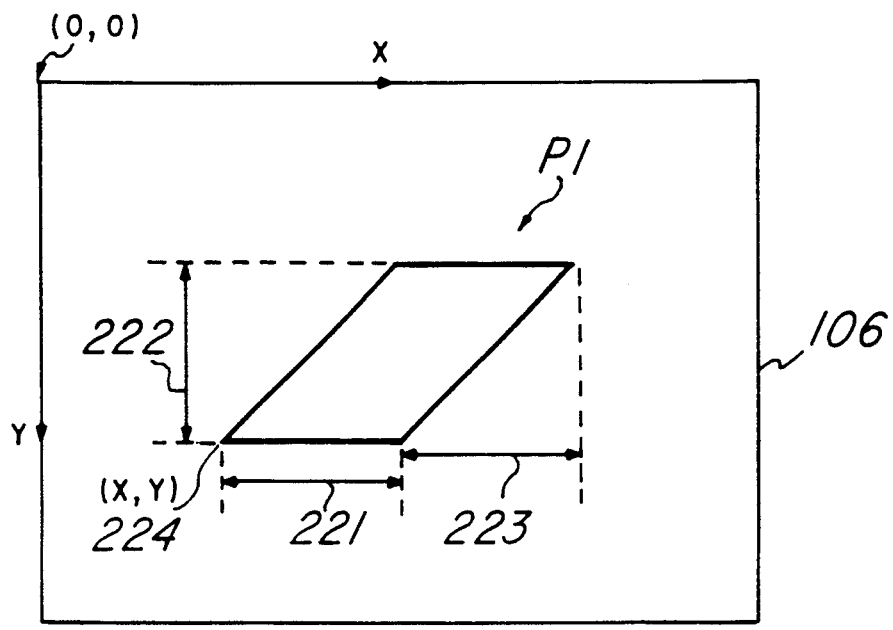
FIG. 17 is a plan view of an allowed parallelogram polygon with horizontal top and bottom sides.

FIG. 17 illustrates the category of polygons which is comprised of parallelograms P1 having horizontal top and bottom sides, and the other two sides are sloping. Parallelogram P1 is shown with negative sloping sides, however, this category of polygons includes parallelograms with positive slopes as well. Following the identifying control word will be either 4 or 5 words describing the parallelogram P1, depending upon whether or not the slope of the slanted sides is + or −1. The slanted sides have a slope of +1 if bits 0 through 5 equal 0C hex, or slope −1 if bits 0 through 5 equal 0C hex, provided bits 21 and 13 both are 1. If the slope is + or −1 then only four data words are required to describe the polygon P1.

If the slope of the slanted sides of parallelogram P1 is not + or −1, then the following five words are required to describe the polygon: Word 1 is the X coordinate and word 2 is the Y coordinate of the lower left vertex 224. Word 3 is height 222 and word 4 is width 221. Word 5 is delX 223. If only four words are required to describe the parallelogram P1, then the word 5, which is delX 223, is not used.

Bits 0 through 5 of the identifying control word equal 0C hex if the slanted sides have a positive slope, and equal 0D hex if the slanted sides have a negative slope. If bit 8 is 1 then the bottom edge is on the frame 106 boundary and is in common with another polygon in the next frame below. Bit 9 is 0. If Bit 10 is 1 then the top edge of the parallelogram is on the frame boundary and is in common with another polygon in the previous frame above. Bit 11 is 0. If bits 12 and 13 are both 1, then the slanted sides are at 45 degrees and delX 223 is not used.

Figure 18:
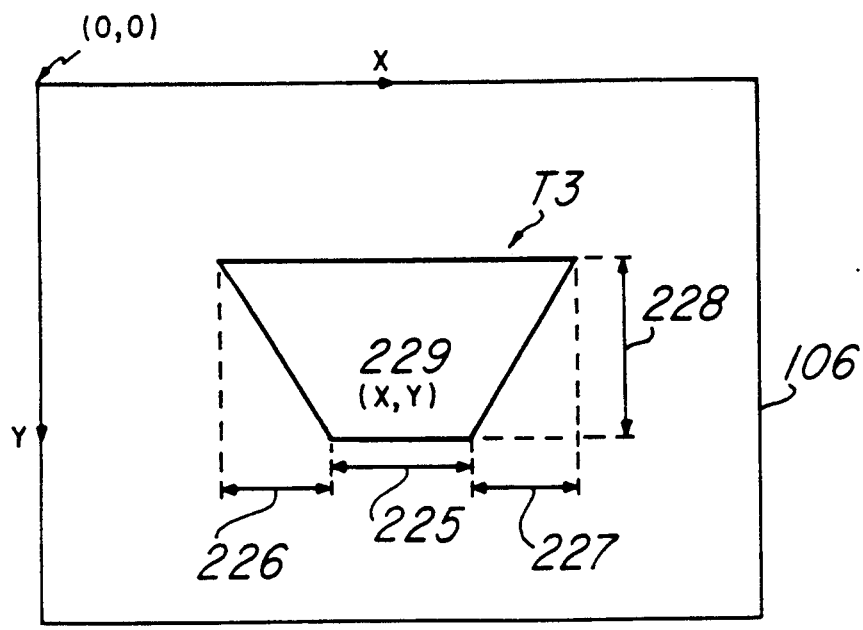
FIG. 18 is a plan view of an allowed trapezoidal polygon with parallel top and bottom sides.

FIG. 18 illustrates the category of polygons which is comprised of trapezoids T3 having horizontal top and bottom sides, and the left and right sides are slanted. Although the trapezoid T3 is shown with a left side having a positive slope and a right side having a negative slope, this category of polygons includes polygons having left and right sides with either positive or negative slopes in any combination. Following the identifying control word will be either 4, 5 or 6 words describing the trapezoid T3, depending upon whether or not the slopes of the left and/or right sides are + or −1. The left and right sides have slopes equal to 1 if bits 0 through 5 equal 0E hex, or slopes equal to −1 if bits 0 through 5 equal 0F hex, provided bits 12 and 13 are both −1. Thus only four data words are required to describe the polygon. Likewise, the left side has slope equal to one and the right side has slope equal to −1, provided bits 0 through 5 equal 10 hex and bits 12 and 13 are both 1. Thus, only four data words are required to describe the polygon. Similarly, the left side has slope equal to −1 and the right side has slope equal to +1, provided bits 0 through 5 equal 11 hex and bits 12 and 13 are both 1. In this case as well, only four data words are required to describe the polygon.

If four data words only are required to describe the polygon, the words are the following: Word 1 is the X coordinate and word 2 is the Y coordinate of the lower left vertex 229. Word 3 is height 228 and word 4 is width 225.

If either the left side or the right side (but not both) of polygon T3 is equal to + or −1, then five words will be required to describe polygon T3. In this case, the same four words are required to describe the polygon T3 as above, but in addition, either delX 226 or delX 227 will follow width 225. DelX 226 is required if the left side does not have a slope of + or −1. DelX 227 is required if the right side does not have a slope of + or −1.

If neither the right or left sides have slopes of + or −1, then six words must be used to describe the polygon T3. That is, both delX 226 and delX 227 are required. DelX 226 followed by delX 227 will follow the width 225.

Bits 0 through 5 of the identifying control word equal 0E hex if both the left and the right sides have positive slope, equal 0F hex if both the left and right sides have negative slope, equal 10 hex if the left side has positive slope and the right side has negative slope, and equal 11 hex if the left side has negative slope and the right side has positive slope. If bit 8 is 1, then the bottom edge of the trapezoid T3 is on the frame 106 boundary and is in common with another polygon in the next frame below. Bit 9 is 0. If bit 10 is 1, then the top edge of the trapezoid T3 is on the frame boundary and is in common with another polygon in the previous frame above. Bit 11 will be off. If bit 12 is on then the right slanted side is 45 degrees and hence delX 227 is not used. If bit 13 is 1, then the left slanted side is at 45 degrees and hence delX 226 is not used in the polygon description.

Figure 19:
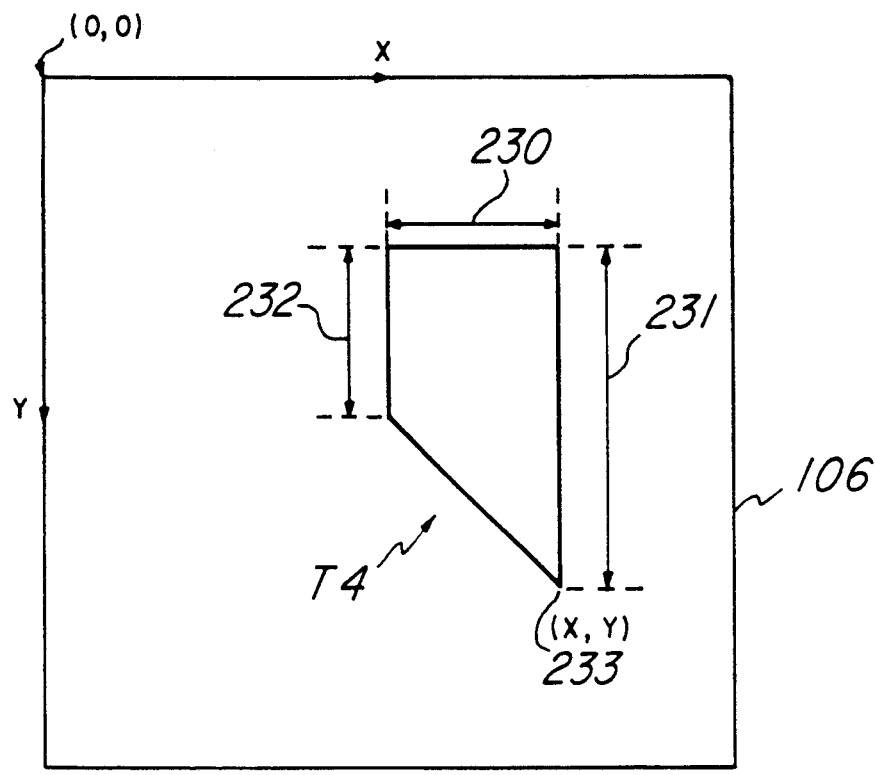
FIG. 19 is a plan view of an allowed trapezoidal polygon with parallel left and right sides and a horizontal top side.

FIG. 19 illustrates the category of polygons which is comprised of trapezoids T4 having left and right vertical sides, a horizontal top side and a slanted bottom side. Although the trapezoid T4 is shown with a bottom side having a positive slope, this category of polygons includes polygons with negative slopes as well. Following the identifying control word will be either 4 or 5 words describing the trapezoid T4, depending upon whether or not the slope of the bottom side is + or −1. The bottom side has slope equal to +1 if bits 0 through 5 equal 12 hex, or slope equal to −1 if bits 0 through 5 equal 13 hex, provided bit 13 is 1. If the slope is + or −1 then only four data words are required to describe the trapezoid T4.

If the slope of the bottom side of trapezoid T4 is not + or −1, then the following five words are required to describe the polygon: Word 1 is the X coordinate and word 2 is the Y coordinate of the lower right vertex 233. Word 3 is width 230 and word 4 is height 231. Word 5 is the height 232. If only four words are required to describe the trapezoid T4, then word 5, which is height 232, is not used.

Bits 0 through 5 of the identifying control word equal 12 hex if the bottom side has a positive slope, and equal 13 hex if the bottom side has a negative slope. Bit 8 is 0. If bit 9 is 1, then the right edge of the trapezoid is on the frame 106 boundary and is in common with another polygon in the next frame to the right. If bit 10 is 1, then the top edge of the polygon T4 is on the frame boundary and is in common with another polygon in the previous frame above. If bit 11 is 1, then the left edge of the trapezoid T4 is on the frame boundary and is in common with another polygon in the next frame to the left. Bit 12 is 0. If bit 13 is 1, then the slanted bottom side is at 45 degrees and hence the height 232 is not used.

Figure 20:
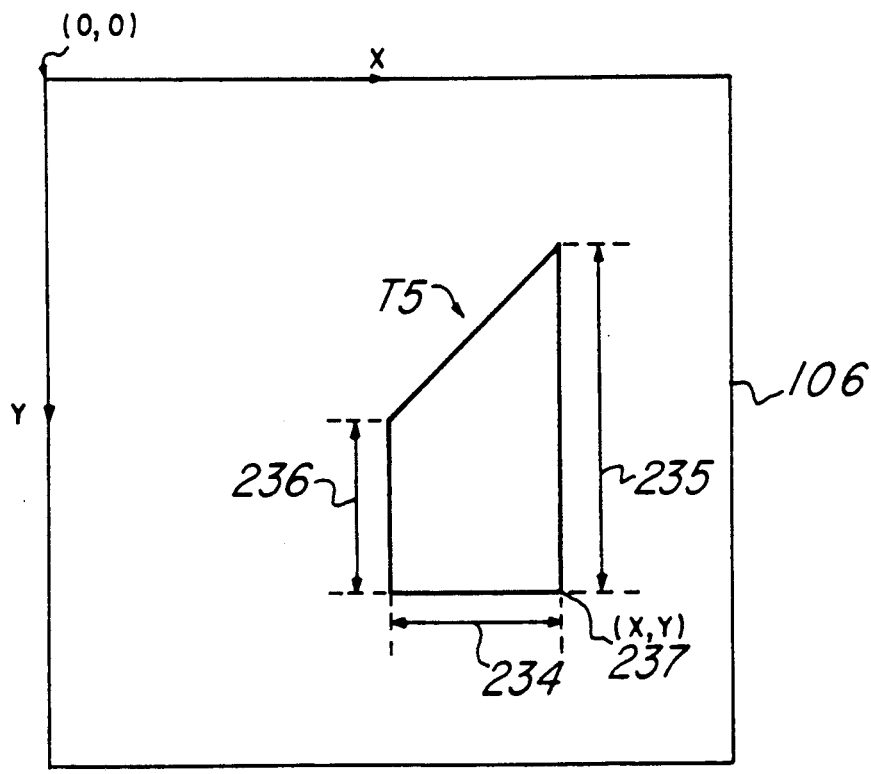
FIG. 20 is a plan view of an allowed trapezoidal polygon with parallel left and right sides and a horizontal bottom side.

FIG. 20 illustrates the category of polygons which is comprised of trapezoids T5 having left and right vertical sides, a horizontal bottom side and a slanted top side. Although the trapezoid T5 is shown with a top side having a negative slope, this category of polygons includes polygons with positive slopes as well. Following the identifying control word will be either 4 or 5 words describing the trapezoid, depending upon whether or not the slope of the top side is + or −1. The top side has slope equal to 1 if bits 0 through 5, of the identifying control word, equal 14 hex, or slope −1 if bits 0 through 5 equal 15 hex, provided bit 12 of the identifying control word is 1. If the slope is + or −1 then only four data words are required to describe the polygon.

If the slope of the top side of trapezoid T5 is not + or −1, then the following five words are required to describe the polygon: Word 1 is the X coordinate and word 2 is the Y coordinate of the lower right corner 237. Word 3 width 234 and word 4 is height 235. Word 5 is the height 236. If only four words are required to describe the trapezoid T5, then word 5, which is height 236, is not used.

Bits 0 through 5 of the identifying control word equal 14 hex if the top side of trapezoid T5 has a positive slope, and equal 15 hex if the top side has a negative slope. If bit 8 is 1, then the bottom edge of trapezoid T5 is on the frame 106 boundary and is in common with another polygon in the next frame below. If bit 9 is 1, then the right edge of trapezoid T5 is on the frame boundary and is in common with another polygon in the next frame to the right. Bit 10 is 0. If bit 11 is 1, then the left edge of trapezoid T5 is on the frame boundary and is in common with another polygon in the next frame to the left. If bit 12 is 1, then the slanted top side of trapezoid T5 has slope of 45 degrees, hence height 236 is not used. Bit 13 is 0.

Figure 21:
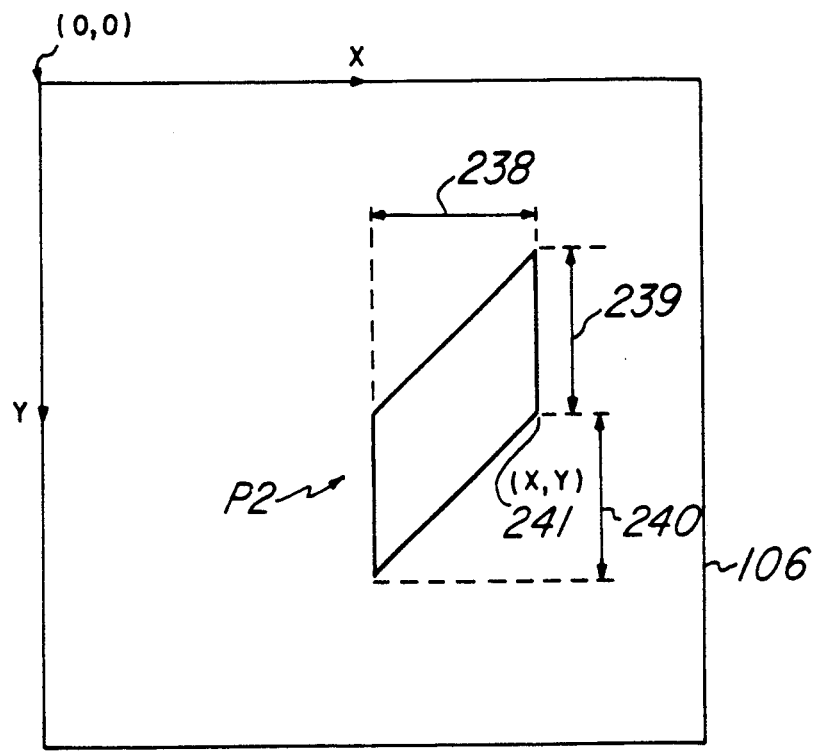
FIG. 21 is a plan view of an allowed parallelogram polygon with vertical left and right sides.

FIG. 21 illustrates the category of polygons which is comprised of parallelograms P2 having left and right vertical sides, and slated top and bottom sides. Although the parallelogram P2 is shown with slanted sides having a negative slope, this category of polygons includes parallelograms with positive sloped top and bottom sides as well. Following the identifying control word will be either 4 or 5 words describing the parallelogram, depending upon whether or not the slope of the top and bottom sides is + or −1. The top and bottom sides have a slope equal to 1 if bits 0 through 5 of the identifying control word equal 16 hex, or slope −1 if bits 0 through 5 equal 17 hex, provided bits 12 and 13 of the identifying control word are both equal to 1. If the slope is + or −1 then only four data words are required to describe the parallelogram.

If the slope of the top and bottom sides of the parallelogram P2 is not + or −1, then the following five words are required to describe the parallelogram: Word 1 is the X coordinate and word 2 is the Y coordinate of the lower right vertex 241. Word 3 is width 238 and word 4 is height 239. Word 5 is delY 240. If only four words are required to describe the parallelogram P2, then word 5, which is delY 240, is not used.

Bits 0 through 5 of the identifying control word equal 16 hex if the top and bottom sides have a positive slope, and equal 17 hex if the top and bottom sides have a negative slope. Bit 8 is 0. If bit 9 is 1, then the right edge of the parallelogram P2 is on the frame boundary and is in common with another polygon in the next frame to the right. Bit 10 is 0. If bit 11 is 1 then the left edge of parallelogram P2 is on the frame 106 boundary and is in common with another polygon in the next frame to the left. If bits 12 and 13 are both 1 then the top and bottom sides have slope equal to 45 degrees, hence delY 240 is not used.

Figure 22:
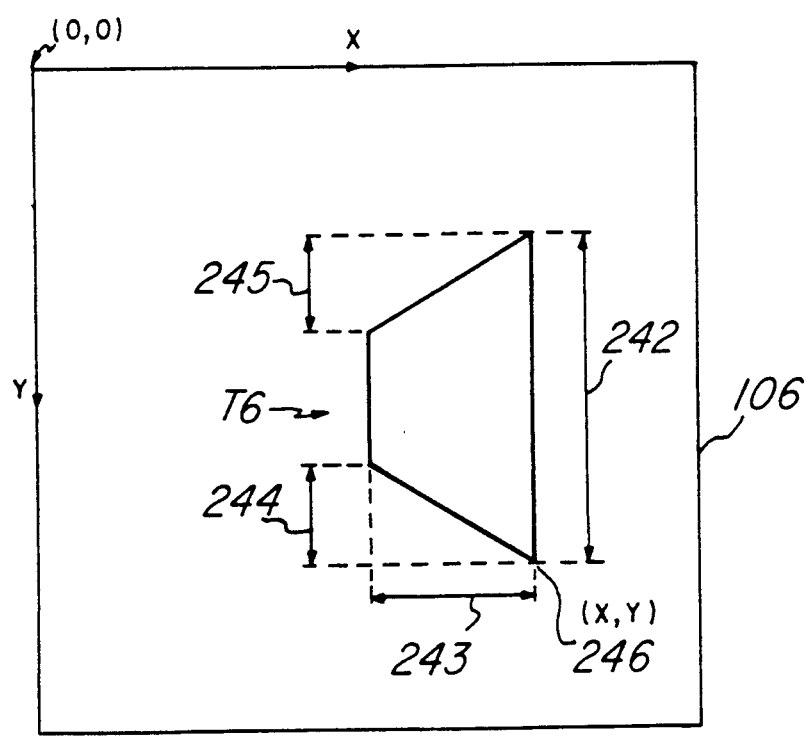
FIG. 22 is a plan view of an allowed trapezoidal polygon with parallel left and right sides.

FIG. 22 illustrates the category of polygons which is comprised of trapezoids T6 having vertical left and right sides, and slanted top and bottom sides. Although the trapezoid T6 is shown with the top side having a negative slope and the bottom side having a positive slope, this category of polygons also includes polygons with top and bottom sides having any combination of positive and negative slopes. Following the identifying control word will be either 4, 5 or 6 words describing the trapezoid T6, depending upon whether or not the slopes of the top and bottom sides are + or −1. The top side has slope equal to +1 if bits 0 through 5 of the identifying control word equal 18 hex or 1B hex, or slope equal to −1 if bits 0 through 5 equal 19 hex or 1A hex, provided that bit 12 is equal to 1. The bottom side has slope equal to +1 if bits 0 through 5 of the identifying control word equal 18 hex or 1A hex, or slope equal to −1 if bits 0 through 5 equal 19 hex or 1B hex, provided that bit 13 is equal to 1.

If both top and bottom sides have a slope equal to + or −1, then only four words are required to describe the trapezoid T6. Those four words are: Word 1 is the X coordinate and word 2 is the Y coordinate of the lower right vertex 246. Word 3 is width 243 and word 4 is height 242.

If the top side has a slope equal to + or −1, and the bottom side has a slope not equal to + or −1, then, in addition to words 1 through 4, word 5 is also required to describe trapezoid T6. Word 5 is delY 244.

If the bottom side has a slope equal to + or −1, and the top side has a slope not equal to + or −1, then, in addition to words 1 through 4, word 5 is also required to describe trapezoid T6. Word 5 is delY 245. Word 5 is now defined differently than in the case described in the preceding paragraph.

If neither top or bottom sides have slope equal to + or −1, then six words are required to describe the trapezoid T6. Words 1 through 4 are the same as in the other three cases. Word 5 now is delY 244 and word 6 is delY 245.

Bits 0 through 5 of the identifying control word equal 18 hex when both top and bottom sides have positive slopes. Bits 0 through 5 equal 19 hex when both top and bottom sides have negative slopes. Bits 0 through 5 equal 1A hex when the bottom side has positive slope and the top side has negative slope. Bits 0 through 5 equal 1B hex when the bottom side has negative slope and the top side has positive slope.

Bit 8 of the identifying control word equals 0. If bit 9 is 1, then the right side of trapezoid T6 is on the frame 106 boundary and is in common with another polygon in the next frame to the right. Bit 10 is 0. If bit 11 is 1, then the left side of the trapezoid T6 is on the frame boundary and is in common with another polygon in the next frame to the left. If bit 12 is 1, then the top side has 45 degree slope, hence delY 244 is not used to describe trapezoid T6. If bit 13 is 1, then the bottom side has a 45 degree slope, hence delY 245 is not used to describe trapezoid T6.

FIGS. 23 and 24 are tables indicating the meanings of the bits constituting the 16 bit control words which are embedded throughout the Data Records of the database. A one in bit position 15 indicates that that 16 bit word is a control word. The type of control word it is is indicated by bits 0 through 5. These bits are called the control bits. For instance, the meanings of the control bits has been explained in connection with FIGS. 14–22 when their value is 07 hex through 1B hex. When bits 0 through 5 take on one of the values 07 hex through 1B hex, the control word is referred to as an identifying control word. The identifying control word identifies the characteristics of the polygon represented by the data words immediately following the control word in the Data Records.

FIG. 24 lists the control bits and their meaning for seven types of control words other than identifying control words. When the control bits equal 00 hex, that control word is the first word to appear on the tape and it precedes the first Main Directory File. The other control words can be understood in the outline of the Data Records shown in FIG. 25.

The first word shown in FIG. 25 is the Beginning of Strip control word. Each strip of data begins with this word. This control word is followed by a 16 bit strip ID number. Next follows the Beginning of Frame control word, followed by a 16 bit frame ID number. This is followed by the identifying control word, Beginning of Polygon. The data defining the polygon follows. After this, another polygon is indicated and defined followed by control words indicating the End of Frame, Frame ID, End of Strip and then End of Target. End of Target indicates that there is no more data to be written on target 103 surface 121 or, alternatively, that there is no more ideal pattern information against which an actual pattern is to be compared. In the example of FIG. 24, two polygons were in one frame, in a single strip, however, many polygons can be in one frame, and there may be many frames and strips.

A Pattern Writing Example

FIG. 9 illustrates the data flow for a pattern writer system. This flow will be illustrated by examining the data flow to write a rectangle 300, shown in FIG. 26, onto the photosensitive surface 121 of target 103. Rectangle 300 straddles upper frame 301 and lower frame 302 with equal amounts in each frame. The writing process will illuminate each pixel 119 on and in the interior of rectangle 300. The portion of the rectangle 300 in the upper frame 301 is the rectangle 311 defined by vertices 303 at (100,100), 304 at (200,100), 305 at (100,1FF), and 306 at (200,1FF). The portion of the rectangle 300 in the lower frame 302 is the rectangle 312 defined by vertices 307 at (100,0), 308 at (200,0), 309 at (100,FF), and 310 at (200,FF). The (X,Y) coordinates are given in hexadecimal. The pixel at 305 is adjacent the pixel at 307, and the pixel at 306 is adjacent the pixel at 308. The database 313 for rectangle 300 is divided between frames 301 and 302. The first frame of the database contains the data defining rectangle (polygon) 311, while the second frame contains the data defining rectangle (polygon) 312.

The flow of data for the pattern writing process begins when DPC2 15 reads the database for rectangle 300 from tape 17, transforms it into turnpoint polygon representation, and transfers it onto data disk 13. FIG. 27 shows the tape 17 resident database 313 in hexadecimal for rectangle 300. This data 313 begins with the control word for beginning of strip, followed by the strip ID. The rectangle 300 is in the first strip 105, so that the strip ID is zero.

Following the strip ID is the data 314 for the rectangle 311 which is the polygon in upper frame 301. Data 314 begins with the control word for beginning of frame, which is followed by the frame ID. Upper frame 301 is the first frame in the strip so the frame ID is zero. The next data word is the beginning of rectangle (polygon) control word 8107 hex. Bits 0–5 equals 07 hex for rectangle. Bit 8 equals 1 to indicate that the bottom side of the rectangle 311 is on the frame boundary 318, and is in common with the rectangle 312 in the next frame, frame 302. The beginning of rectangle control word is followed by the X coordinate and then the Y coordinate of vertex 305. The Y coordinator is followed by the database rectangle width which is defined to be the actual width 316 minus one pixel. Actual width is 101 hex, so that the database rectangle width is 100 hex. The database rectangle height 0FF hex is defined to be one pixel less than the actual height 317, which is 100 hex. The database rectangle height is followed by the end of frame control word, which is followed by the frame ID, which is zero for the first frame.

The data 315 for the rectangle 312 in the second frame 302, is similar to the data for the rectangle 311 in the first frame 301. The beginning of rectangle control word 8407 hex has bit 10 equal to 1 to indicate that the top side of the rectangle 312 is on the frame boundary 318 and is in common with the rectangle 311 in the previous frame, frame 301.

The data 315 for rectangle 312 is followed by the end of strip control word, which is followed by the end of target control word.

Data Disc 13 Resident Database

DPC 2 15 transforms the tape 17 resident database into a turnpoint polygon representation and sends it to data disk 13, as shown in FIG. 9. FIGS. 29 and 30 are listings of the data disk 13 resident database for rectangle 300. FIG. 28 is a table listing the control words inserted by DPC2 into the database during transformation of the tape 17 resident database into the disk 13 resident database.

The turnpoint polygon representation of the database on data disk 13 consists of 16 bit words of two types, control words, listed in FIG. 28, and data words. As seen in FIG. 28, if bit15 of a database word equals 1, this indicates that that word is a control word. Bit15 equal to 0 indicates a data word. Bit14 is used in the Polygon Start Indicator control words, to designate that the following polygon data is reference data if bit14 equals 1, or is guard band data if bit14 equals 0.

The Beginning of Target control word occurs once at the beginning of the target database. This control word is followed by a 16 bit word identifying the target.

The Beginning of Strip control word occurs at the beginning of each group of 16 bit words describing a strip 105. This control word is followed by a data word which is the strip number. Strips are numbered from left to right on a target surface 121 beginning with zero.

The Beginning of Frame control word occurs at the beginning of each group of 16 bit words describing the polygons within a single frame 106. This control word is followed by a 16 bit data word identifying the frame by number. Frames are numbered from top to bottom within a single strip 105, beginning with zero.

The Polygon Start Indicator control word occurs at the beginning of each group of 16 bit data words defining a convex, in the X direction, polygon. In the present example, that polygon is a rectangle 311 or 312.

The Polygon Start Indicator control word is followed by the X-Y coordinate pairs of each turnpoint of the polygon. A polygon turn point is a vertex of the polygon, that is, it is the point at which two sides of the polygon meet at a non-zero, non-180 degree angle. For each pair of X-Y coordinates, the 16 bit X coordinate is followed by the 16 bit Y coordinate. There is a polygon X-Y coordinate pair for each turnpoint of the polygon, and the pairs appear in counter-clockwise order, beginning with the same X-Y pair that appeared in the tape 17 database representation of the polygon. Convex, in the X direction, polygons defined within a frame may be reference polygons which define the ideal polygons to be written on surface 121 or compared with an actual pattern existing on surface 121. These polygons may also be guard band polygons. Bit14 of the Polygon Start Indicator control word equals 1 if the polygon is a reference polygon, or equals 0 if the polygon is a guard band polygon.

The last pair of turnpoint X-Y coordinates is followed by the End of Polygon control word. There may be more than one polygon in the same frame, and each polygon's group of 16 bit data words begins with a Polygon Start Indicator control word and ends with an End of Polygon control word.

Following the End of Polygon control word for the last polygon in a frame 106, is the End of Frame control word. There may be, frame begins with a Beginning of Frame control word and ends with an End of Frame control word.

Following the End of Frame control word for the last frame 106 in a strip 105, is the End of Strip control word. There may be, and usually are, more than one strip 105 for a target 103. Each strip begins with a Beginning of Strip control word and ends with an End of Strip control word.

Following the End of Strip control word for the last strip 105 of target 103, is the End of Target control word. This control word signals the end of the database for the target.

FIG. 29 shows data disk resident database 319 for rectangle 300. The first 16 bit word of the database 319 is the Beginning of Target control word, followed by the target ID. Next is the Beginning of Strip control word, which is followed by the strip ID. The strip containing rectangle 300 is the first (and only) strip 105, therefore its strip ID is zero.

The strip ID is followed by the group 320 of 16 bit words for the upper frame 301. This group of words begins with the Beginning of Frame control word, which is followed by the Frame ID. The frame ID is zero since this frame 301 is the first frame in the strip. After the frame ID comes the Polygon Start Indicator. Bit 14 of the Polygon Start Indicator is 1 to signify that the X-Y coordinate pairs to follow are the turnpoints of a reference polygon, rather than those of a guardband polygon. The four X-Y coordinate pairs are the coordinates of the turnpoints 305, 306, 304 and 303, shown in FIG. 26. The four turnpoints appear in counterclockwise order around the rectangle, beginning with turnpoint 305. Turnpoint 305 is the vertex appearing in the tape 17 resident database 313. Following the coordinates for the last turnpoint of rectangle 311, is the End of Polygon control word, which is followed by the End of Frame control word.

As seen in FIG. 30, following the group 320 of 16 bit Words for frame 301, is the group 321 of 16 bit words for frame 302. The only difference between the two groups of words are the frame ID and the turnpoints.

The disk resident database 314 ends with the End of Target control word, which is preceded by the End of Strip control word.

DPC3 to Preprocessors

As shown in FIG. 9, the data disk 17 resident database 319 is read from the disk by DPC3 14, transformed into two groups of 25 bit words 324 defining the rectangle 300, and output down Pipeline A 322 and Pipeline B 323. The first group 325 of 25 bit words represents frame 301, and is sent down Pipeline A 322. The second group 326 of 25 bit words represents frame 302, and is sent down Pipeline B 323. If there was a third frame, the group of words representing that frame would be sent down Pipeline A 322 after the group representing the second frame 302 had been sent down Pipeline B. The groups of words representing contiguous frames are never sent down the same pipeline. With an embodiment having two pipelines as in this example, the first group goes down pipeline A, the second down Pipeline B, the third down Pipeline A, and so on, alternating between pipelines. The group of words for every other frame goes down the same pipeline. Some embodiments of the invention have more than two pipelines, for instance, four, in which case, the group of words for every fourth frame goes down the same pipeline. In this manner, the burden of data processing downstream of DPC2 can be distributed and the downstream data processing can be carried out in parallel by as many pipelines as are in the embodiment. This allows for faster real-time pattern writing or inspection.

As shown in FIG. 31, in the group 325 of words representing frame 301, the first 25 bit word in a group is a Move To control word. This control word signifies that the next two 25 bit words will be the X and Y coordinates, in that order, for the first polygon turnpoint. In this example, the polygon is rectangle 311 and the first turnpoint is vertex 305 shown in FIG. 26. The first turnpoint is the same vertex whose coordinates were given in tape 17 resident database 313. The next 25 bit word is a Draw control word. This control word signifies that the next two 25 bit words will be X and Y coordinates, in that order, of a turnpoint which is not the first turnpoint. The remaining two turnpoints of rectangle 311 follow in the same manner, with their X-Y coordinate pairs each following a Draw control word, as shown in FIG. 31. As before, the turnpoints are ordered in a counterclockwise fashion with respect to the periphery of rectangle 311, following the first turnpoint 305. The last X-Y coordinate pair is followed by an End of Polygon control word, which is, in turn, followed by an End of Frame control word. The 25 bit words for group 325 are sent one-at-a-time, starting with the Move To control word, down Pipeline A 322. Turning to FIG. 6, it can be seen that the output bus 52 from DPC3 14 to Pipeline A 322, and the output bus 51 from DPC3 to Pipeline B 323, are each 25 bits wide. This allows a 25 bit word-at-a-time to be output down a pipeline.

The second group 326 of 25 bit words, which represents frame 302, is indicated in FIG. 31 at 326. This group is constructed in similar fashion to the first group 325. The differences being that the coordinates of the turnpoints represent the rectangle 312 in frame 302, and the last 25 bit word in the group is an End of Strip control word. There is no end of target control word since that information is not needed downstream in the pipelines of DpC3. DPC3 monitors the data being read from data disk 13 and acts upon receiving the end of target control word in the data being read from the disk.

Preprocessor to Figure Filler

The 25 bit words sent down Pipeline A 322 by DPC3 are received by Preprocessor1, indicated at 20A, and the 25 bit words sent down Pipeline B 323 by DPC3 are received by Preprocessor2, indicated at 20B. A Preprocessor transforms the turnpoint representation of a polygon, received from DPC3, into one or more left side vectors and one or more right side vectors. These vectors define the left and right limits of the polygon, so that all pixels between or on the vectors will be included in a bit map created by the downstream Filler module 23A or 23B, of pixels to be illuminated by the laser beam. A pixel is considered to be between the left and right vectors if the pixel lies between points on the left and right vectors having the same Y coordinate as the pixel.

Figure 33:
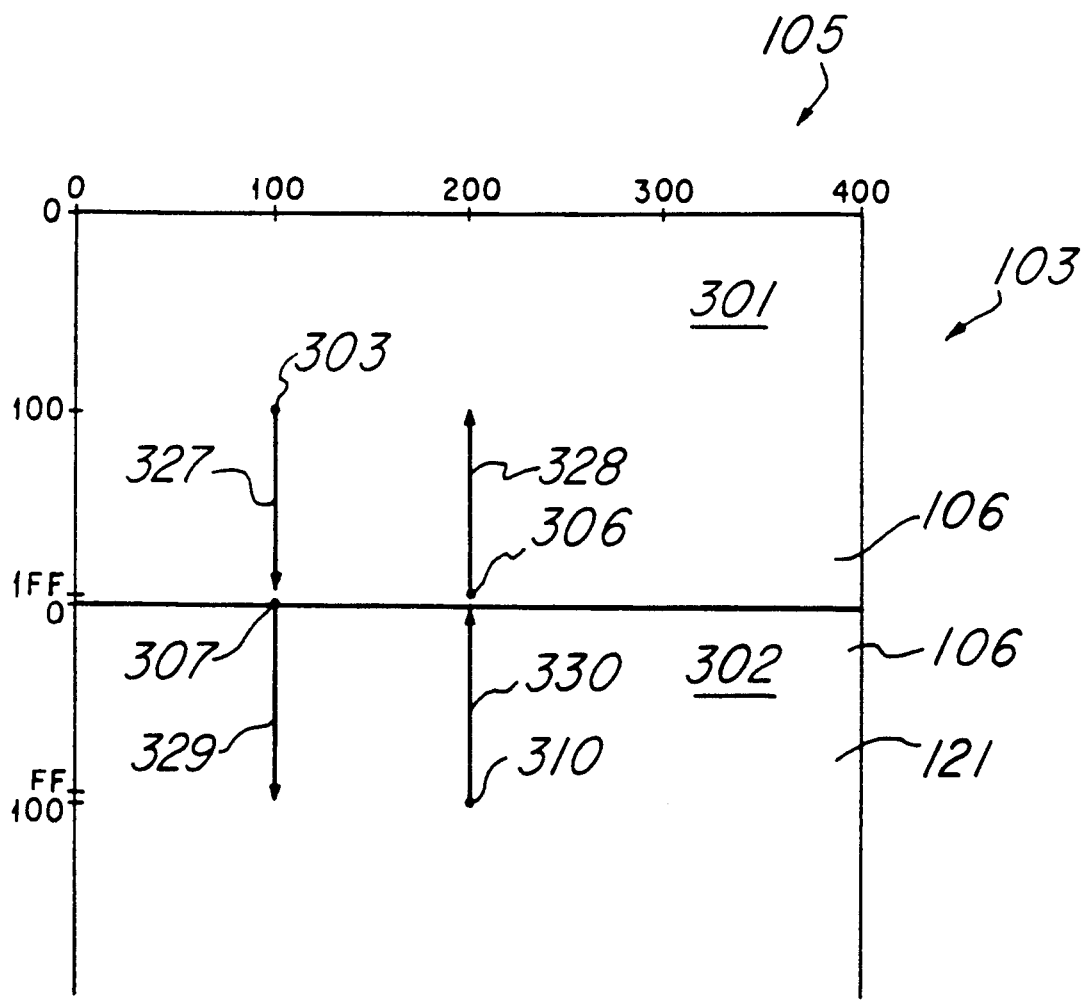
FIG. 33 is a plan view of one strip and two frames showing the vector form of the example pattern of FIG. 26.

FIG. 33 illustrates the left vector 327 right vector 328 representation of rectangle 311, and the left vector 329 right vector 330 representation of rectangle 312. In the case of a polygon which is a rectangle, the left and right vectors are each single vertical vectors, as shown in FIG. 33. It is understood, however, that there are many polygons which would require two or more left vectors and/or two or more right vectors. With a rectangle, the right vector is considered to point upwards, with the vector origin at the lower right turnpoint. This is shown in FIG. 33 where right vectors 328 and 330 have vector origins at turnpoints 306 and 310, respectively. The left vectors 327 and 329 point downwards, with origins at turnpoints 303 and 307. respectively. The direction in which the vectors point distinguishes the right vectors from the left vectors.

The Preprocessors 20A and 20B each transform the 25 bit word turnpoint polygon representations from DPC3 14, into 22 bit word left and right vector representations of the polygons. The general sequence of 22 bit words used to represent a single polygon is shown in FIG. 34. Words 350 through 355 is the general sequence of words used to describe a single vector.

The slope code NN in word 350 designates which of five possible ranges the slope of the vector falls. A vector can be horizontal, in which case there is no need to represent it in the data. If NN is equal to 04, then the absolute value of the slope of the vector is greater than one. If NN equals 07, then the vector is vertically oriented. If NN is equal to 08, then the absolute value of the slope of the vector is equal to one. If NN is equal to 09, then the absolute value of the slope is less than one. For word 350, the value in the data field 334 is termed the vector length. If NN is equal to 07, 08 or 09, then the vector length represents the Y component of the length of the vector being described. If NN is equal to 04, then the vector length represents the X component of the length of the vector being described.

If NN in word 350 is equal to 04 or 09, then all the words 350–355 are used to describe the vector.

Word 351 contains only data. If NN of word 350 is equal to 08 or 09, then the data field 334 of word 351 represents the X component of the length of the vector being described. If NN is equal to 04, then the data field 334 of word 351 represents the Y component of the length of the vector being described.

Word 351 is not used if NN of word 350 is equal to 07. That is, the vector is vertical and there is no X component of its length. This is the situation illustrated in FIG. 32 in which all left and right vectors are vertical.

Word 352 contains only data. The data field 334 of this word is the X coordinate of the origin of the vector. This word is used for all values of NN in word 350.

Word 353 contains only data. The data field 334 of this word is the Y coordinate of the origin of the vector. This word is used for all values of NN in word 350.

Word 354 contains only data. The data field 334 of this word is 0001 if the vector points to the right of vertical, and is FFFF if the vector points to the left or vertical. This word is not used when NN equals 07. That is, when the vector is vertical it points neither left nor right, so the word is not needed. This word is used for the other values of NN.

Word 354 is not used if NN of word 350 is equal to 07. That is, the vector is vertical and points neither to the left nor the right. Therefore, there is no need of this word.

Word 355 contains only data. The data field 334 of this word is 0001 if the vector points below the horizontal, and is FFFF if the vector points above the horizontal. This word is used for all values of NN in word 350.

There are as many sets of the sequence of words 350–355, as there are vectors for an individual polygon. After the last sequence of words 350–355 for an individual polygon, comes word 356. Word 356 includes a 02 in the command field, which indicates the end of the vector data for that polygon. The data field 334 of word 356, gives the minimum Y value for the polygon. The next word, word 357, contains only data The data field 334 of this word gives the maximum Y value for the polygon. The minimum and maximum Y values for a polygon are used downstream by one of the Filler Modules 23A and 23B to speed up the process of bit-mapping the polygon. The Filler Module can skip right to the first Y value used by a polygon without having to scan a large amount of data to determine where the first polygon in a frame begins. Likewise, the Filler Module knows from the maximum Y value when it is through scanning data for a frame, and time is saved.

The sequence of words 350–355 is repeated as many times as there are vectors in an individual polygon, then terminating with words 356 and 357. The complete sequence of multiple subsequences of words 350–355, plus the final words 356 and 357, is repeated as many times in a frame 106 as there are individual polygons.

Figure 32:
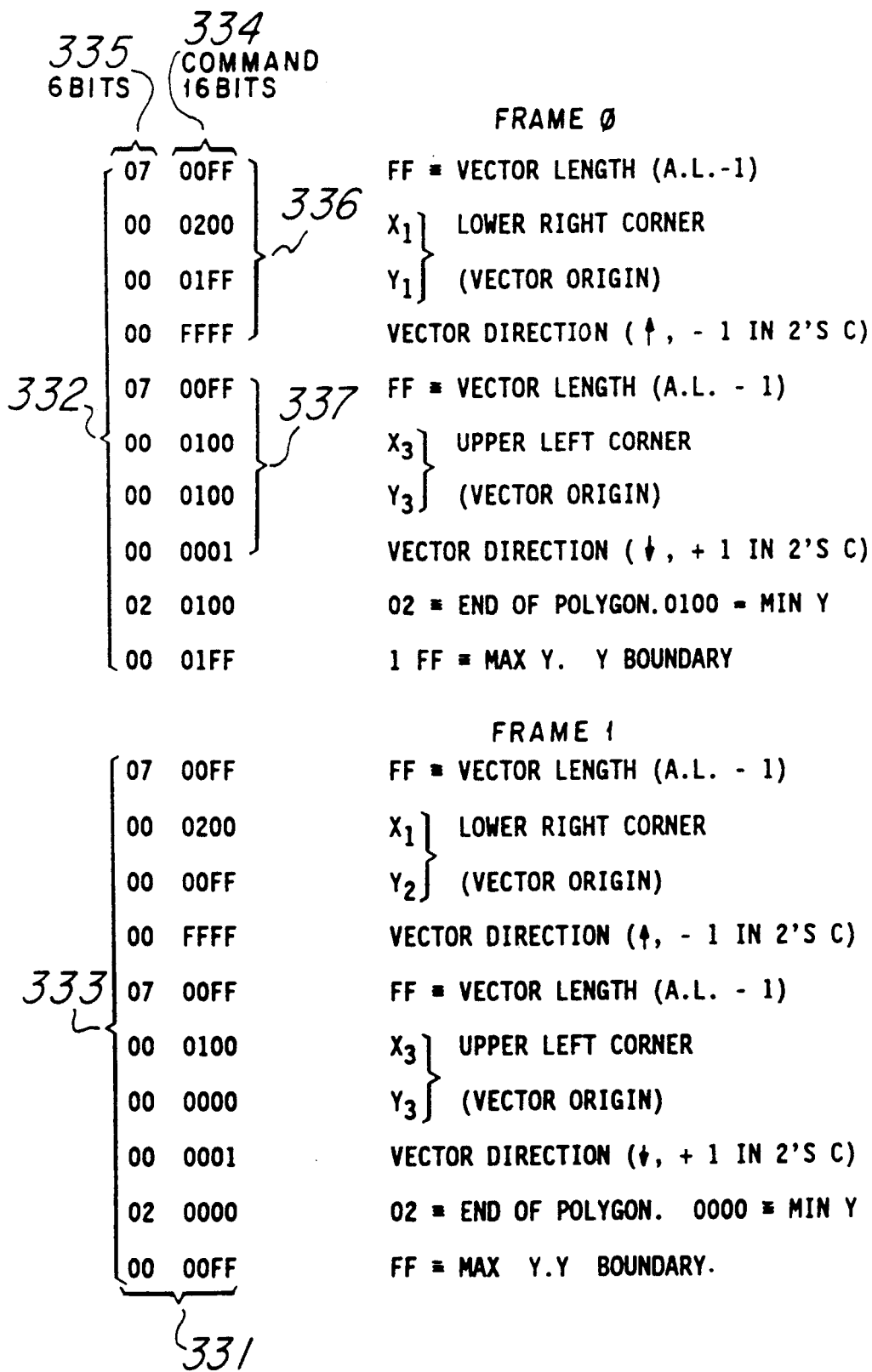
FIG. 32 is a listing of the data output by the preprocessors for the example pattern of FIG. 26.

FIG. 32 is a listing 331 of the 22 bit words giving left and right vector descriptions of rectangles 311 and 312. The sequence of 25 bit words 332 describe rectangle 311 in frame 301, and the sequence of words 333 describe rectangle 312 in frame 302.

Sequence 336 and sequence 337 of 22 bit words describing the right vector 328 and the left vector 327, respectively, each require the use of words 350, 352, 353 and 355, shown in FIG. 34. The first word in sequence 336 gives a vector length of FF hex, which is defined as being one pixel less than the actual length 100 hex. 100 hex is the length of the vector as well as being the Y component of the length of the vector, since the right vector 328 is vertical. The following word gives the X address of the origin of vector 328, and the next word gives the Y address of the origin. The last word is sequence 336 gives the vector direction, which signifies that vector 328 is pointing upwards. Sequence 337 defines left vector 327 in similar fashion.

Following sequence 337, is the 22 bit word signifying the end of left and right vector data, and also giving the minimum Y value for rectangle 311, of 100 hex. The last word in the sequence 332 gives the maximum Y value for rectangle 311, of 1FF hex. This word also ends the description of frame 301.

Sequence 333 is output by Preprocessor2 20B to Filler Module 2 23B, and defines the rectangle 312 for frame 302. Sequence 333 is structured in similar fashion to sequence 332, and can easily be understood from the explanation of sequence 332.

Figure Filler to Pixel Memory

The 22 bit words 331 sent from Preprocessor1 to Filler Module1 23A and from Preprocessor2 to Filler Module2 23B, are transformed from vector representations of polygons within frames 106, to bit-mapped, filled-figure representations. The bit-mapped, filled-figure representations of the polygons are output from the Filler Modules as groups of 25 bit Filler words 339 which are received by the Pixel Memory Modules. As seen in FIG. 9, the 25 bit Filler words 339 output by Filler Module1 23A are received by Pixel Memory Module1 24A, and the Filler words 339 output by Filler Module2 23B are received by Pixel Memory Module2 24B.

Figure 35:
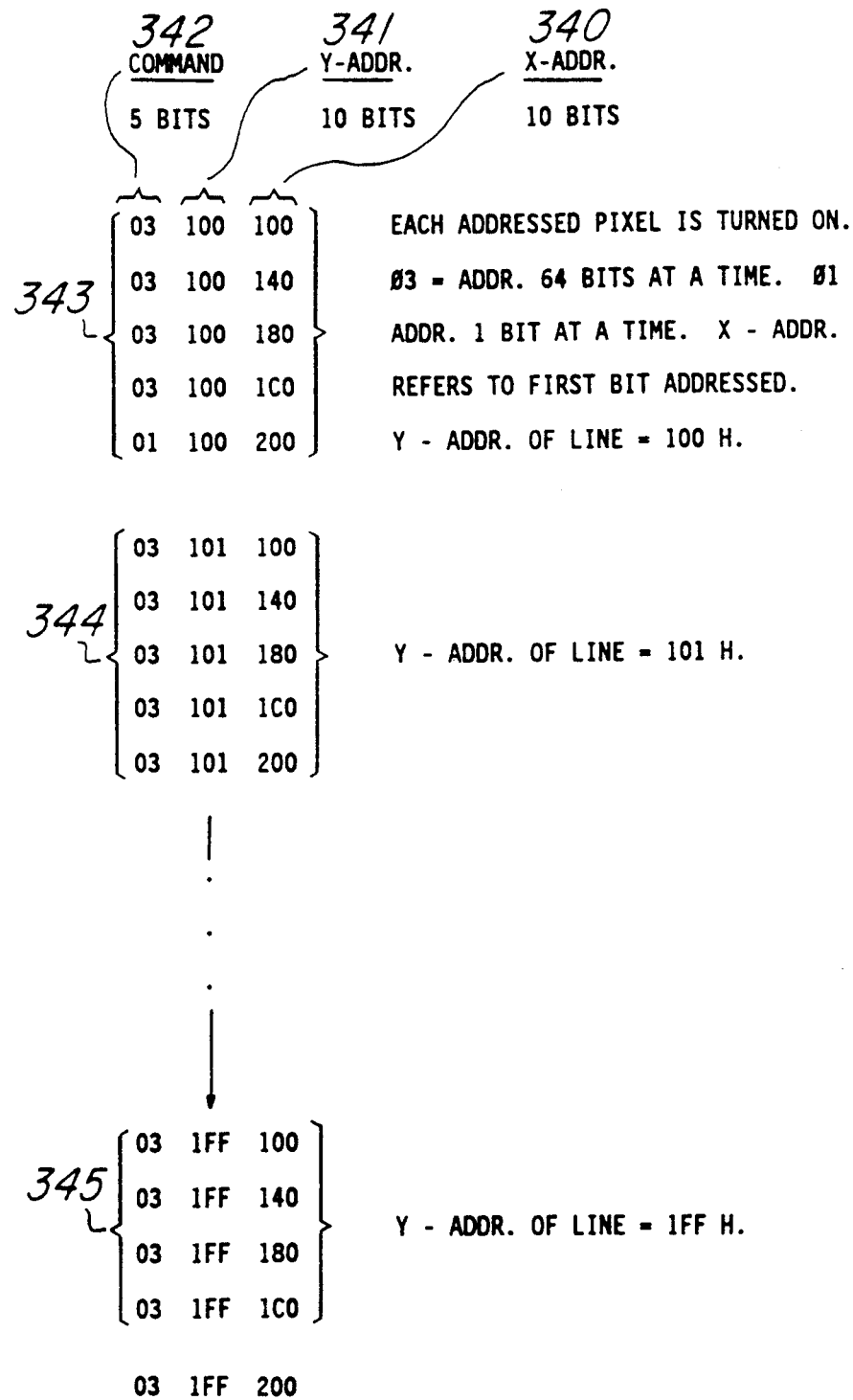
FIGS. 35 and 36 are listings of the data output by the filler modules for the example pattern of FIG. 26.

A Filler Module generates a bit-map of a frame 106 by indicating the X-Y coordinates (addresses) of all the pixels 119 on and in the interior of each polygon within a frame 106. For each row 120 of 1024 pixels in a frame, the X-Y coordinates of each pixel which lies on or in a polygon, is indicated by one or more of the 25 bit Filler words 339. If a pixel 119 does not lie in or on a polygon, then there will be no 25 bit word to indicate its X-Y coordinates. It is the pixels whose X-Y coordinates are indicated that subsequently will be illuminated by the laser beam as it raster scans across the rows 120. During inspection, it is these coordinates which will be compared with the actual pattern on the target 103. If the X-Y coordinates of a pixel are not indicated, then that pixel does not lie on or within a polygon. A single 25 bit Filler word can indicate the X-Y coordinates of all the pixels in a group of 1, 16 or 64 adjacent pixels, by giving the X-Y coordinates of the left-most pixel in the group. All of the pixels in one of these addressed groups will be in the same row 120. As can be seen in FIG. 35, the X coordinate is given as a hexadecimal number in bits 0–9, the X coordinate field 340 of the 25 bit Filler word. Bits 10–19, the Y coordinate field 341, contain a hexadecimal number which is the Y coordinate of the row in which the addressed group of pixels is to be found. Bits 20–24, the command field 342, are control bits conveying command or control information.

The command field 343 of one of the 25 bit words 339, is used to indicate whether that word is a command word and its meaning, or it indicates the meaning of the X coordinate field 340 and the Y coordinate field 341 of that word. For example, 16 hex in the command field 342 indicates that that word is a command word meaning that the end of a frame 106 has been reached. The end-of-frame command word is the last 25 bit word in a group of 25 bit words describing the polygons in a single frame.

01 hex in the command field 342, indicates that the X and Y coordinate fields of that word contain the X and Y coordinates of the leftmost pixel in a group consisting of one pixel. 02 hex in the command field 342, indicates that the X and Y coordinate fields of that word contain the X and Y coordinates of the leftmost pixel in a group consisting of 16 adjacent pixels in a single row 120. 03 hex in the command field 342, indicates that the X and Y coordinate fields of that word contain the X and Y coordinates of the leftmost pixel in a group consisting of 64 adjacent pixels in a single row. Thus, if fewer than 16 pixels lie on or in a polygon, the bit-map is constructed by addressing each such pixel with a word whose command field 342 contains 01 hex. Likewise, groups of adjacent pixels between 16 and 63 in number, are addressed by combinations of 25 bit words that each address 1 or 16 adjacent pixels. For example, 35 adjacent pixels in a row could be addressed by any combination of two 25 bit words whose command field is 02 hex, and three 25 bit words whose command field is 01 hex. For groups of adjacent pixels greater than 64 in number, 25 bit words whose command field contains 03 hex would be used in combination with words whose command field 342 contains 02 hex and words whose command field is 01 hex, as necessary to add up to the total number of pixels needing to be addressed. Only adjacent pixels are possible to address with a single 25 bit word. If two pixels are in the same row but are separated by one or more pixels that do not lie in or on a polygon, then those two pixels cannot be addressed by the same 25 bit word.

In each row 120 the Filler Modules 23A and 23B each process the left and right vectors to determine the leftmost pixel which must be addressed and the rightmost pixel which must be addressed, by the 25 bit words 339. The leftmost pixel in a given row will correspond to the intersection point of a left vector with the row (only one left vector per polygon will intersect any given row). Similarly, the rightmost pixel in the same given row will correspond to the intersection point of a right vector with the row (only one right vector per polygon will intersect any given row). Pixels 119 are located at discrete points along a row, thus, each vector probably will actually intersect any given row at a position which is somewhere between, rather than coinciding with, one of two adjacent pixels. If the actual point of intersection does not coincide with a pixel position, the Filler Modules execute Bresenham's Line Algorithm to determine which of the two adjacent pixels is nearest to the actual point of intersection. The nearest pixel's X-Y coordinates will be stored as being the given row's leftmost (or rightmost, as appropriate) pixel address. Bresenham's Line Algorithm is well-known in the art, and among other places, can be found at Page 433–435 of the text "Fundamentals of Interactive Graphics", by J. D. Foley, published by A. Van Dam, 1982, which by reference is incorporated herein. In the example illustrated in FIGS. 26 and 33, the left vector 327 and the right vector 328 each have row intersection points which all coincide exactly with pixel positions.

FIG. 35 is a list of the 25 bit data words 339 for bit-mapping the rectangle 311 in frame 301. This frame of words is output by Filler Module1 23A to Pixel Memory Module1 24A. As can be seen from FIGS. 26 and 32, rows 119 having Y coordinates of 000 through 0FF hex, do not contain any pixels lying on or within the rectangle 311. In other words, none of the pixels in those rows lie on or between left vector 327 and right vector 328. Therefore, there are no 25 bit words with a Y coordinate of 000 through 0FF hex.

The first row to have pixels 119 on or within rectangle 311, is the row having a Y coordinate of 100 hex. These pixels comprise the pixels corresponding to the turnpoints 303 and 304 and all pixels in that row in between the turnpoints. Turnpoint 303 has coordinates X=100 hex and Y=100 hex, and is the first pixel in that row whose coordinates are indicated by one of the 25 bit words 339. As seen in FIG. 35, the group 343 of five 25 bit words indicates the X-Y coordinates of the first row of pixels for rectangle 311. That row has a Y coordinate equal to 100 hex, and the leftmost group of 64 pixels in that row has the X coordinate of the leftmost pixel in that group given as 100 hex in the X coordinate field 340 of the first 25 bit word in group 343. The Y coordinate field 341 contains 100 hex, which is the Y coordinate of each pixel in the leftmost group.

The second 25 bit word in group 343 gives, in the X coordinate field 340, the X coordinate of the leftmost pixel of the second group of 64 pixels. This X coordinate is 140 hex and is 40 hex (64 decimal) greater than the X coordinate 100 hex of the previous group of 64 bits. Likewise, the next two 25 bit words give the X coordinates of the next two groups of 64 pixel groups.

The first four 25 bit words in group 343 each have 03 hex in the command field 342 to indicate that the X-Y coordinates given are of the leftmost pixel in a group of 64 pixels.

The fifth and last 25 bit word of group 343 has a −01 hex in its command field 342, indicating that this word will give the coordinate of the leftmost pixel in a group consisting of a single pixel. This 25 bit word completes the addressing of all the pixels of the Y=100 hex row. All five 25 bit words in group 343 have 100 hex in their Y coordinate fields. The first four 25 bit words of group 343 each address 40 hex pixels, so the four words together address 100 hex pixels. The fifth word addresses one pixel, giving a total of 101 hex pixels for each row of rectangle 311. This may also be seen in FIGS. 26 and 33.

The group 344 of five 25 bit words address the 101 hex pixels in the next row, where Y=101 hex. This group 344 of five words is structured in similar manner to the first group 343.

FIG. 35 does not show the groups of 25 bit words for Y=102 hex through Y=1FE hex, but they are structured in similar manner to groups 343 and 344.

The last group 345 for frame 301 is shown in FIG. 35 and is similar in structure to the groups 343 and 344. All five words in group 345 have 1FF hex in their Y coordinate field.

The last 25 bit word in the group 339 of words defining the rectangle 311 in frame 301, has a 16 hex in its command field 342. No data is contained in the Y coordinate field 341 or in the X coordinate field 340. This word is a control word indicating the end of the 25 bit words for the frame.

Figure 36:
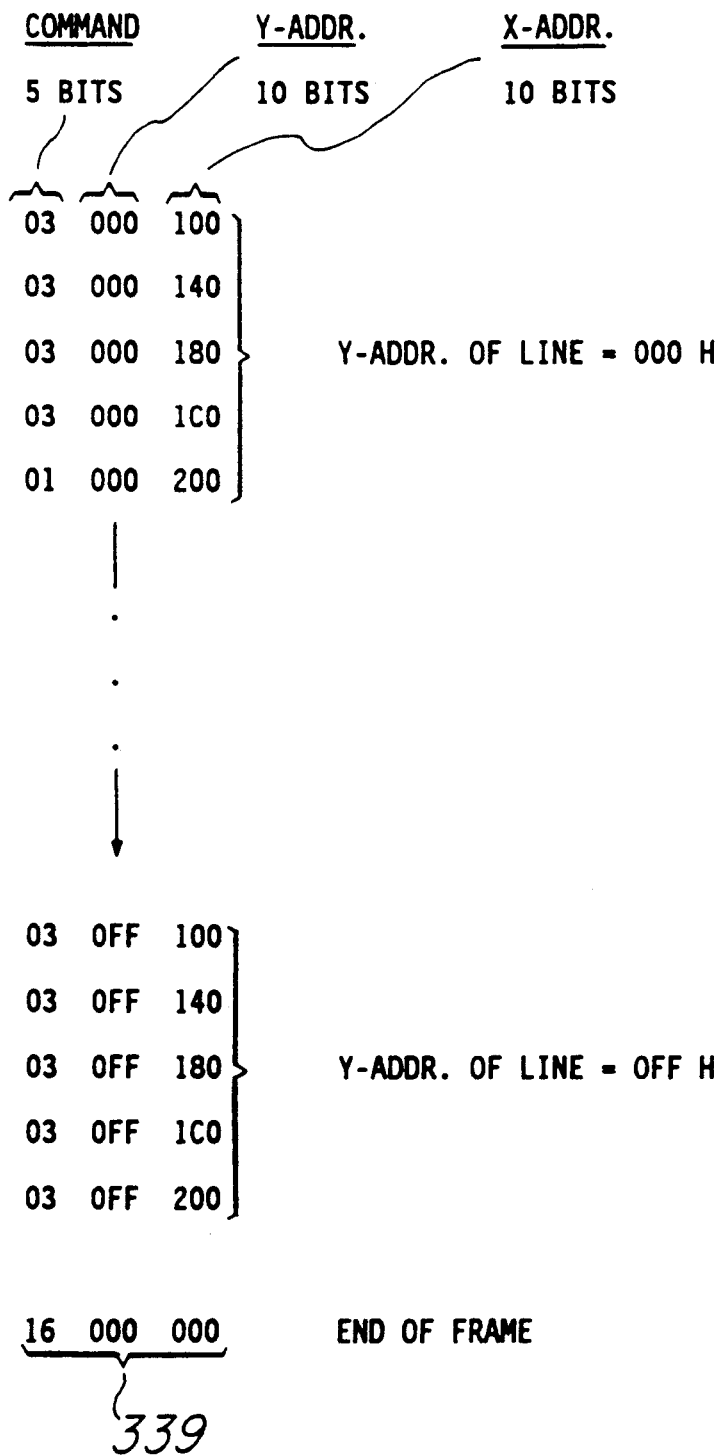

FIG. 36 shows the 25 bit words 339 output by Filler Module2 23B to Pixel Memory Module2 24B, describing rectangle 312 in frame 302. The structure of these 25 bit words is similar to those shown in FIG. 36. The only difference is that the words shown in FIG. 36 are for rows 120 ranging in Y coordinates from 000 hex to 0FF hex.

Pixel Memory Modules to High Speed Laser Interface Module

FIG. 37 shows the final bit-map 347 of the entire frame 301, including the pixel locations which are not to be illuminated by the laser beam as it raster scans the rows of the frame. The bit-map shown in FIG. 37 resides in the output memory of Pixel Memory Module1 24A, as a sequence of 64 bit words at memory addresses 346. The sequence of 64 bit words is output from the output memory to the High Speed Laser Interface Module 27. Each 64 bit word is output in parallel on a 64 bit bus to Module 27. The ECL High Speed Laser Interface Module 28 receives the 64 bit words from Module 27, and produces a serial bit stream by using a shift register to do parallel to serial conversion of the 64 bit words. The serial bit stream is input by the Vendor Laser Scan Electronics 348, which is a part of the Electro-optical/Acousto-optical laser optical system 37. The serial bit stream is used by the Vendor Laser Scan Electronics 348, and specifically the electro-optical modulator 101, to modulate a laser beam to illuminate selectively pixels on target 103. The laser beam raster scans every pixel position on target 103, and if the electro-optical modulator 101 receives a bit equal to one when the beam is over a given pixel position, then that pixel will be illuminated by the laser beam. If the bit received by the electro-optical modulator 101 is a zero rather than a one, then the electro-optical modulator will turn the beam off when it is over the given pixel position.

The bit-map 347 has a bit corresponding one-to-one for each pixel on target 103 surface 121. A zero in a bit position of any of the 64 bit words of the bit-map means that the corresponding pixel on the surface 121 will not be illuminated by the laser. A one in a bit position of any of the 64 bit words of the bit-map means that the corresponding pixel on the surface 121 will be illuminated by the laser as it raster scans the pixel's position.

As seen in FIG. 37, Pixel Memory addresses 0000 hex through 0FFF hex all contain 64 bit words having a zero in every bit position. There are 1000 hex words in this portion of memory, and 40,000 hex bits. Each row 120 has 400 hex (1024 decimal) bits, therefore, 40,000/400 gives 100 hex rows represented by Pixel Memory addresses 0000-0FFF hex. Thus, the word at Pixel Memory address 1000 hex corresponds to the leftmost 64 pixels of row Y=100 hex, which is the first row in which pixels will be illuminated to construct rectangle 311 in frame 301. Since the turnpoint 303, FIG. 26, has X coordinate equal to 100 hex, the first 100 hex pixels in that row will not be illuminated by the laser. Thus, the four 64 bit words in Pixel Memory positions 1000 hex through 1003 hex will contain all zeros. The next pixel will correspond to turnpoint 303 at X=100 hex. There are 101 hex pixels from X=100 hex through turnpoint 304 at X=200 hex. Therefore, four 64 bit words plus one bit are required in which each bit position contains a one. The four 64 bit words with each bit equal to one are the words in Pixel Memory addresses 1004-1007 hex. The extra bit equal to one is found in bit 63 of the 64 bit word at Pixel Memory address 1008 hex. Since the strip 105 has X addresses from 000 through 3FF hex, There are 200 hex pixels in the range X=200 hex through 3FF hex. Thus eight 64 bit words are required to describe this portion of the row Y=100 hex. The word at 1008 hex has bit 63=1, as discussed above, with bits 0-62 being zeros. The 64 bit words at addresses 1009-100F hex have zeros in all their bit positions, completing the description of row X=100 hex.

The description of row Y=101 hex begins with the 64 bit word at Pixel Memory location 1010 hex, and continues in the same manner as for row X=100 hex.

The description of rows Y=102-1FF hex will be the same as for row Y=100 hex.

The bit map for frame 302 is not shown, however, it will be structured in a similar manner to frame 301, as shown in FIG. 37. The rectangle begins with row Y=000 hex and ends with row Y=0FF hex. Rows Y=100-1FF hex do not contain any pixels in or on a polygon, therefore, all the 64 bit words describing this area of the frame 302 have zeros in all their bit positions.

PATTERN INSPECTION

Pattern Illumination and Detection

Figure 41:
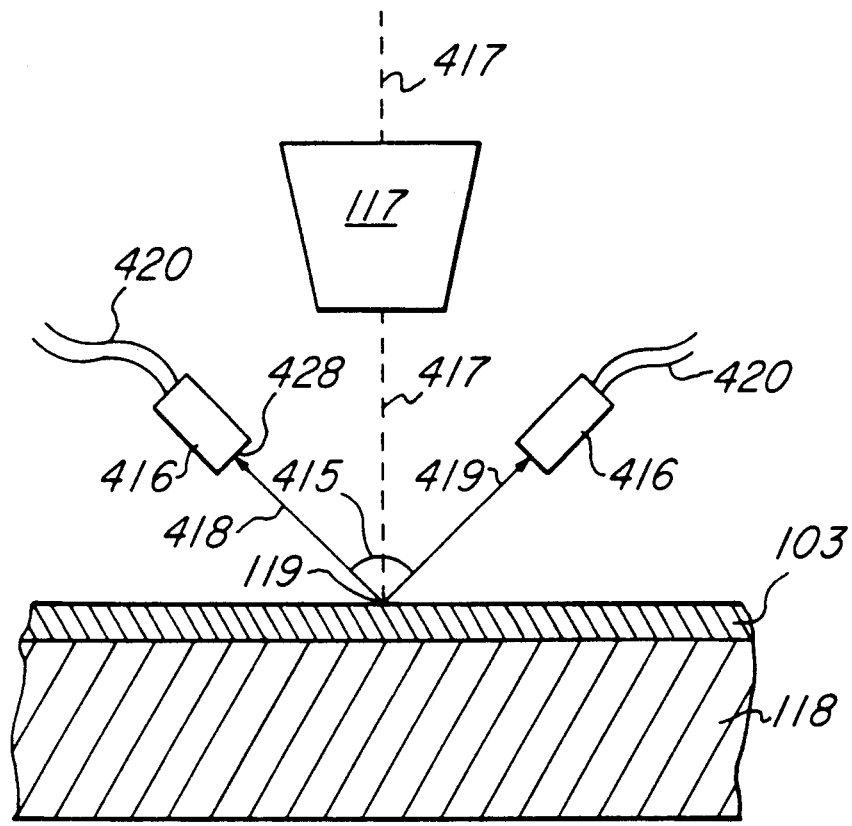
FIG. 41 is a side view of the light detection system for the pattern inspector system.
Figure 42:
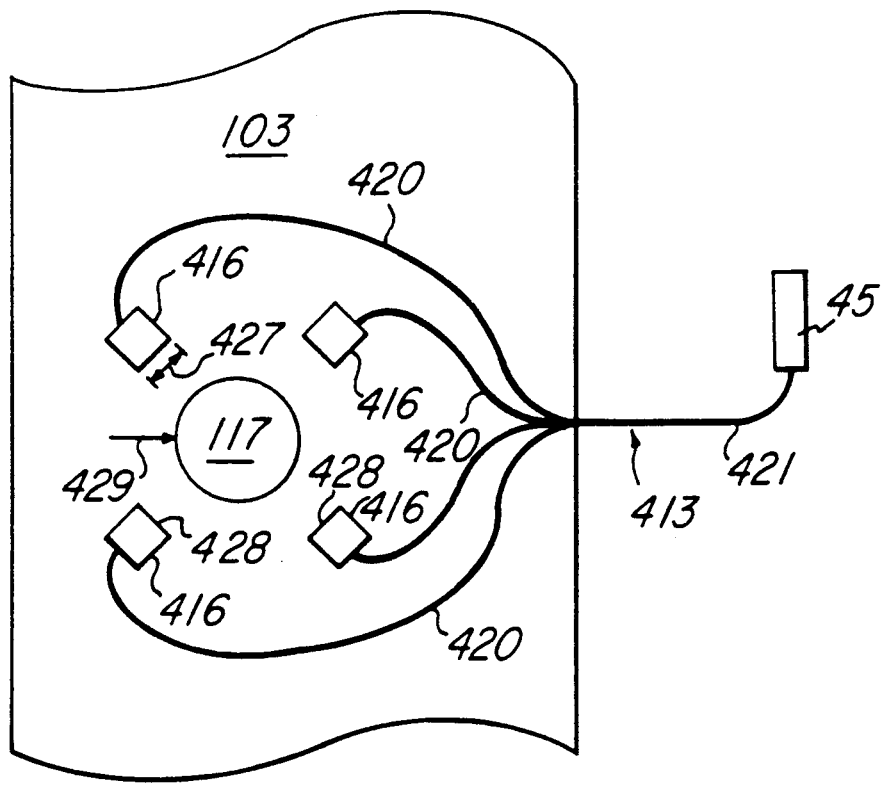
FIG. 42 is a plan view of the light detection system for the pattern inspector system.
Figure 43:
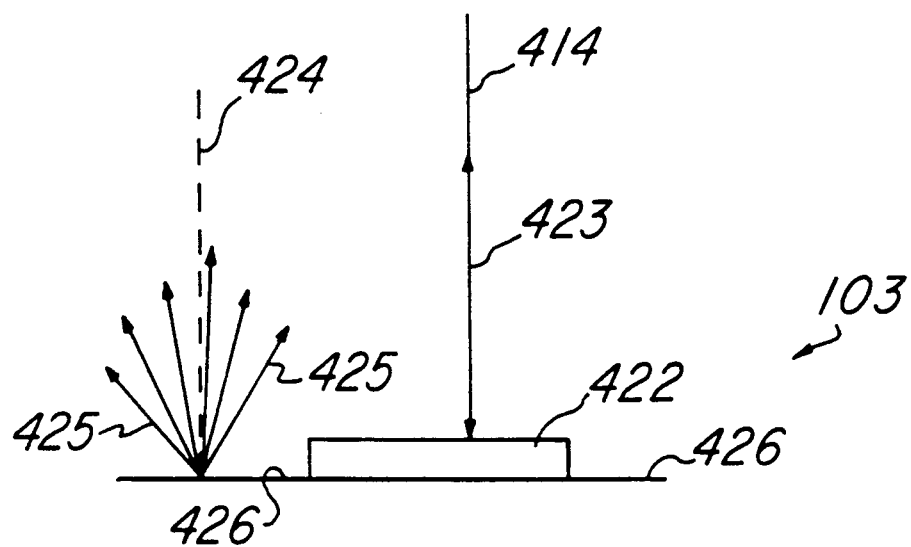
FIG. 43 is a side view illustrating specular and diffuse reflection from a target.

As seen in FIGS. 41-43, pattern inspection can be done on any target 103 having a pattern 422 on a background 426, wherein either, but not both, the pattern 422 or the background 426 specularly reflects incident laser light, and the other diffusely reflects incident laser light. Thus, optically, the pattern 422 and the background 426 differ from each other by the manner in which they reflect an incident laser beam. This means that the pattern 422 can be distinguished from the background 426 by detecting the presence or absence of laser light which has been reflected at an angle larger than would be the case with specular or nearly specular reflection. Inspection can be performed most accurately on those targets whose patterns and backgrounds differ the most with respect to specular versus diffuse reflectivity.

In the example illustrated in FIG. 43, the pattern 422 specularly reflects incident laser light and the background 426 diffusely reflects laser light. Incident laser beam 414 is normal to the surface of pattern 422 and reflects back upon itself as shown at 423. Thus, the surface of the pattern 422 is shown producing perfectly specular reflection. Incident laser beam 424 is normal to the surface of background 426 and is scattered at many angles as indicated by reflections 425. Thus, the surface of the background 426 produces diffuse reflection.

An example of a target 103 which would produce the reflections shown in FIG. 43 is a printed wiring or printed circuit board having copper circuit patterns produced by etching away unwanted copper from the face of an epoxy board which had been entirely covered with a thin layer of copper. Printed wiring boards have patterns 422 which are shiny, specularly reflective copper circuit patterns, while the background 426 is epoxy board having a diffusely reflective surface.

Another example of a target such as the one shown in FIG. 43 is an epoxy board having a thin layer of copper on its face, and photoresist patterns 422 on the surface of the copper. The photoresist had covered the copper surface entirely and was then etched away selectively to produce the photoresist pattern 422. The etching process also etches the surface of the background copper 426 sufficiently to cause the surface to reflect light diffusely. The photoresist pattern 422 has a relatively shiny surface which causes incident laser light to be reflected in a substantially specular manner.

FIGS. 41 and 42 show an arrangement of four fiber-optical detector heads 416 surrounding the objective lens 117, to detect scattered or diffusely reflected laser light. Objective lens 117 is shown in the context of the optical system in FIG. 5. The optical system shown in FIG. 5 is used in the pattern inspection system 400 as well as in the pattern writing system 50. FIG. 5 does not show the fiber-optical detector system 413.

The fiber-optical detector system 413 includes the four fiber-optical detector heads 416, the fiber-optical cables 420 which join together as cable 421, and photomultiplier tube 45. Each fiber-optical cable 420 is a circular arrangement of a plurality of individual fiber-optic fibers. Head 416 terminates cable 420 in a thin, wide, rectangular array of the individual fiber-optic fibers. The width 427 of a fiber-optic head 416 is indicated in FIG. 42. The optical aperture 428 of head 416 is the end of the thin, wide, rectangular array of the individual fiber-optic fibers, through which light is admitted to travel down a cable 420 into cable 421 and into the photomultiplier tube 45, where an analog electrical signal is generated whose amplitude indicates the intensity of the light. Fiber-optical cable 413 is a circular arrangement of the individual fiber-optic fibers from each of the cables 420. The light entering photomultiplier tube 45 is the sum of the light entering the optical apertures 428 of the four heads 416. In the example shown in FIG. 43, an electrical signal is generated by the photomultiplier tube 45 when laser beam 424 strikes background 426 and is diffusely reflected and intercepted by the apertures 428 of heads 416. When laser beam 414 strikes pattern 422, the reflected light beam 423 returns along the same path and is not intercepted by apertures 428 of heads 416, and no electrical signal is generated. The electrical signals may be inverted if desired so that the presence of a signal indicates the presence of pattern 422, and the absence of a signal indicates the absence of any pattern.

As seen in FIGS. 41 and 42, the four fiber-optical heads are radially disposed about the optical axis 417 of objective lens 117, and are located at the four vertices of a square centered upon and normal to the optical axis 417. Arrow 429 in FIG. 42 indicates the direction that a row 120 will be raster scanned by the laser beam passing through objective lens 117. A row is very short so that the angle subtended by the row will be close to zero. Thus, although the scanning laser beam will not always be quite normal to the surface of target 103, specular reflection will produce a reflected beam in which the angle of incidence plus the angle of reflection is sufficiently small to prevent the reflected beam from entering the optical aperture 428 of any of the heads 416. Each fiber-optical head 416 is aligned so that its optical aperture 428 points at the region where a laser beam will strike the surface of target 103. This can be accomplished by pointing the apertures at the point where optical axis 417 intersects the surface of target 103, as shown in FIG. 41. It is, however, not required that all the apertures point to a single point, but each may point to a distinct point somewhere along or near the row to be raster scanned.

Instead of being disposed at the vertices of a square, the four fiber-optical heads 416 may be disposed at the vertices of a rectangle.

Diagonally opposed pairs of fiber-optical heads 416 are disposed at the proper height above the surface of target 103 so that the angle 415 subtended by their distance apart is a right angle. This may be seen in FIG. 41, where reflected light beams 418 and 419 are reflected from a pixel 119 at right angles to one another, and enter the optical apertures of the two fiber-optical heads 416 shown. This angle allows the apertures 428 of the heads to be sufficiently far from optical axis 417 so that specularly reflected light will not enter the apertures 428. Also, an angle 415 of ninety degrees is small enough to optimize the interception of diffusely reflected light, if there is any. An angle of ninety degrees works well for light diffusely reflected from epoxy board or etched copper. This angle can be varied if required for optimum interception of diffusely reflected light from other types of surfaces.

The Electronics

FIG. 38 is a block diagram of a pattern inspector system 400, which also is capable of writing, as described previously. The pattern inspector system shares many of the functions of the pattern writer system 50, shown in FIG. 6. The pattern inspection system 400 is another embodiment of the invention and will be described in terms of the additions and differences with the writer.

For the most part, the blocks numbered 1-11 function as described in conjunction with FIG. 6. The host computer 3 functions to generate a command list to inspect when the system 400 is functioning as an inspector, as well as to generate a command list for writing when the system is functioning as a writer, as described in conjunction with FIG. 6. During inspection, the host computer 3 also does sorting of a received error list which identifies the X-Y coordinates of those areas of a detected pattern on the target 103 surface which are part of the detected pattern but should not be present, or those areas of the target 103 which should have patterning but in fact do not. The host computer 3 stores the X-Y coordinates of the sorted list in host memory 4.

The database resident on tape 17 for the inspection system 400 is the same as described for the writer system 50, or for the inspection system 400 when in the writer mode. At this point, the database has only reference polygons in each frame of the database. The reference polygons form the ideal patterns against which the actual patterns on the target 103 will be compared. The reference polygons also are the ideal patterns which are written on photosensitive surface 121 when in the writer mode of operation.

As with the writer system 50, DPC2 15 reads the database from tape 17 through tape drive controller 16, reformats it into turnpoint polygon representation, as before, and stores the turnpoint polygon representation of the database on data disk 13 through disk controller 12. As part of the inspection system 400, DPC2 15 also generates guardband turnpoint polygons for the reference polygons in each frame 106. The guardband polygons form a don't care zone around each reference polygon side. During inspection of an actual part, mismatches between the actual pattern on a target 103 and the ideal pattern described by the database are not flagged as errors if the mismatches occur in a don't care zone, i.e., within a guardband polygon. The guardband around each reference polygon side will be narrow enough so that unsatisfactory patterns will not be passed as being good, and wide enough so that insignificant variances between the ideal pattern and the actual pattern, will not cause the pattern on the target to be rejected unnecessarily.

Each side of a polygon is a line segment completely contained within a single frame 106. Preferably, a guardband polygon is a rectangle surrounding the line segment, such that the perpendicular distance from any point on the line segment to the nearest point on the guardband rectangle, is a fixed, small distance epsilon. Typically, epsilon will be a distance equal to a small number of pixels. Thus, the guardband rectangle will have two sides parallel to and equidistant from the line segment. Preferably, the other two sides of the guardband rectangle will each be a distance epsilon, measured from their midpoints, from the nearest endpoint of the line segment.

A guardband polygon will not always be a rectangle, nor will it always be exactly as previously described. When the line segment is near or on one of the frame boundaries, the distance epsilon may be greater than the distance of all or some portions of the line segment from the frame boundary. As is the case with reference polygons, a guardband polygon must lie completely within, or on, a single frame 106. Thus, any portions of the guardband rectangle which otherwise would protrude into an adjacent frame, instead are truncated by the frame boundary, and the truncating portion of the frame boundary forms one of the sides of the guardband polygon.

Figure 26:
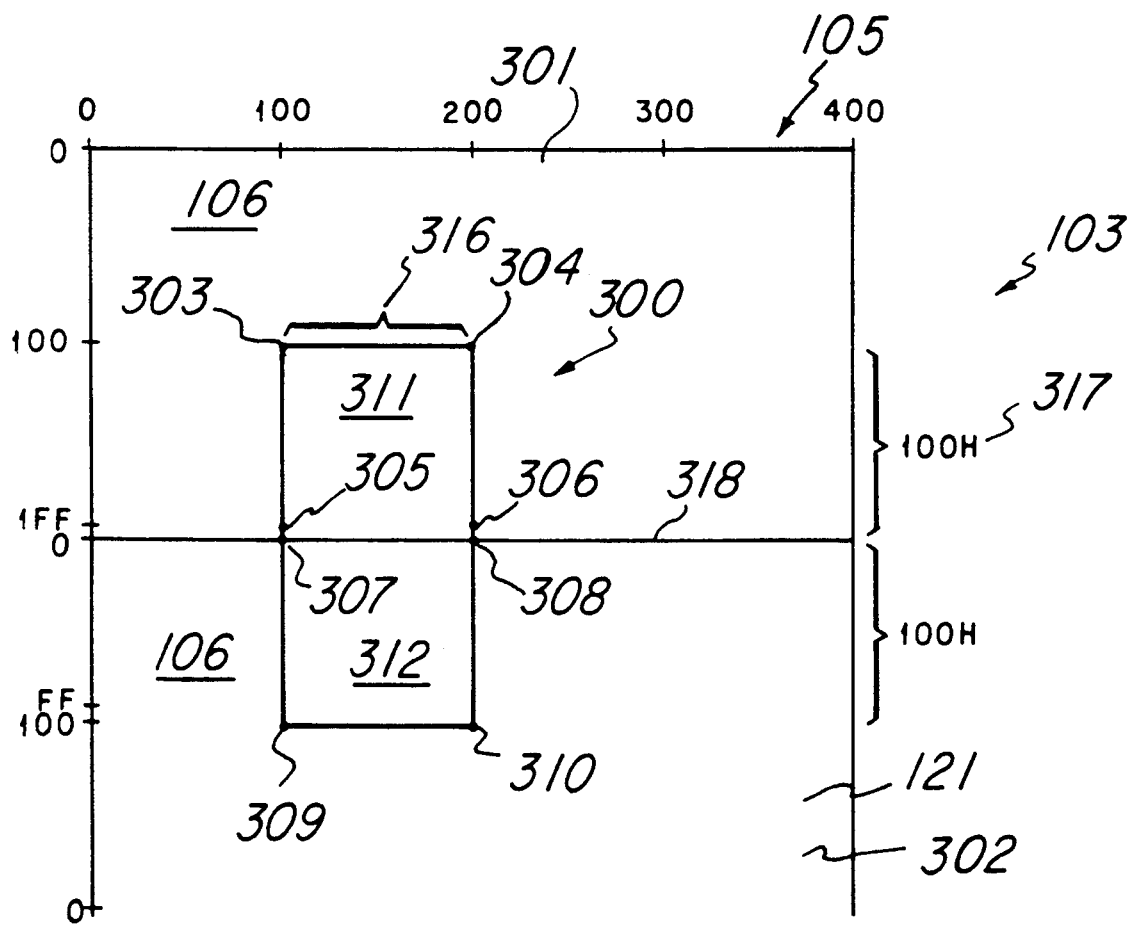
FIG. 26 is a plan view of one strip and two frames of a target, with and example rectangular pattern to be written or inspected.
Figure 47:
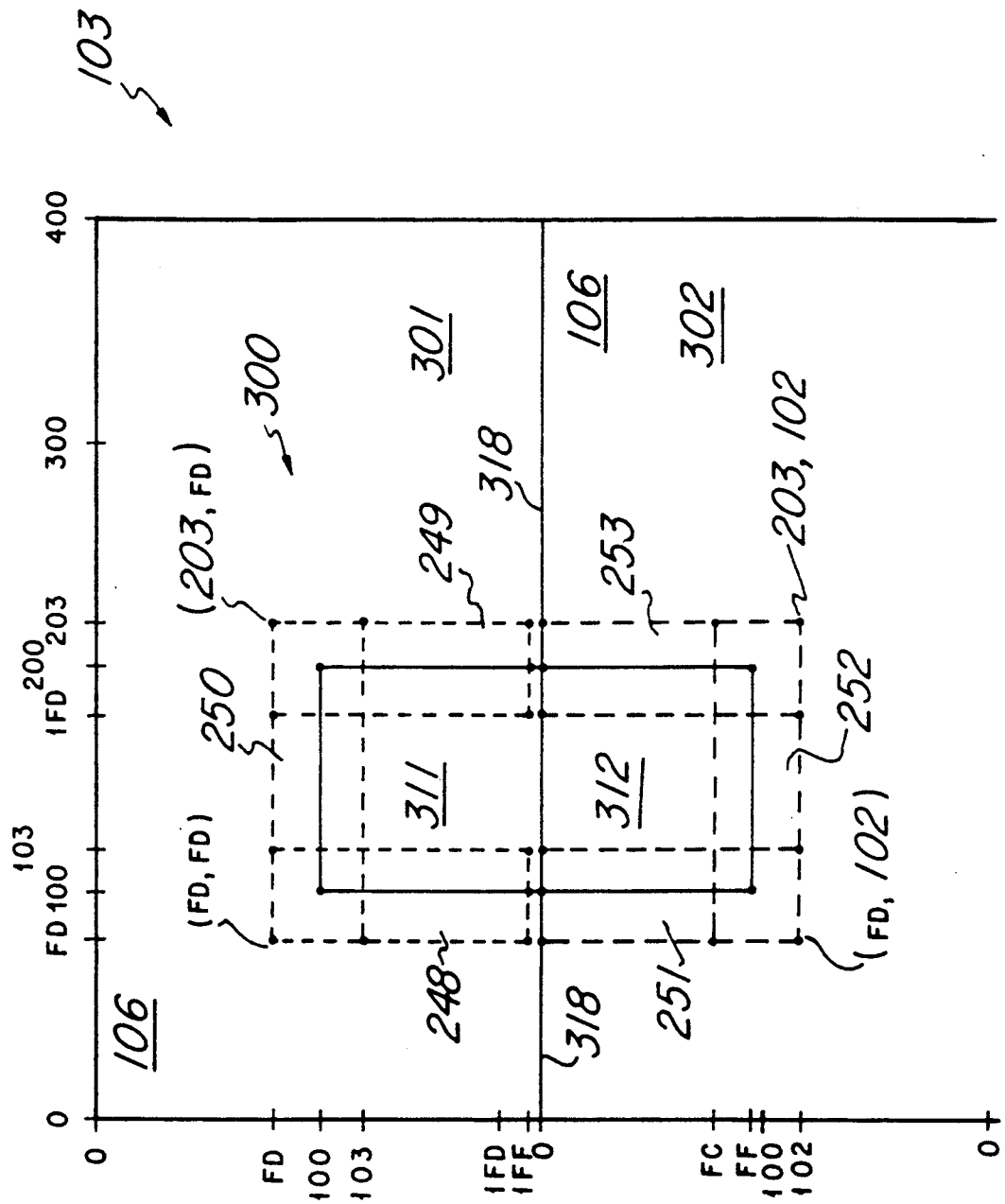
FIG. 47 is a plan view showing the rectangular pattern of FIG. 26 with guardbands surrounding its sides.

FIG. 47 shows the guardbands surrounding the sides of the rectangle 300, the example pattern illustrated and discussed in connection with FIG. 26. The rectangle 300 requires six guardband polygons, i.e., six guardband rectangles. Since the rectangle 300 straddles the upper frame 301 and the lower frame 302, and since guardband polygons cannot cross frame boundaries, the left and right sides of the rectangle 300 will each have two guardband polygons (rectangles) instead of only one. That is, the left side of rectangle 300 will be surrounded by guardband rectangle 248 in frame 301, and by guardband rectangle 251 in frame 302. Similarly, the right side of rectangle 300 will be surrounded by guardband rectangle 249 in frame 301, and by guardband rectangle 253 in frame 302.

The top side of rectangle 300 is completely contained within frame 301, and so, will have only one surrounding guardband rectangle 250. Likewise, the bottom side of rectangle 300 will have only one surrounding guardband rectangle 252.

In frame 301, guardband rectangle 248 extends from $X=0FD$ hex to $X=103$ hex, and from $Y=0FD$ hex to $Y=1FF$ hex. Guardband rectangle 249 extends from $X=1FD$ hex to $X=203$ hex, and from $Y=0FD$ hex to $Y=1FF$ hex. Guardband rectangle 250 extends from $X=0FD$ hex to $X=203$ hex, and from $Y=0FD$ hex to $Y=103$ hex.

In frame 302, guardband rectangle 251 extends from $X=0FD$ hex to $X=103$ hex, and from $Y=00$ hex to $Y=102$ hex. Guardband rectangle 252 extends from $X=0FD$ hex to $X=203$ hex, and from $Y=0FC$ hex to $Y=102$ hex. Guardband rectangle 253 extends from $X=1FD$ hex to $X=203$ hex, and from $Y=00$ hex to $Y=102$ hex.

As can be seen, guardband rectangles 248 and 250 overlap in the upper left corner, and guardband rectangles 249 and 250 overlap in the upper right corner. Similarly, guardband rectangles 251 and 252 overlap in the lower left corner, and guardband rectangles 252 and 253 overlap in the lower right corner.

It is seen that each of the surrounded guardband rectangles has sides spaced a distance epsilon = 3 pixels from the surrounded side of rectangle 300.

From FIG. 47, it can be seen that guardband rectangles 248 and 251, abut frame boundary 318. Together, guardband rectangles 248 and 251 completely surround the left side of rectangle 300. Guardband rectangle 248 end at Y = 1FF hex in frame 301, and guardband rectangle 251 begins at Y = 00 hex in frame 302. Between Y = 1FF in frame 301 and Y = 00 hex in frame 302, there is no gap or omitted pixel position, since Y = 1FF hex is the last Y address in frame 301. A similar situation exists with respect to guardband rectangles 249 and 253.

As with the writer system 50, DPC3 14 reads the database from data disk 13, inserts Move To and Draw commands into the database, and outputs the modified database into the pipelines. Unlike the writer system 50, however, DPC3 14 sends all the guardband words, frame-at-a-time, down the bus out1 401 to pipeline buffer1 18A, and all the reference words, frame-at-a-time, down the bus out2 402 to pipeline buffer2 18B. As with the writer system 50, alternate frames of words are sent to preprocessor3 20C and preprocessor4 20D. Similarly, frames of guardband words are alternately sent to preprocessor1 20A and preprocessor2 20B. Window clipper 19 functions as with the writer system 50. The embodiment of the inspection system 400 shown, has four pipelines which begin with the four preprocessors 20A-20D.

Preprocessors 20A-20D, filler modules 23A-23D, pixel memory modules 24A-24D, and stage controller 25 function as described for writer system 50.

The pixel memory interface module 53 functions like the high speed laser interface module 27, except that a memory buffer for the guardband words is also included. The reference and the guardband words are output to the ECL comparator 40.

The ECL comparator 40 has a shift register which converts the 64 bit reference data words from the pixel memory interface module 53 into serial reference data. Likewise, the ECL comparator 40 has a shift register which converts the 64 bit guardband data words from the pixel memory interface module 53 into serial guardband data.

Photo tube 45 receives laser light reflected from the pixels on the surface of target 103 and the pattern thereon, and converts the reflected light into an analog scan signal which is proportional to the intensity of the light received by the tube 45. An unmodulated laser beam raster scans the surface of target in the same manner as for writing. The only difference is that the laser beam is unmodulated and of a constant, predetermined intensity during inspection. The analog scan signal is amplified by amplifier 44, and the output of the amplifier is received by the ECL comparator 40. The received analog scan signal is converted by an analog-to-digital-converter to a digital representation of the reflected light intensity at a pixel on the surface of the target 103 The digital scan signal is clocked into a scan latch at the precise intervals during raster scanning so that the latched digital scan words are the digital representations of the reflected light intensity at each scanned pixel location. The digital scan word is a gray scale representation of the reflected light intensity. The digital scan word is sent to a digital comparator which compares the digital value with a predetermined, stored threshold value. If the digital scan word is greater than or equal to the threshold value, the comparator outputs a single bit which has the value of one. If the digital scan word is less than the predetermined threshold value, then the comparator outputs a single bit which has the value of zero. As the laser beam raster scans the target 103, 1024 digital scan words are clocked into the scan latch for each row scanned. Each digital scan word represents the reflected light intensity at one of the pixels in the scanned row. Thus, the comparator generates scan data comprising a serial bit stream consisting of 1024 bits for each raster scanned row, where each bit is a binary representation of the reflected light intensity at one of the 1024 pixel positions in the scanned row.

An alternate embodiment for the pattern inspector system 400 is used for inspection of patterned, transparent targets, such as film or glass photomasks or reticles. With this embodiment, the mask is inspected by transmission of laser light rather than by reflection. The back of the mask (target 103) is illuminated with a collimated uniform light source that illuminates the imaged area of the target. Imaging can be done effectively by the use of a CCD line scanner, particularly, a segmented scanner with multiple output such as the EG&G Reticon 1024 element scanner which is subdivided into eight contiguous line scanners each comprised of 128 elements. These 128 element sections are organized as even and odd serial pixel outputs. That is, during the first clock pulse, signals for the first and second pixels are output in parallel; during the second clock cycle, signals for the third and fourth pixels are output in parallel; and so on.

The scanner is driven by parallel clocks for each section, so that during the first clock cycle, pixels 1 and 2, 129 and 130, 257 and 258, 385 and 386, 513 and 514, 641 and 642, 769 and 770, and 897 and 898 are output at the same time over 16 output lines. This increases the effective data rate, or bandwidth, to more than 240 megapixels per second, given sufficient illumination intensity. Each of these analog grayscale pixel outputs is sampled to convert the CCD current pulse output into a constant level which is proportional to the light intensity falling on the corresponding pixel.

The sixteen sampled and held parallel pixel outputs individually are compared with the threshold reference level. These latched parallel analog outputs have been trimmed individually to reduce or eliminate differences in the efficiency of the individual CCD output channels. After threshold comparison, the resulting bit-per-pixel binary information is stored until a row 120 of 1024 pixels has been built. The parallel 1024 bit data is double buffered to permit overlayed data acquisition and readout. This is useful for continuous stage 35 motion and synchronization. The 1024 bits of data are read out serially in left-to-right order relative to the scanned row. This output is analogous to the output from the photo tube 45 of FIG. 38. Readout in the light transmission embodiment is synchronized with the stage 35 motion and is clocked synchronously with the reference and guardband clocks. Because these CCD row scanners are integrating detectors over the row scan time rather than a pixel time, the system requires better stage 35 velocity uniformity than the fixed pixel illumination time of the acouto-optically scanned laser system 400 used for reflected inspection.

For situations that require serial data rates for which adequately bright light sources are not available for imaging with an integration time of one scan row 120, a time integrating imaging system can be used. In one embodiment of this technique, a conventional area CCD imager is used rather than a row scanner detector. With this approach, the stored charge is moved from row to row of the scanner, broadside (in parallel) at the same speed as the inspected image moves over the sensitive area of the scanner.

The effect of the time integrated detection is to increase the effective integration time from one-row scan-time, to the scan time for all the rows in the scanner. Typically, a one thousand fold increase in effective sensitivity can be achieved with this technique. A CCD area sensor such as the TI MC780 can be used in this manner and can take advantage of the triple output, normally provided for use with color camera applications. The area sensors either directly (for single output imagers) or after interleaving for multiple output imagers, are output in buffered serial form for comparison in the same manner as described for reflective or row scanner light transmission systems.

These same imaging techniques can be extended to other forms of database referenced inspection, such as two or three dimensional x-ray inspection. The area sensor approach combined with either a microchannel or conventional x-ray image intensifier is effective particularly as a detection system.

The serial bit stream of scan data is compared bit-by-bit with the serial reference data and the serial guardband data to detect errors, or defective areas of the actual pattern on target 103. Each bit position being compared corresponds to a single pixel on the target surface and corresponds to the same pixel in the reference data and in the guardband data. The compare is a logical operation done by Exclusively ORing (XORing) a bit from the serial scan data with the corresponding bit from the serial reference data, and then ANDing the result with the ones complement of the corresponding bit from the serial guardband data, to get the error bit. If the result (the error bit) of the logical operation is a one, then the scan bit's corresponding pixel's X-Y position is flagged as being an error location on the target 103. The error is flagged as being one of having a portion of pattern present at that pixel on target 103 when it should not be there, if the scan bit is a one. The error is flagged as being one of not having a portion of pattern present at that pixel on target 103 when it should be there, if the scan bit is a zero. If the error bit is a zero, then there is no error at the corresponding pixel position on the target 103 and there is no error in that bit's corresponding pixel on target 103. Thus, the pattern is correct at that pixel.

As error data is first detected, the corresponding starting X-Y coordinates and scan data bit are latched. The starting X-Y coordinates are the X-Y coordinates of the first pixel, on the target 103, of a sequence of pixels generating error bits equal to one. When the length, in number of pixels, i.e., number of incoming scan bits, of the error sequence has been determined to be at least as long as a predetermined minimum recordable error length, the starting X-Y coordinates, error length and starting scan bit are saved in a First-In-First-Out (FIFO) memory error buffer. The minimum error length which will be saved is a predetermined value and represents the minimum length, in number of pixels, i.e., number of incoming scan bits, of a detected inspection error in the pattern on the surface of target 103, in order for that error to be stored for operator analysis. Errors shorter in length than the predetermined minimum are ignored by the inspection system 400, and are not saved in the FIFO memory error buffer in the ECL Comparator 40. An error length counter begins once an error sequence has been detected. The counter continues to count incoming scan bits until the number of consecutive good scan bits with error bit equal to zero, also equals the number representing the minimum recordable error length. A good scan bit is one whose corresponding error bit is equal to zero.

The X-Y coordinates of the first bit in an error sequence long enough to be saved in the FIFO, are saved in the FIFO memory error buffer along with the polarity of the scan bit. The FIFO memory error buffer allows for a smooth transfer of error information to the Error Buffer module 41, seen in FIG. 38. Upon availability of the error information, the Error Buffer module performs asynchronous reads from the FIFO.

The FIFO memory error buffer is 41 bits wide and 256 locations deep. Each 41 bit location holds 10 bits of X coordinate, 20 bits of Y coordinate, 10 bits of error sequence length, and a scan bit. The scan bit denotes that a section of pattern is missing if the scan bit is zero, and denotes that the pattern has additional area if the scan bit is one.

The Error Buffer module 41 is a 4K by 48 bit FIFO which serves as an intermediate storage between the ECL Comparator 40 and bit-slice processors in the Error Consolidator module 42. The Error Buffer module 41 reads the error information from the ECL Comparator 40 and places it in the 4K by 48 bit FIFO so that the Error Consolidator 42 processors can retrieve the information as required. The Error Buffer module 41 operates asynchronously with respect to both the ECL Comparator 40 and the Error Consolidator module 42.

Error Consolidator 42

The Error Consolidator 42 includes a 24 bit bit-slice processor whose function includes the task of grouping associated sequences of errors detected in the pattern on target 103 by the ECL Comparator 40. The error data is organized into one or more consolidated error defect areas. The error data is the collection of saved data describing, or flagging, those pixels whose X-Y coordinates have been saved by the ECL Comparator as being locations of missing or additional areas of the pattern on target 103.

The Error Consolidator also eliminates classes of false errors generated by the laser beam and optical system, and by inaccuracies in converting the digital representation of the reflected light intensity into a binary, single-bit representation. Also, closely spaced sequences of defective pixels are united into single defect areas by comparing the separation of defective sequences of pixels with an error criterion allowance.

The error criterion allowance is the minimum number of adjacent pixels in the X or Y direction that must be miscompared between reference data and scan data, and not lie within a guardband, before an error is reported to DPC1 56.

As discussed above, the error criterion allowance in the X direction is applied by the ECL Comparator 40 to test a sequence of adjacent defective pixels for the requisite minimum length.

Figure 39:
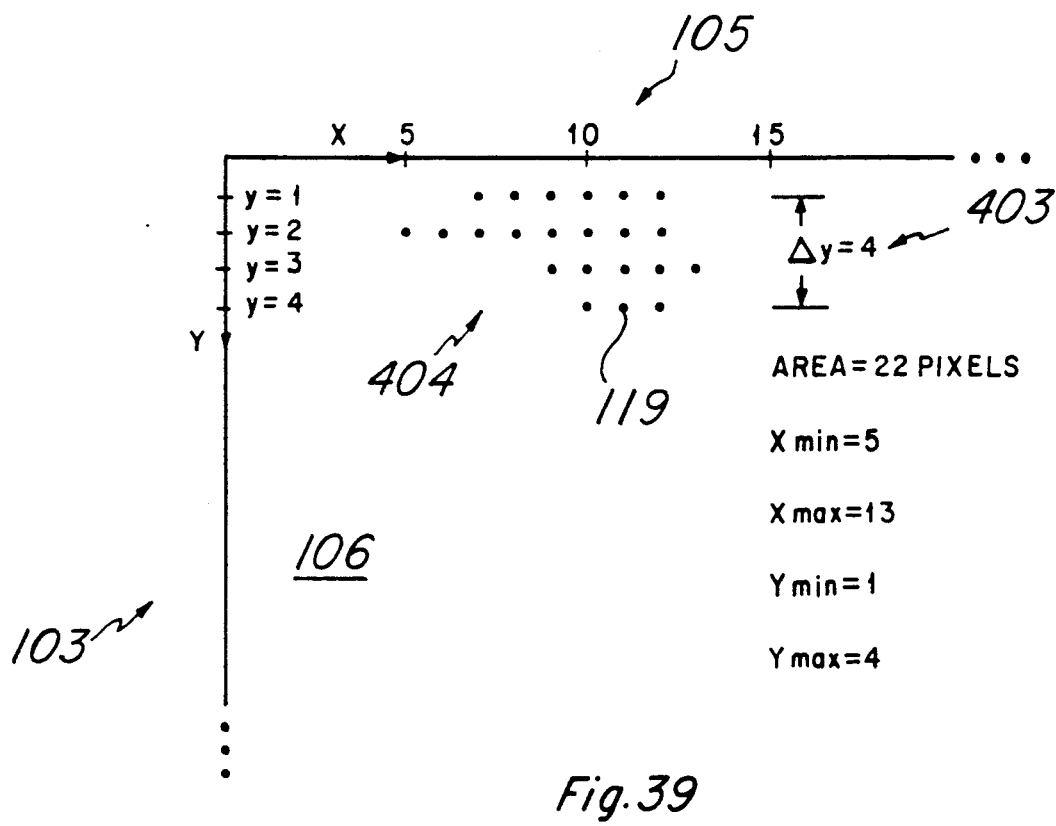
FIG. 39 is a plan view showing an example of an error in an inspected pattern in a single strip on a target.

The error criterion allowance in the Y direction can be applied, as in FIG. 39, by the Error Consolidator 42 to ensure that a predetermined minimum, the error criterion allowance, of contiguous rows of sequences of error-flagged pixels overlap in the X direction, before the sequences of error data are consolidated and reported to DPC1 56 as a single defect area.

FIG. 39 shows a section of a frame 106 on the surface of target 103. Also shown is an example of a defect area 404 comprising pixels 119 whose X-Y coordinates have been saved as sequences by the ECL Comparator 40 due to miscompares between the scan data from these pixels and the reference data. Also, these pixels do not lie within any of the guardbands around the sides of the reference data polygons. Notwithstanding the fact that the ECL Comparator 40 has saved the data describing these pixels as being in a defect area, the Error Consolidator 42 will not report these pixel locations as containing defects unless the number of adjacent rows of sequences of pixels overlapping in the X direction is greater than the predetermined error criterion allowance. Defect areas, such as at 404, having a delta Y 403 (number of overlapping rows of sequences) which is less than or equal to the error criterion allowance, are considered false errors and are not reported as defect areas to DPC1 56. In the example of FIG. 39, delta Y 403 equals 4. In order for the area 404 to be reported as a consolidated defect area to DPC1 56, the predetermined error criterion allowance must be the number three or less. Otherwise, the area 404 will be considered a false defect area, and will not be consolidated or reported.

Error data which is consolidated as a defect area and reported to DPC1 56, is described by six parameters, which are: a 10 bit X minimum, a 10 bit X maximum, a 20 bit Y minimum, a 20 bit Y maximum, a 23 bit area expressed as the number of defective pixels in the defect area, and a single scan data bit indicating whether the defect area represents added or missing parts of the pattern on target 103. X minimum is the X coordinate of the leftmost pixel in the defect area. X maximum is the X coordinate of the rightmost pixel in the defect area. Y minimum is the Y coordinate of the topmost pixel in the defect area. Y maximum is the Y coordinate of the bottom-most pixel in the defect area. These six parameters are sent to DPC1 56 for each consolidated, reportable defect area.

For the example shown if FIG. 39, X minimum=5, X maximum=13, Y minimum=1, Y maximum=4, and the area=22 pixels. The scan data bit is not indicated as to whether it is a one or a zero.

The error criterion allowance can also be applied to consolidate into a single defect area, non-contiguous sequences of defective pixels closely spaced in the X or Y direction.

Figure 40:
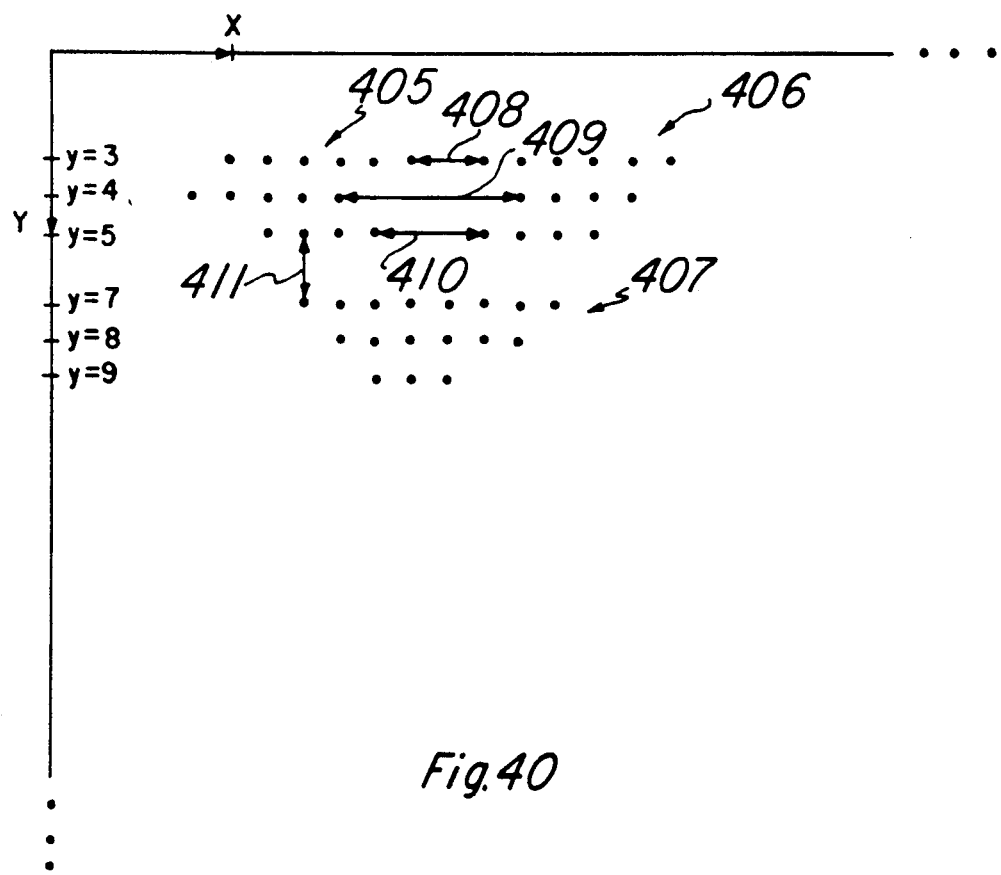
FIG. 40 is a plan view showing a second example of an error in an inspected pattern in a single strip on a target.

For example, in FIG. 40, the leftmost defect area 405 and the rightmost defect area 406 consolidate into a single defect area provided that at least one of the sequence separation distances, 408, 409 or 410 is less than or equal to the error criterion allowance. Furthermore, defect area 405 and defect area 406 must each have a sufficient number of overlapping adjacent rows of error sequences to be consolidatable as a defect area. That is, the number of overlapping rows of error sequences must be greater than the error criterion allowance.

Similarly, the bottom-most defect area 407 consolidates with defect areas 405 and 406 if areas 405–407 are separately consolidatable as defect areas, and if the defect separation 411, measured by the number of intervening rows, is less than or equal to the error criterion allowance. The bottom-most defect area 407 must also have its error sequence in row Y=7 overlap in the X direction with the two error sequences in row Y=5.

DPC1 56

DPC1 56 includes a bit-slice processor to do fast sorting of the data describing the defect areas consolidated by the Error Consolidator 42. The defect areas are sorted by the area in pixels, in descending order and formed into a list which is sent to host memory 4 for use by the host computer 3.

Modules 30–36 are the same as described in conjunction with FIG. 6.

Operator Review of Defect Areas

The list of sorted errors sent to the host computer 3 by DPC1 56 is presented on the video display terminal 2 for review by the human operator. The list of errors, that is, defect areas, is presented in order of the most serious, i.e., those with the largest area first. The operator selects which defect area he desires to view on color display 29. The stage 35 then moves the selected target defect area into the correct X-Y position to be laser scanned in real-time during the operator review process, to generate a gray scale image of the defect area. Positioning of the stage 35, and thus the target 103, is computed from location information that is a portion of the defect data collected by the error consolidator 42. The stage is moved to a backoff location so that it is moving at a constant speed when the defect area to be reviewed is under the raster scanning laser beam.

At this point, the target 103 area, which includes the defect to be displayed, is raster scanned by the laser beam, and a gray scale image of the scanned area is displayed with the defect area centered upon the screen of the color display 29. The ECL comparator 40 has a six bit analog-to-digital converter which transforms the analog representation of the reflected light intensity for a single pixel into a six bit digital gray scale representation. Thus, rather than thresholding each pixel to a one or a zero, as is done during the inspection process, a six bit range of intensity is stored, and then displayed. One of the embodiments of the invention does, however, contemplate that the gray scale image be selectively thresholdable, either between one and zero as during inspection, or by dividing the 64 possible values for the six bit combination into a lesser number of values. Each pixel to be displayed maps onto one and only one display 29 pixel. Each display 29 pixel individually varies in brightness according to the six bit gray scale, or thresholded, output from the ECL comparator 40.

During the inspection process, when defect areas, if any, are located, only the area in number of pixels, the X-Y extremes and the type of defect are saved for each consolidated defect area. Scan data bit-maps of the defect areas are not saved. This means that the large amounts of memory which would be necessary to store bit-mapped images of all the defect areas discovered during an inspection process, are not required. Also, real-time generation on the fly of a scan data image of a defect area is quicker and easier than would be the case if a large, bit-map, scan data base had to be accessed and managed.

Overlaying the gray scale image of the scanned area, is a computer generated reference image of the same area. The computer generated reference image is generated from the reference data stored on data disk 13 on a real-time basis during operator review. The frames to be displayed are read from data disk 13 by DPC3 14. The location of a desired frame is found by using a frame look-up table created by DPC2 when the database was read from data disk 13 during the inspection process. This table is a directory for finding the beginning of the frame to be read. The data contained in the frame is read by DPC3 and sent down the pipeline that goes to the window clipper 19. This is repeated for each frame needed to create the overlayed reference image. Usually four frames are required. If the de-zoom (discussed below) process is not used, from one to four frames of data are possible to view at a time on color display 29. Where de-zoom scale of two or greater is used, then more than four frames can be viewed on color display 29.

The reference image is created frame-by-frame, on the fly, during operator review of the defect area. The data for the displayed frames is read from data disk 13 and changed by DPC3 to the previously discussed move/draw turnpoint polygon representation of the portion of the pattern in the displayed frames. The data is then sent to window clipper 19 where only the portion of the data to be displayed by color display 29 is sent on to preprocessor1 20A. All frames to be displayed are sent down the same pipeline to the window clipper 19. Thus, the review process represents a departure from the writing or inspection processes where consecutive frames of data are sent down alternate or different pipelines. Also, during the review process only a limited number of frames of data will be read from data disk 13 and subsequently sent down the pipeline. During the review process, guardbands are not generated or used, so the database processing is done in a similar manner to the processing of the data during the pattern writing process, with the previously noted exception of sending all the frames to be displayed down the same pipeline.

Preprocessor1 20A creates a vector representation of the frame reference image data sent by window clipper 19. Preprocessor1 20A then sends the vector representation of the image data to pixel memory module1 24A, where it is transformed into a representation addressing the pixels on and between left and right vectors. Pixel memory module1 24A then transforms the image data into a 64 bit word bit-map of the reference data to be displayed on color display 29.

These reference data transformations are performed on the fly, that is, only the reference data for the defect area being reviewed is read from data disk 13 and sent down the window clipper pipeline and subsequently is processed and sent to the display 29 on a real-time basis during the operator review of the defect area. Only the area in pixels, the X-Y extremes and the type of defect are saved for each consolidated defect area in the scan data. A reference data bit-map of the defect area is not saved. This means that the large amounts of memory which would be necessary to store bit-mapped reference data images for all the defect areas discovered during an inspection process, are not required. Also, the compacted reference data base on data disk 13 is easier and quicker to access than would be the much larger expanded reference data bit-map of all the defect areas. Requiring even more memory would be a reference data bit-map of the entire target surface as produced from the reference database at some point prior to the operator review process.

The overlay produces a yellow color in those areas where the gray scale image of the actual pattern and the computer generated reference image overlap. Thus, the yellow area of the image on the color display 29 represents that portion of the actual pattern on target 103 which contains no defects.

The overlay produces a green color in those areas on the target 103 where there is pattern present that should not be there.

The overlay produces a red color in those areas on the target 103 where pattern is absent that should be there.

The color display 29 displays a portion of the target 103 that is 512 pixels 119 by 512 pixels 119. A frame 106 is 1024 pixels 119 by 512 pixels 119 (FIG. 3), so, at most, only half a frame at a time can be displayed on color display 29. Real patterns on a target's surface can cross frame 106 boundaries. However, a reference data representation of the same pattern uses contiguous, constituent polygons to represent the pattern. The constituent reference data polygons do not cross frame boundaries but instead, abut against one another at the frame boundaries if the pattern crosses the boundaries. The color display may include areas from as many as four frames. For instance, the contiguous corner areas of four frames will be displayed if a strip boundary runs vertically down the middle of the display, and if the horizontal boundaries between the two sets of contiguous frames on either side of the strip boundary, run horizontally through the middle of the display 29. The window clipper 19 deletes the reference polygons from the portions of the frames which will not be shown on display 29.

The gray scale image of the pattern on target 103 and the reference data image of the ideal pattern, can both be de-zoomed. That is, a larger area of the target and of the reference data can be shown on color display 29, with a corresponding shrinkage in the display size of the target and reference data pattern features. De-zoom scales are 1, 2, 4 and 8.

With de-zoom scale 1, display 29 shows each pixel 119 that is within the viewing area on target 103, and shows each pixel of the reference data that corresponds to the viewing area. That is, there is a one-to-one correspondence between the pixels of the target viewing area and the pixels of the display 29. Likewise, there is a one-to-one correspondence between the pixels of the reference data viewing area and the pixels of the display 29.

With de-zoom scale 2, display 29 shows every other pixel of the target in the X direction, so that the viewing area is now twice as wide as for de-zoom scale 1. Likewise, display 29 shows every other pixel of the target in the Y direction, so that the viewing area is now twice as high as for de-zoom scale 1. Therefore, the new viewing area is four times as large as for de-zoom scale 1. Similarly, the viewing area for de-zoom scales 4 and 8 are 16 times and 64 times, respectively, as large as for de-zoom scale 1.

Gray scale module 38 receives a 6 bit gray scale word for each pixel in the target viewing area from the analog-to-digital converter in the ECL comparator 40. When de-zoom scale 1 is in effect, each pixel word received by the gray scale module 38 is sent to the color display 29. When de-zoom scale 2 is in effect, every other pixel word received from ECL comparator 40 for the first row of the viewing area is sent to color display 29. None of the pixel words received for the second row of the viewing area are sent to the display 29. For the third row of the viewing area, again every other pixel word received is sent to display 29, and so on. i.e., every other pixel word from every other viewing area row of pixel words received from ECL comparator 40 are sent to color display 29. For de-zoom scale 4, every fourth pixel word from every fourth viewing area row of pixel words received from ECL comparator 40 are sent to color display 29. Likewise, for de-zoom scale 8, every eighth pixel word from every eighth viewing area row of pixel words received from ECL comparator 40 are sent to color display 29.

Window clipper 19 performs the same de-zoom scaling functions on the reference data in the same way as gray scale module 38 performs de-zoom scaling on the scan data input from ECL comparator module 40.

Autoalignment of the Target

Autoalignment provides three functions for an inspection system 400, or for a writer system 50 that also has inspection capability: 1. determines the exact location of the target 103; 2. adjusts the rotational alignment of a stage 35 and target 103 about the theta axis so that the Y direction stage motion follows a strip 105; and 3. determines if the target 103 has thermally expanded or contracted. Autoalignment is achieved by providing fiducial marks in predetermined locations on the surface of target 103, and using the inspect capability to locate these fiducials after the target has been placed on the stage 35.

Figure 45:
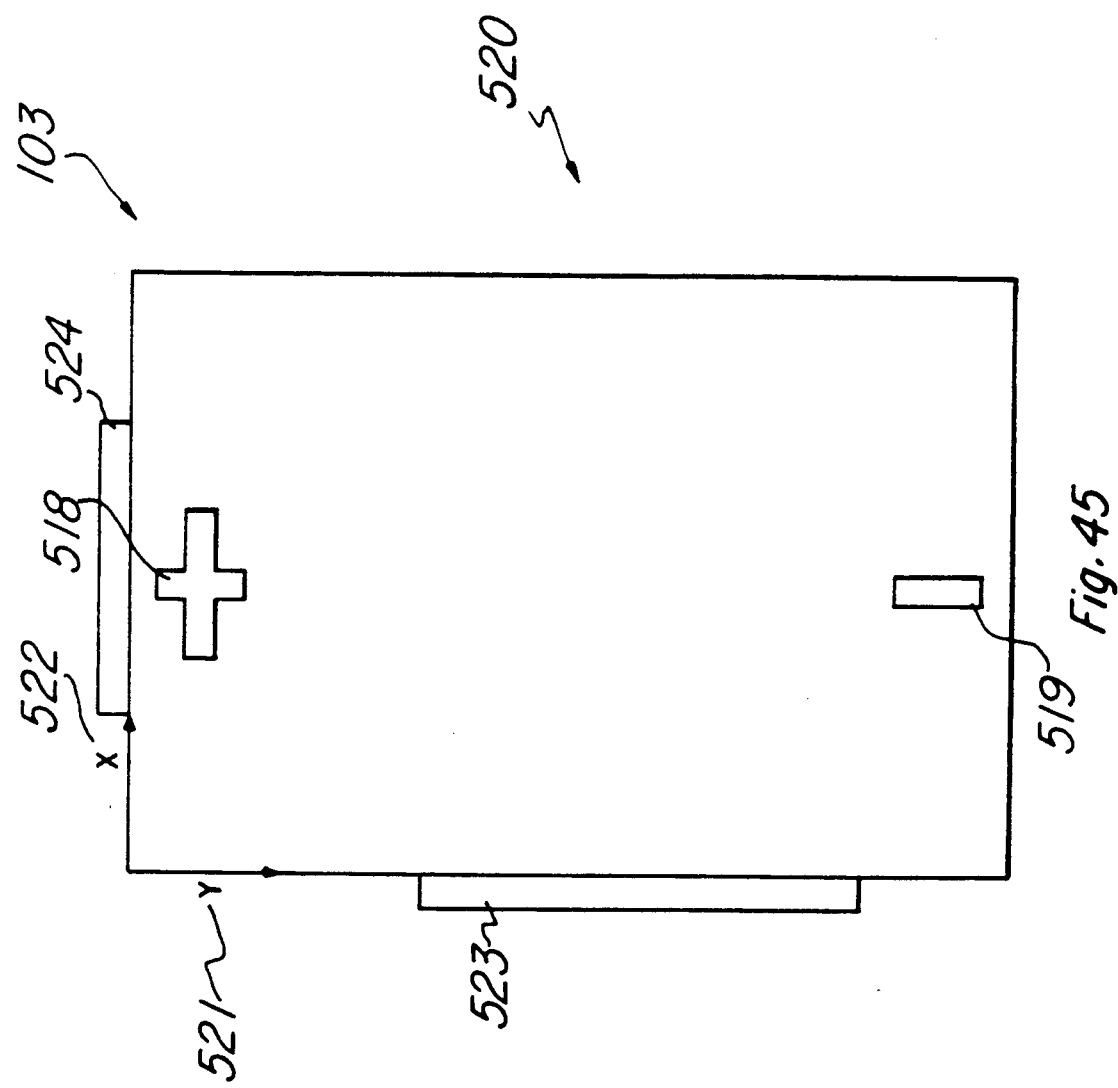
FIG. 45 is a plan view of a reticle target on a stage, showing top and bottom fiducial marks.

FIG. 45 shows a target 103 which is a reticle 520 having a top fiducial mark 518 and a bottom fiducial mark 519, each in the center of the reticle with respect to X. The top fiducial mark 518 is shown as a cross and the bottom fiducial mark 519 as a bar, although, any predetermined identifiable shapes will work. Top 518 and bottom 519 fiducial marks are shown larger with respect to reticle 520 than would actually be the case. Normally, each fiducial mark is small enough to fit within a single frame 1024 pixels wide by 512 pixels high. Preferably, top 518 and bottom 519 fiducial marks have centroids with the same X coordinates in the same center strip 105, so that the reticle 520 will be aligned when a line between the centroids of the top and bottom fiducial marks is parallel to the Y axis. It will be understood, however, that the invention may be practiced with a target having two or more fiducials, at predetermined orientations, that do not have centroids with the same X coordinates or lie in the same strip, or lie in the center strip. Preferably, each fiducial mark is sized so that it can fit completely within a single frame 106.

The alignment process begins by placing manually a target 103 on a stage 35. Preferably the stage 35 has an X stop 523 and a Y stop 524 against which the target may be placed to achieve preliminary X-Y-Theta alignment of the target, where the Theta axis is perpendicular to the X-Y plane. Preliminary alignment means that the X-Y position of the centroid of each of the top 518 and bottom 519 fiducial marks is known within three adjacent strips 105 and five adjacent frames 106.

The top fiducial mark 518 is located by the pattern inspector 400 in the inspection mode, by raster scanning the middle three strips of the target 103, for a Y distance of five frames 106 for each strip 105. During the normal inspection mode, a target 103 is raster scanned in strips which extend for the full, or nearly the full, length of the target. In the autoalignment mode, preferably, each strip is only five frames long. Also, during the normal inspection mode, a target is raster scanned in strips which cover, or nearly cover, the entire width of target 103. In the autoalignment mode, preferably, only the three center strips 105 are raster scanned. Thus, preferably, only the upper five frames of each of the center three strips are raster scanned in the reticle of FIG. 45.

Similarly, the bottom fiducial mark 519 is located by the pattern inspector 400 in the inspection mode, by raster scanning the bottom five frames 106 of each of the the center three strips 105 of reticle 520.

Thus, for both top 518 and bottom 519 fiducial marks, only fifteen frames 106 are scanned for each mark. This saves a great amount of time over scanning the entire target 103, although, that certainly could be done.

The data flow for inspection to find the fiducial marks proceeds as previously described for inspection of the entire target 103, up through the error consolidator 42. However, the reference database does not describe an idealized fiducial mark pattern, but describes the areas of the target where the fiducials are expected, as being clear areas devoid of any pattern. Thus, when the reference data is compared with the scan data, the fiducial marks register as errors. The error consolidator 42 outputs the consolidated error description of the top fiducial mark 518 as before, i.e., the area in pixels, X maximum, X minimum, Y maximum, Y minimum and the type of error. The error consolidator treats the bottom fiducial mark 519 and any other pattern in the scanned areas, in the same manner as for the top fiducial mark 518. As before, DPC1 56 sorts the errors in descending order of pixel area, creates a list of the errors, and sends the list to host computer 3.

Host computer 3 compares each of the errors with the following test:
IF AREA < = MAX_FIDUCIAL_AREA AND
IF AREA > = MIN_FIDUCIAL_AREA AND
IF (X maximum-X minimum) < = FIDUCIAL_WIDTH + (2*TOLERANCE) AND
IF (X maximum-X minimum) > = FIDUCIAL_WIDTH − (2*TOLERANCE) AND
IF (Y maximum-Y minimum) < = FIDUCIAL_HEIGHT + (2*TOLERANCE) AND
IF (Y maximum-Y minimum) > = FIDUCIAL_HEIGHT − (2*TOLERANCE)
THEN a fiducial mark has been found and corresponds to the data tested. The parameters MAX_FIDUCIAL_AREA and MIN_FIDUCIAL_AREA are the maximum and minimum fiducial areas, respectively, and they describe the acceptable limits within which a fiducial mark must fall. Parameters FIDUCIAL_WIDTH and FIDUCIAL_HEIGHT are the nominal width and nominal height, respectively, of an ideal fiducial mark. 2* TOLERANCE is a parameter setting the acceptable deviations from the ideal width and height for a valid fiducial mark. The parameters are unique for each fiducial mark. Preferably, Top 518 and bottom 519 fiducial marks have different shapes and the parameters for the two will not be the same, although the parameter TOLERANCE preferably is the same for both. The above test is performed on each of the errors, first with the parameters for the top 518 fiducial and then with the parameters for the bottom 519 fiducial.

If the two fiducial marks are within the scanned areas of the target, and if they fall within the parameters defining acceptable fiducial marks, then the host computer will identify which of the fiducial marks is the top fiducial mark 518 and which is the bottom fiducial mark 519.

If the top 518 and bottom 519 fiducial marks have been located successfully, then their centroids will be determined by the host computer 3. Since the shapes chosen for the fiducial marks are symmetrical about their centroids, the X-Y coordinates of the centroids are determined by host computer 3 by setting X equal to X minimum+((X maximum-X minimum)/2), and setting Y equal to Y minimum+((Y maximum-Y minimum)/2).

If the top 518 and bottom 519 fiducial marks have the same X coordinates, then the target is aligned already. If the X coordinate of the top fiducial mark 518 is less than the X coordinate of the bottom fiducial mark 519, then the stage 35 has to be rotated clockwise to align the target 103. If the X coordinate of the top fiducial mark 518 is greater than the X coordinate of the bottom fiducial mark 519, then the stage 35 has to be rotated counter-clockwise to align the target 103. The stage will be rotated about the center of the target by an amount equal to one-half the absolute value of the difference between the X values of the top 518 and bottom 519 fiducial marks, as measured at the top or bottom fiducial Preferably, the centroids of the fiducials are equidistant from the center of the target 103, and are centered in the X direction on the target 103.

The inspection process then can be carried out again on the fiducial marks to see if the centroids are within half a pixel of each other in the X direction. If they are not, then again the stage can be rotated. This process can be carried out as many times as are necessary to achieve the desired accuracy of alignment.

The distance MD between the centroid of the top fiducial mark 518 and the centroid of the bottom fiducial mark 519 is computed by host computer 3 by finding the absolute value of the difference between the Y coordinates of the two centroids. The measured distance MD is compared against a predetermined value PD for the distance. There is a predetermined value PV of the distance between two successive Y addresses, that corresponds to the predetermined value PD of the distance between the two centroids. The actual distance AV between two successive Y addresses that corresponds to the measured distance MD between the two centroids, can be found by solving for AV in the following relationship: $(PD/MD)=(PV/AV)$. The actual distance AV is the spacing to be used between two adjacent rows 120 for the then existing environmental conditions for the target 103. These environmental conditions include the ambient temperature for the target, which influences the value for the measured distance MD.

Semiconductor Wafer Bar-by-Bar Alignment

Figure 46:
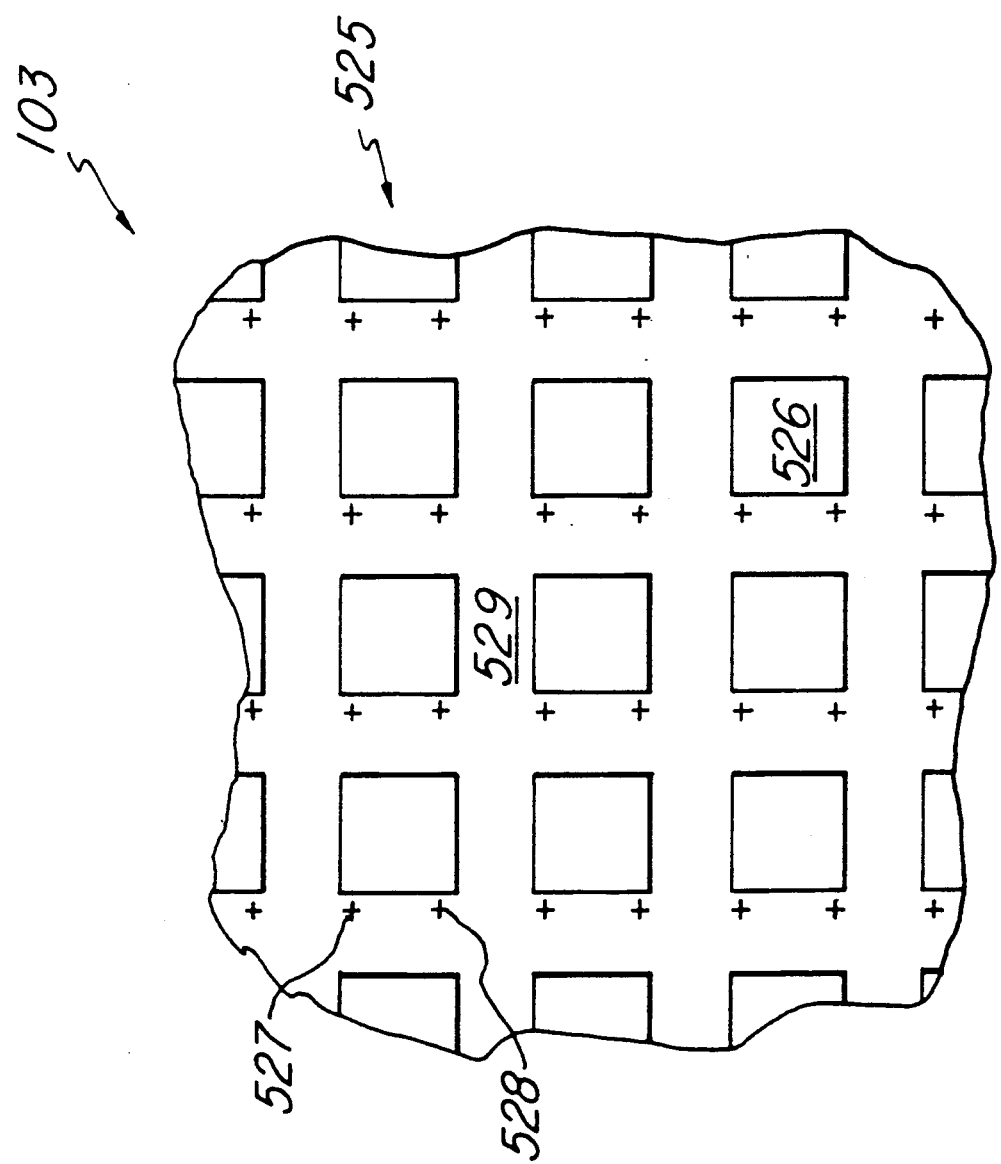
FIG. 46 is a plane view of a section of a semiconductor wafer, including the individual IC bars.

The invention comprehends direct laser writing and inspection of integrated circuit patterns on the individual chips 526, i.e., IC bars 526, of a semiconductor wafer 525, as seen in FIG. 46. The wafer writing process is carried out by laser exposure of photosensitive photoresist on the face of the wafer. The inspection process is carried out on patterns of etched photoresist or etched metal on the semiconductor wafer.

Typically, each semiconductor wafer 525 is comprised of a plurality of rectangular IC bars 526, usually arranged in a rectangular matrix format. The IC bars will be defined by a grid of scribe alleys 529. A single IC bar 526 is defined by the area of semiconductor material between two adjacent, parallel, horizontal scribe alleys and between two adjacent, parallel, vertical scribe alleys.

If only a single patterned layer is required for each IC bar, requiring only a single raster scanning of the areas of the IC bars, then wafer-level alignment marks may be sufficient to determine the X positions marking the beginning of the rows 120 of the various IC bars. Wafer level alignment marks are marks uniquely identifiable by the pattern inspector 400 when in the inspect mode, as described previously in connection with autoalignment. The alignment marks need only be two in number to establish X and theta offsets of the orientation of the wafer, with respect to the orientation required to produce scanned strips 105 that are parallel with the vertical scribe alleys.

For more demanding applications, where previous layers have been patterned using bar-level alignment of optical wafer steppers, bar-by-bar alignment is required in addition to the wafer-level alignment discussed previously under autoalignment. Bar-by-bar alignment is not required in those instances where the first or only patterning layer is patterned by the laser pattern inspection system 400 while in the writer mode.

FIG. 46 shows a section of a target 103 which is a semiconductor wafer 525, having a plurality of IC bars 526 on which integrated circuits may be fabricated. The IC bars are separated by a rectangular gridwork of intersecting rows and columns of scribe alleys 529. Scribe alleys are the areas which will be cut away or otherwise destroyed during the process of separating the individual IC bars 526 after the integrated circuits have been fabricated on the IC bars. Each IC bar 526 has associated with it an upper bar-alignment-mark 527 and a lower bar-alignment-mark 528, which were patterned photolithographically in the vertical scribe alley 529 to the left of the IC bar. The bar-alignment-marks were patterned at the same time that the first circuit layer was patterned on the IC bars 526. The bar alignment marks are illustrated as crosses, however, any recognizable pattern would work. Two alignment marks per bar have been shown, but more than two can be used.

Each pair of upper 527 and lower 528 bar-alignment-marks is associated with the IC bar immediately to its right and is at a predetermined orientation and distance from the pair. Each pair of bar-alignment-marks defines the rotational and translational offsets of the X-Y coordinate system for the previous layer or layers of patterning for that IC bar 526, with respect to the wafer-level orientation.

The inspection system 400 identifies and locates the bar-alignment-marks by raster scanning only the vertical scribe alleys 529. The vertical scribe alleys are scanned in strips 105 extending the full length of the scribe alleys. By scanning only the scribe alleys, time is saved over scanning the entire wafer 525. The scan data from the bar-alignment-marks can be compared to a reference data representation of the bar-alignment-marks, or, as in the case of autoalignment, described previously, the list of data corresponding to the bar-alignment-marks is sent to host computer 3 where the offsets are determined and an IC bar location map is constructed. Each scribe alley requires only a low number of scanned strips to identify and locate all the bar-alignment-marks, further reducing the total wafer scan time. A stepping map created by the optical stepper while patterning the first layer, combined with the individual bar header information or stepping design information can be used to provide the locations for each of the bar level bar-alignment-marks. Instead of the bar-alignment-marks, isolated, prominent features of the first layer of pattern, providing recognizable orientation information can be used.

Either the wafer 525 must be rotated and/or translated, or the laser pattern inspection system 400, while in the writer mode, must compensate for the X-Y translation by timing the beginning of modulation of the scanning laser beam and/or by rotating the data from the pipelines. The preferred embodiment of the invention contemplates using the latter method. Likewise, during inspection of the wafer 525, the top 527 and bottom 528 bar-alignment-marks are used to determine the individual orientations of the IC bars 526 so that data from the phototube 45 will be clocked into ECL comparator 40 at the correct timing offsets so that the scan data will correspond to the correct pixel reference data positions.

Since most of the IC bar 526 pattern offsets from the wafer-level orientation are translational and not rotational, it should be sufficient in the majority of instances to compensate for the offsets solely by timing when to begin raster scanning each row. That is, the X-Y position of the start of each row is determined in light of the Y stage motion and X sweep direction by timing when to begin a sweep and timing at what point in the sweep that modulated data should begin to be output.

The wafer 525 is written or inspected by scanning the wafer in strips extending nearly the full height of the wafer, rather than by scanning each IC bar, one-at-time, in strips extending only for the height of the IC bar 526. This saves turnaround time at the end of each strip by a division factor equal to the number of IC bars 526 on the wafer 525. Each strip has a height sufficient so that the aggregate of the strips cover all the areas on the wafer which require patterning.

Since each wafer 525 is raster scanned in strips extending for the height of the wafer, strip memory buffers can be used at the outputs of the pixel memory modules 24A-24D to store a strip's worth of translated and possibly also rotated data to be written or used as reference data during the inspection process.

AUTOFOCUS FOR WRITER AND INSPECTION SYSTEM

The autofocus system allows for very fast laser writers 50 and inspectors 400 to be able to move across non-flat targets 103 at high speed and still keep the objective lens 117 in focus. A small, preferably solid-state, laser is used to direct a focused spot coinciding with the spot focus of the objective lens on the surface of target 103. That is, both the writing or inspection laser 100 and the autofocus laser direct laser beams to the same pixels location on target 103. The autofocus spot is picked up as a reflection separate from any reflections from the scanning laser beam, and relayed to a linear photodetector which determines the target 103 surface to lens height by the lateral distance apparent to the detector. This information is fed to a spiral or ring and magnet system to keep the planametric distance constant.

For one embodiment of the laser writer system 50, an objective lens 117 having a fixed reduction of 7.145 and working over a distance of 23 inches was required. The depth of focus of this lens was less than one mil, but target 103 surface variations can cause the objective-lens-117-to-target-surface distance to vary as much as several mils. The autofocus system corrects for this distance variation. The high speeds of stage 35 require that the autofocus system be able to compensate for focusing variations up to the rate of 100 hz. An electro-mechanical system moves just the lower portion of the multi-element objective lens 117, with external paralactic sensing of the focal error. The focusing variations required to follow the surface contour of the target 103 do not change the reduction ratio of the objective lens 117.

Figure 44:
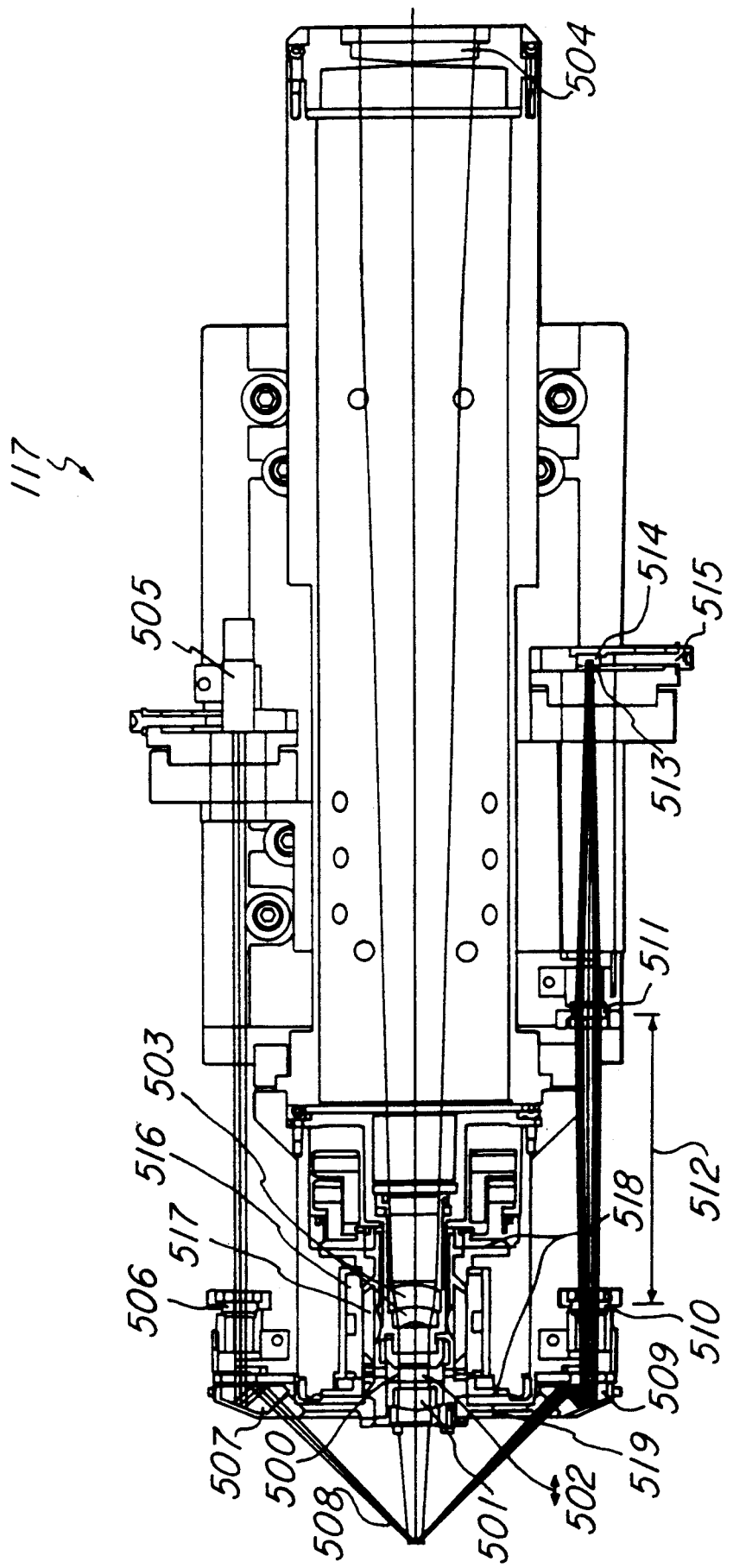
FIG. 44 is a side sectional view of the objective lens and autofocus mechanism for the pattern inspector system.

Referring to FIG. 44, it can be seen that the objective lens system 117 includes an infinity corrected high resolution objective lens 501 movable along the optical axis to follow the surface contour of the target 103 to maintain focus of the laser 100 on the surface of target 103. The objective lens 501 movement along the optical axis takes place in a region 502 in which the laser beam is collimated, as indicated by parallel light rays 500.

The intermediate, non-moving long focus lens system 503 sets the magnification and track length. The upper field lens 504 gives the laser deflection system telecentricity. The laser deflection system includes the chirp deflector 102.

A 2 mw, 820 nm, 5 mm diameter collimated beam, gallium arsenide, infra-red laser 505 is used to provide the autofocus spot laser light for tracking the objective-lens-117-to-target-surface distance. The 100 mm lens 506 is used to focus the collimated light from laser 505 and to set the focal point of laser 505 at the desired writing or inspection distance. This distance is the objective-lens-117-to-target-surface distance. Prism 507 directs the laser beam from autofocus laser 505 to strike the target 103 surface coincidentally with the same spot struck by writer/inspector laser 100 beam. The prism 507 directed laser beam 508 has an angle of incidence with respect to the target 103 surface, of 45 degrees, and is specularly reflected from the target surface at a reflected angle of 45 degrees into a second prism 509. THe second prism 509 directs the reflected autofocus laser beam through a series of two lenses and into a photodetector 514. The directed, reflected laser beam directed by the second prism 509, is parallel to the optical axis of the objective lens 117 only if the objective-lens-117-to-target-surface distance is correct.

The first of the series of two lenses is the 100 mm collimation lens 510, which re-establishes collimation of the reflected autofocus laser beam. The recollimated beam which emerges from the collimation lens 510, is exactly parallel with the optical axis of the objective lens 117 only if the objective-lens-117-to-target-surface distance is the desired distance. If the distance is too large, then the recollimated beam is deflected to the right, as seen in FIG. 44. If the distance is too small, then the recollimated beam is deflected to the left, as seen in FIG. 44.

The second of the series of two lenses is the telescope objective lens 511, which focuses the recollimated beam into a small spot on the silicon photodetector 514. The distance 512 between the collimation lens 510 and the telescope objective lens 511 is chosen to be approximately equal to the focal length of the collimation lens 510. This makes all reflected beams pass centrally through the telescope objective lens 511, notwithstanding any aperture shearing at the collimation lens 510 due to main focal error.

In order to prevent stray or diffusely reflected laser light from the writing/inspection laser 100 from reaching the photodetector and interfering with its operation, an optical filter 513 is placed in front of silicon photodetector 514. Some embodiments of the invention utilize a writer/inspector laser 100 which emits blue-green light at a 488 nm wavelength. In that embodiment, the optical filter 513 will preferably be a red filter for filtering out light at a wavelength of 488 nm.

The silicon photodetector 514 is a split "Double-D" design, differentially connected to a servo-amplifier system for moving axially the high resolution objective lens 501 to keep the writing/inspection laser beam focused on the surface of the target 103. Any objective-lens-117-to-target-surface distance errors are translated into horizontal laser 505 spot motions across the photosensitive face of the silicon photodetector 514. The spot motions across the "crack", or split diode, in the face of the photodetector 514, give a plus or minus output from the photodetector 514, that is approximately linear over a spot movement range large enough to cover any normal variations in the contour of the target 103. A screw 515 is for adjusting the horizontal position of the mechanical stage upon which the photodetector 514 is mounted. With the screw 515, the horizontal position of the photodetector can be adjusted to make zero electrical output from the photodetector correspond exactly to the desired writing/inspection focus. That is, the desired objective-lens-117-to-target-surface distance exactly corresponds to zero electrical output from the photodetector.

The objective-lens-117-to-target surface distance error discovery system is based on parallax. The autofocus system responds primarily to the vertical position of the target 103 surface, and is not responsive to small angular variations of the contour of the tested spot on the target surface. The autofocus system is configured to be tolerant of minor optical imperfections in its component parts.

A two-section differentially connected coil 516 of 520 turns of number 26 wire, and having a total electrical resistance of 12.5 ohms, is fed electrical currents of up to plus or minus 0.7 amps by the servo amplifier (not shown). A one inch long 60 gram cylindrical magnet 517 of moment 2500 cgs units, responds to the coil current to produce the required axial motions of the moving assembly. The moving assembly includes the high resolution objective lens 501, the cylindrical magnet 517, the prisms 507 and 509, the 100 mm focusing lens 506, and the collimator lens 510. This moving assembly is supported by 0.008 inch thick beryllium-copper spiral-cantilever springs 518. The moving assembly weighs 280 grams and resonates at 28 hz with the spiral cantilever springs. Besides this primary resonance, there are several secondary resonances, of which the most important is a very high-Q resonance at 900 hz. Motions with amplitudes up to plus and minus 0.010 inches are possible.

Pattern Inspector Data Flow

Figure 53A:
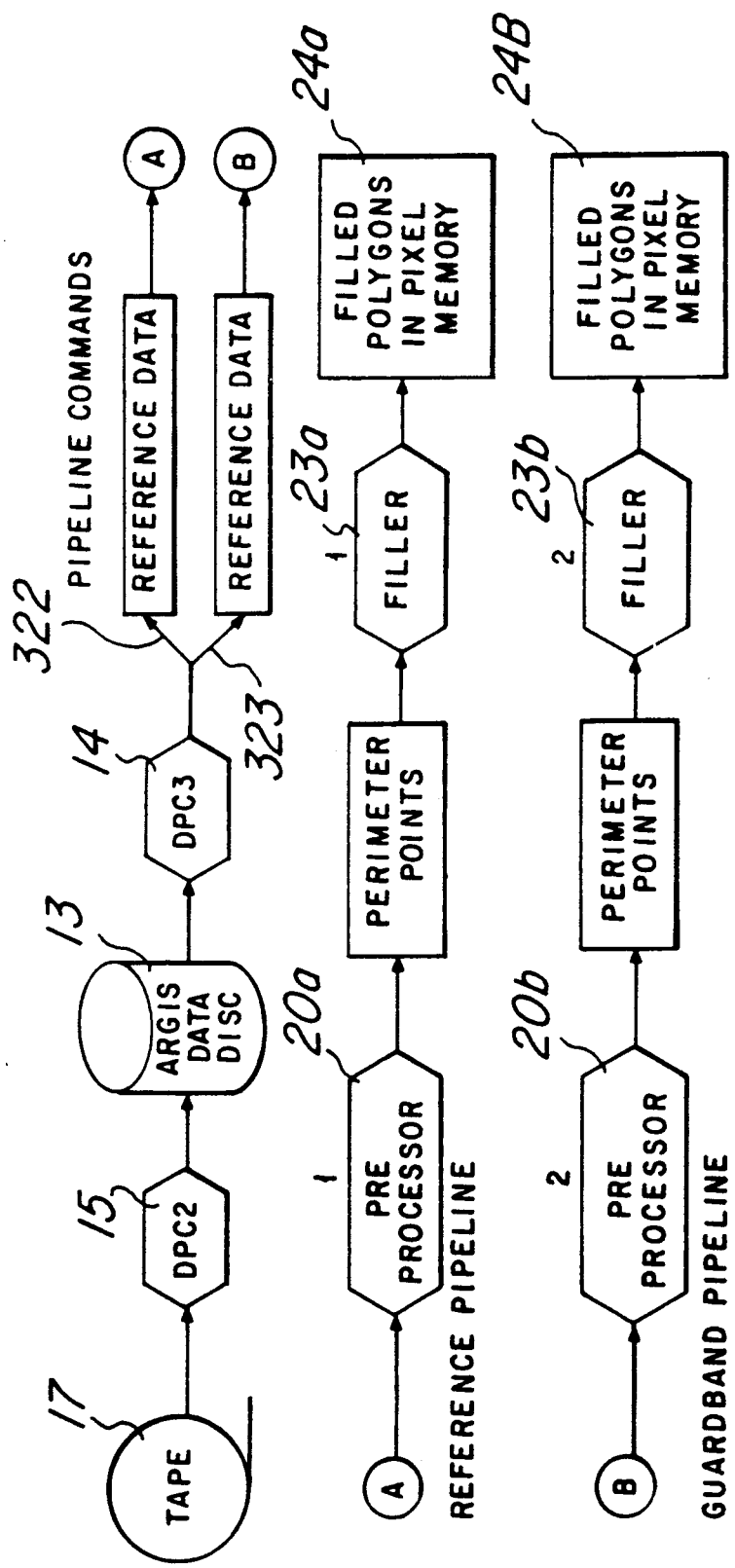
FIGS. 53A and 53B are data flow diagrams for the pattern inspection system.
Figure 53B:
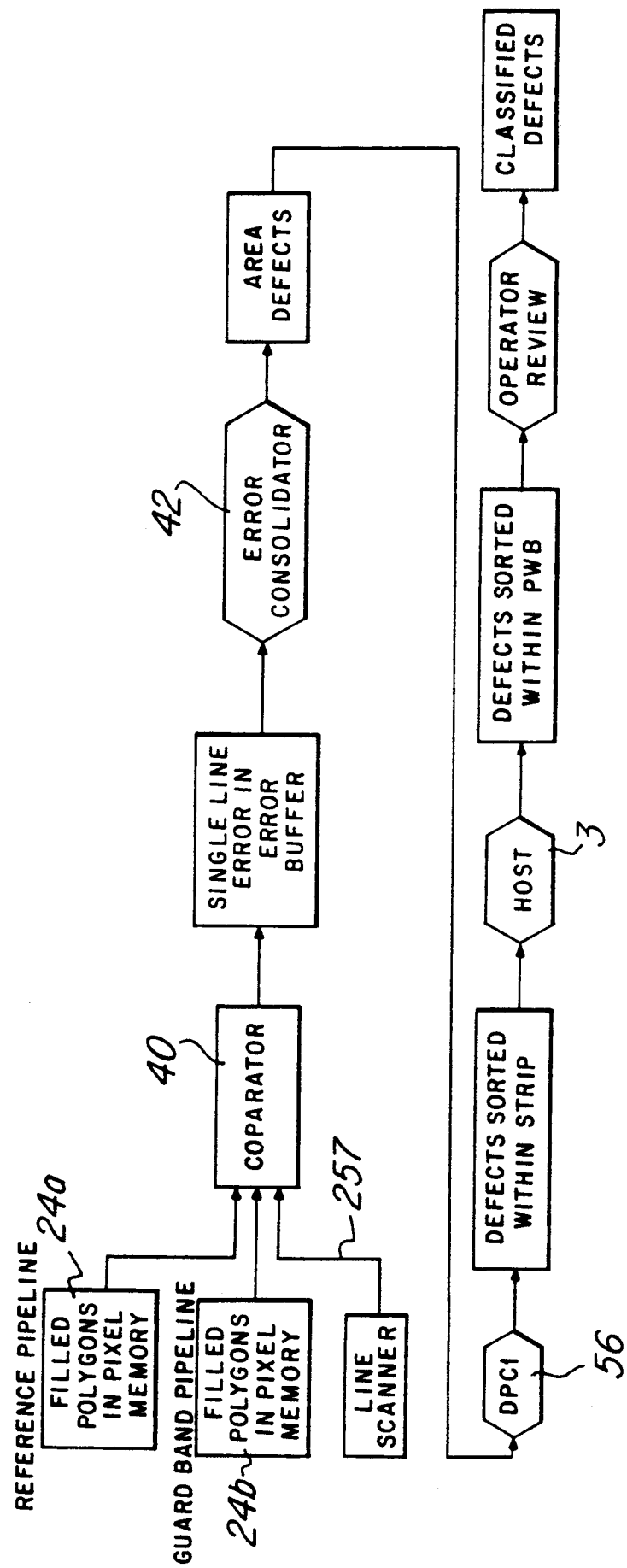

The data flow for the pattern inspection system 400 is illustrated in FIGS. 53A and 53B, and is very similar to the data flow for the pattern writer system 50, as discussed previously in connection with FIG. 9. FIGS. 53A and 53B differ from FIG. 38 in that FIGS. 53A, 53B only show two pipelines 322 and 323, whereas FIG. 38 shows an inspection system 400 having four pipelines. As has been indicated previously, the invention comprehends the use of two or more pipelines to accomplish parallel processing of the database to a bit-map final form. FIGS. 53A, 53B shows only two pipelines merely to simplify the diagram.

The tape 17 resident database representation of a pattern is the same for the inspection system 400 as for the writer system 50. Thus, for the example rectangle 300 pattern shown in FIG. 26, the database 313 shown in FIG. 27 is also the database for rectangle 300 during an inspection process carried out as shown in FIGS. 53A, 53B.

As with the writer system 50, DPC2 reads the database from tape 17, reformats it into a turnpoint polygon representation, and stores that representation on data disk 13. What is different from the writer system 50, however, is that with the inspection system 400, DPC2 also adds guardband polygon descriptions to the database. These guardband polygons are also described in turnpoint polygon representation. For purposes of simplicity, only the reference data and guardband polygon data for frame 301 is shown, since the data for frame 302 is constructed in just the same way.

The reference data for frame 301 is identical to the reference data shown in FIG. 29 for the writer system 50.

In FIG. 48A, the data indicated at 254 is the turnpoint description of guardband 249 shown in FIG. 47. Likewise, the data indicated at 255 is the turnpoint description of guardband 250, and the data indicated at 256 is the turnpoint description of guardband 248. As can be seen, reference polygons and guardband polygons are each described separately.

FIGS. 49A and 49B illustrate the guardband data only which is sent down pipelineB at 323. The reference polygon data processing in the pipelines will not be shown since it is just the same as was illustrated and discussed with reference to FIG. 9 and writer system 50. The 25 bit words for the guardband polygons are constructed in the same manner as for the reference polygons.

FIGS. 50A and 50B illustrate the guardband data as formatted by preprocessor2 20B of FIG. 53A. The guardband polygon data has been constructed in the same manner as for the reference data.

Figure 51C:
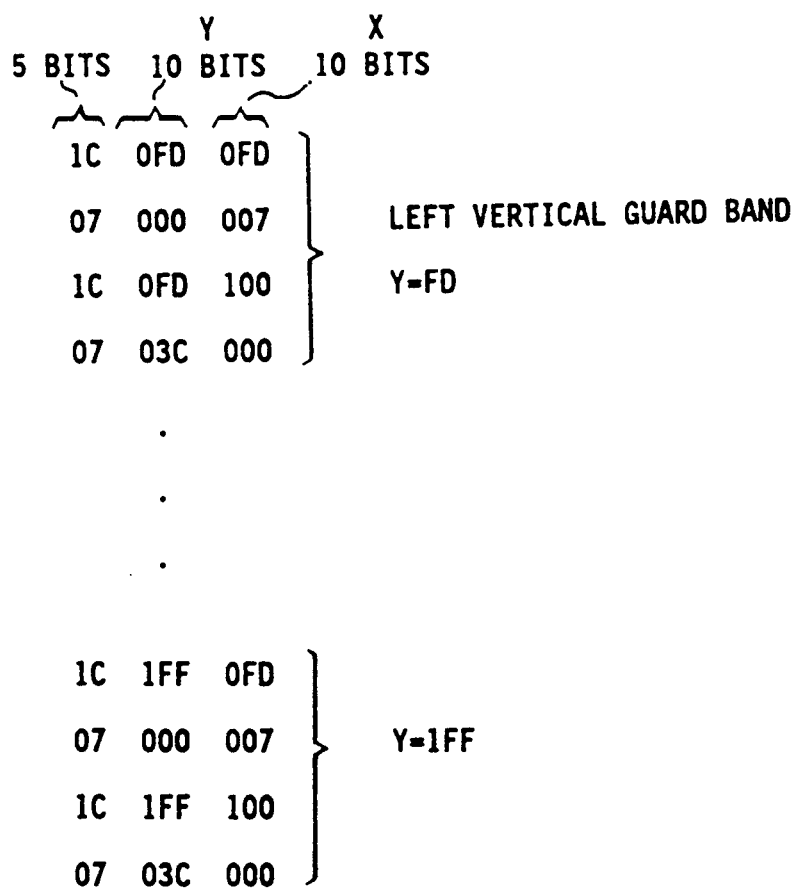

FIGS. 51A through 51C illustrate the guardband data as formatted by filler module2 23B of FIG. 53A.

The first 25 bit word of FIG. 51A has a 5 bit command field 342 equal to 1C hex, which indicates that in the pixel memory module, the guardband polygon data is to be logically ORed with the data already at that memory location. Since the pixel memory module starts with all its memory positions cleared to zero, this allows overlapping guardband information to be loaded into pixel memory. The second word begins with command field 342 which is equal to 07 hex. This indicates that the guard band polygon data bits 000007 hex will be loaded into memory and indicate three ones are to be set from X=1FD hex to X=1FF hex at Y=0FD hex. The following two 25 bit words set the four bits from X=200 to X=203 at Y=0FD hex. Thus, the seven bits which are on or in the interior of guardband polygon 249 at Y=0FD hex have been set by the first four 25 bit guardband data words. Similarly, the next four 25 bit guardband data words set the seven bit for guardband polygon 249 at Y=0FE hex, and so on down to the last Y address, Y=1FF hex for guardband polygon 249.

FIG. 51B illustrates the setting of the bits on or within guardband polygon 250. Here, eight 25 bit words are required since guardband polygon 250 extends from X=0FD hex to X=203 hex.

FIG. 51C illustrates the setting of the seven bits at each X address of guardband polygon 248, in a similar manner to what is illustrated in FIG. 51A for guardband 249, since they both have the same width in the X direction.

FIG. 52 illustrates the 64 bit word bit-map for the guardbands that are constructed by pixel memory module 24B, in a similar manner to that discussed in connection with FIG. 37 for the writer system 50.

As previously discussed, the guardband data from pixel memory module 24B is logically ANDed bit-at-a-time with the result of logically Exclusively ORing the corresponding bit from the scan data 257 with the corresponding bit from the reference data from pixel memory module 24A.

We claim:

1. A computerized method of eliminating false defect areas and consolidating defect areas in a pattern inspection system, comprising the steps of:
    comparing, one-by-one, the pixels of an ideal pattern with the corresponding pixels of a pattern on a target;
    counting the number of adjacent rows having miscompared pixels;
    comparing the number of rows of miscompared pixels with a first error criterion allowance; designating the miscompared pixels as a defect area if the first error criterion allowance comparisons produce a miscompare;
    designating first and second designated defect areas as a single consolidated defect area if the first and second designated defect areas are separated by a number of pixels less than or equal to a second error criterion allowance.

2. The method of claim 1, wherein the separation in number of pixels compared with the second error criterion allowance, measured in the X and Y direction.

3. The method of claim 2, further comprising the steps of:
    storing the minimum and maximum X coordinates of the consolidated defect area; and
    storing the minimum and maximum Y coordinates of the consolidated defect area.

4. The method of claim 3, further comprising the step of:
    storing the area in number of pixels, of the consolidated defect area.

5. The method of claim 1, wherein the step of comparing the pixels of the ideal pattern with the pixels of the pattern on the target, includes the step of:
    comparing, one-by-one, the bits of a bit-map of an ideal target, including the ideal pattern, with the corresponding pixels of the inspected target, including the pattern on the inspected target, wherein the pixels of the ideal pattern are the bits of the portion of the bit-map representing the ideal pattern.

* * * * *